United States Patent [19]
Nelson

[11] 3,944,593
[45] Mar. 16, 1976

[54] 3-OXA PROSTAGLANDIN E-TYPE COMPOUNDS

[75] Inventor: Norman A. Nelson, Galesburg, Mich.

[73] Assignee: The Upjohn Company, Kalamazoo, Mich.

[22] Filed: Apr. 17, 1974

[21] Appl. No.: 461,497

Related U.S. Application Data

[63] Continuation of Ser. No. 332,201, Feb. 13, 1973, abandoned, which is a continuation-in-part of Ser. No. 272,444, July 17, 1972, abandoned, which is a continuation-in-part of Ser. No. 47,169, June 17, 1970, abandoned.

[30] Foreign Application Priority Data

July 29, 1969 United Kingdom............... 38073/69

[52] U.S. Cl... 260/468 D; 260/211 R; 260/247.2 R; 260/268 R; 260/293.65; 260/326.2; 260/429.9; 260/439 R; 260/448 R; 260/488 R; 260/501.1; 260/501.15; 260/501.17; 260/501.2; 260/514 D

[51] Int. Cl.$^2$.................... C07C 61/38; C07C 69/74
[58] Field of Search..................... 260/468 D, 514 D

[56] References Cited
FOREIGN PATENTS OR APPLICATIONS
2,036,471 2/1971 Germany ........................... 260/468

OTHER PUBLICATIONS
Corey, Proceedings of The Robert A. Welsh Foundation, 11-13-1968.

Primary Examiner—Robert Gerstl
Attorney, Agent, or Firm—Morris L. Nielsen

[57] ABSTRACT

This invention is a group of 3-oxa PGE-type compounds, and processes for making them. These compounds are useful for a variety of pharmacological purposes, including antiulcer, inhibition and platelet aggregation, increase of nasal patency, labor inducement at term, and wound healing.

70 Claims, No Drawings

3-OXA PROSTAGLANDIN E-TYPE COMPOUNDS

CROSS REFERENCE TO RELATED APPLICATIONS

This application is a continuation of my copending application Ser. No. 332,201, filed Feb. 13, 1973, now abandoned, which was a continuation-in-part of my then copending application Ser. No. 272,444, filed July 17, 1972, now abandoned, which was a continuation-in-part of my copending application Ser. No. 47,169, filed June 17, 1970, now abandoned.

BACKGROUND OF THE INVENTION

This invention relates to compositions of matter, and to methods and intermediates for producing them. In particular, the several aspects of this invention relate to novel analogs of some of the known prostaglandins, for example, prostaglandin $E_1$ ($PGE_1$), prostaglandin $E_2$ ($PGE_2$), prostaglandin $F_1$ ($PGF_{1\alpha}$ and $PFG_{1\beta}$), prostaglandin $F_2$ ($PGF_{2\alpha}$ and $PGF_{2\beta}$), prostaglandin $A_1$ ($PGA_1$), prostaglandin $A_2$ ($PGA_2$), prostaglandin $B_1$ ($PGB_1$), prostaglandin $B_2$ ($PGB_2$), the corresponding $PG_3$'s, and the dihydro $PG_1$ derivatives, to novel methods for producing those novel prostaglandin analogs, and to novel chemical intermediates useful in those novel methods.

Each of the above-mentioned known prostaglandins is a derivative of prostanoic acid which has the following structure and atom numbering:

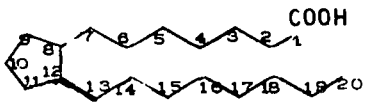

A systematic name for prostanoic acid is 7-[(2β-octyl)-cyclopent-1α-yl]heptanoic acid.

$PGE_1$ has the following structure:

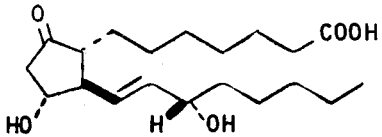

II $PGF_{1\alpha}$ has the following structure:

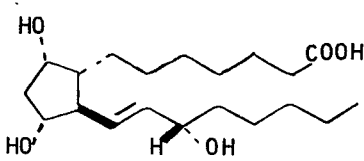

III $PGF_{1\beta}$ has the following structure:

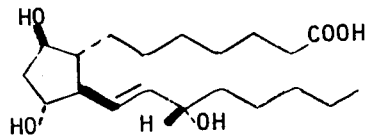

IV $PGA_1$ has the following structure:

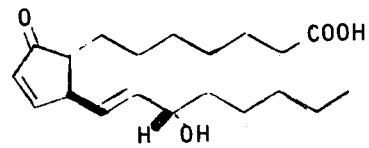

V $PGB_1$ has the following structure:

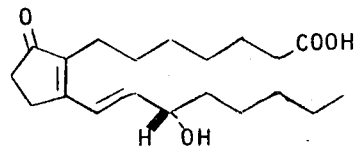

VI

Each of the known prostaglandins $PGE_2$, $PGF_{2\alpha}$, $PGF_{2\beta}$, $PGA_2$, and $PGB_2$ has a structure the same as that shown for the corresponding $PG_1$ compound except that in each, C-5 and C-6 are linked with a cis carbon-carbon double bond. For example, $PGE_2$ has the following structure:

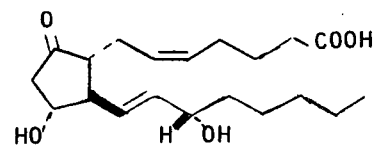

VII

Each of the known $PG_3$ prostaglandins has a structure the same as that of the $PG_2$ compounds except that in each, C-17 and C-18 are linked with a cis carbon-carbon double bond. For example, $PGE_3$ has the following structure:

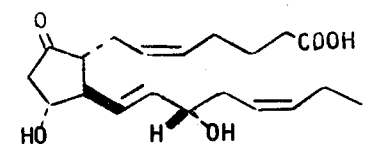

VIII

Each dihydro derivative of $PGE_1$, $PGF_{1\alpha}$, $PGF_{1\beta}$, $PGA_1$, and $PGB_1$ has a structure the same as that shown for the corresponding $PG_1$ compound except that in each, C-13 and C-14 are linked with a carbon-carbon single bond. For example, dihydro-$PGE_1$ has the following structure:

IX

The prostaglandin formulas mentioned above each have several centers of asymmetry. As drawn, formulas II to IX each represents the particular optically active form of the prostaglandin obtained from certain mammalian tissues, for example, sheep vesicular glands, swine lung, and human seminal plasma, or by reduction or dehydration of a prostaglandin so obtained. See, for example, Bergstrom et al., Pharmacol. Rev. 20, 1 (1968), and references cited therein. The mirror image of each formula represents a molecule of the enantiomer of that prostaglandin. The racemic form of the prostaglandin consists of equal numbers of two types of molecules, one represented by one of the above formulas and the other represented by the mirror image of that formula. Thus, both formulas are needed to define a racemic prostaglandin. See Nature 212, 38 (1966) for discussion of the stereochemistry of the prostaglandins.

In formulas I–IX, as well as in the formulas given hereinafter, broken line attachments to the cyclopentane ring indicate substituents in alpha configuration, i.e., below the plane of the cyclopentane ring. Heavy solid line attachments to the cyclopentane ring indicate substituents in beta configuration, i.e., above the plane of the cyclopentane ring.

Prostaglandins with carboxyl-terminated side chains attached to the cyclopentane ring in beta configuration are also known. These are derivatives of 8-iso-prostanoic acid which has the following formula:

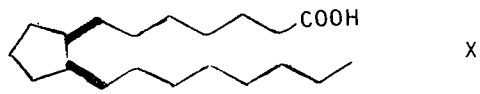

X

A systematic name for 8-iso-prostanoic acid is 7-[(2$\beta$-octyl)-cyclopent-1$\beta$-yl]heptanoic acid.

The side-chain hydroxy at C-15 in formulas II to IX is in alpha (S) configuration. See Nature 212, 38 (1966) for discussion of the stereochemistry of the prostaglandins.

$PGE_1$, $PGE_2$, dihydro-$PGE_1$, and the corresponding $PGF_\alpha$, $PGF_\beta$, PGA, and PGB compounds, and their esters, acylates, and pharmacologically acceptable salts, are extremely potent in causing various biological responses. For that reason, these compounds are useful for pharmacological purposes. See, for example, Bergstrom et al., Pharmacol. Rev. 20, 1 (1968), and references cited therein. A few of those biological respnses are systemic blood pressure lowering in the case of the PGE and PGA compounds as measured, for example, in anesthetized (pentobarbital sodium) pentolinium-treated rats with indwelling aortic and right heart cannulas; stimulation of smooth muscle as shown, for example, by tests on strips of guinea pig ileum, rabbit duodenum, or gerbil colon; potentiation of other smotth muscle stimulants; antilipolytic activity as shown by antagonism of epinephrine-induced mobilization of free fatty acids or inhibition of the spontaneous release of glycerol from isolated rat fat pads; inhibition of gastric secretion in the case of the PGE and PGA compounds as shown in dogs with secretion stimulated by food or histamine infusion; activity on the central nervous system; controlling spasm and facilitating breathing in asthmatic conditions; decreasing blood platelet adhesiveness as shown by platelet-to-glass adhesiveness, and inhibition of blood platelet aggregation and thrombus formation induced by various physical stimuli, e.g., arterial injury, and various biochemical stimuli, e.g., ADP, ATP, serotonin, thrombin, and collagen; and in the case of the PGE and PGB compounds, stimulation of epidermal proliferation and keratinization as shown when applied in culture to embryonic chick and rat skin segments.

Because of these biological responses; these known prostaglandins are useful to study, prevent, control, or alleviate a wide variety of diseases and undesirable physiological conditions in birds and mammals, including humans, useful domestic animals, pets, and zoological specimens, and in laboratory animals, for example, mice, rats, rabbits, and monkeys.

For example, these compounds, and especially the PGE compounds, are useful in mammals, including man, as nasal decongestants. For this purpose, the compounds are used in a dose range of about 10 $\mu$g. to about 10 mg. per ml. of a pharmacologically suitable liquid vehicle or as an aerosol spray, both for topical application.

The PGE, $PGF_\alpha$, $PGF_\beta$, and PGA compounds are useful in the treatment of asthma. For example, these compounds are useful as bronchodilators or as inhibitors of mediators, such as SRS-A, and histamine which are released from cells activated by an antigen-antibody complex. Thus, these compounds control spasm and facilitate breathing in conditions such as bronchial asthma, bronchitis, bronchiectasis, pneumonia and emphysema. For these purposes, these compounds are administered in a variety of dosage forms, e.g., orally in the form of tablets, capsules, or liquids; rectally in the form of suppositories; parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day, the exact dose depending on the age, weight, and condition of the patient and on the frequency and route of administration. For the above use these prostaglandins can be combined advantageously with other anti-asthmatic agents, such as sympathomimetics (isoproterenol, phenylephrine, ephedrine, etc.); xanthine derivatives (theophylline and aminophylline); and corticosteroids (ACTH and predinisolone). Regarding use of these compounds see South African Pat. No. 681,055.

The PGE and PGA compounds are useful in mammals, including man and certain useful animals, e.g., dogs and pigs, to reduce and control excessive gastric secretion, thereby reducing or avoiding gastrointestinal ulcer formation, and accelerating the healing of such ulcers already present in the gastrointestinal tract. For this purpose, the compounds are injected or infused intravenously, subcutaneously, or intramuscularly in an infusion dose range about 0.1 $\mu$g. to about 500 $\mu$g. per kg. of body weight per minute, or in a total daily dose by injection or infusion in the range about 0.1 to about 20 mg. per kg. of body weight per day, the exact dose depending on the age, weight, and condition of the patient or animal, and on the frequency and route of administration.

The PGE, $PGF_\alpha$, and $PGF_\beta$ compounds are useful whenever it is desired to inhibit platelet aggregation, to reduce the adhesive character of platelets, and to remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range about 0.005 to about 20 mg. per kg. of body weight per day are used, the exact dose depending on the age, weight, and condition of the patient or animal, and on the frequency and route of administration.

The PGE, PGF$_\alpha$, and PGF$_\beta$ compounds are especially useful as additives to blood, blood products, blood substitutes, and other fluids which are used in artificial extracorporeal circulation and perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of those at a total steady state dose of about 0.001 to 10 mg. per liter of circulating fluid. It is especially useful to use these compounds in laboratory animals, e.g., cats, dogs, rabbits, monkeys, and rats, for these purposes in order to develop new methods and techniques for organ and limb transplants.

PGE compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore, PGE$_2$, for example, is useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the PGE compound is administered by intravenous infusion immediately after abortion or delivery at a dose in the range about 0.01 to about 50 $\mu$g. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight, and condition of the patient or animal.

The PGE and PGA compounds are useful as hypotensive agents to reduce blood pressure in mammals, including man. For this purpose, the compounds are administered by intravenous infusion at the rate about 0.01 to about 50 $\mu$g. per kg. of body weight per minute or in single or multiple doses of about 25 to 500 $\mu$g. per kg. of body weight total per day.

The PGE, PGF$_\alpha$, and PGF$_\beta$ compounds are useful in place of oxytocin to induce labor in pregnant female animals, including man, cows, sheep, and pigs, at or near term, or in pregnant animals with intrauterine death of the fetus from about 20 weeks to term. For this purpose, the compound is infused intravenously at a dose of 0.01 to 50 $\mu$g. per kg. of body weight per minute until or near the termination of the second stage of labor, i.e., expulsion of the fetus. These compounds are especially useful when the female is one or more weeks post-nature and natural labor has not started, or 12 to 60 hours after the membranes have ruptured and natural labor has not yet started. An alternative route of administration is oral.

The PGE, PGF$_\alpha$, and PGF$_\beta$ compounds are useful for controlling the reproductive cycle in ovulating female mammals, including humans and animals such as monkeys, rats, rabbits, dogs, cattle, and the like. By the term ovulating female mammals is meant animals which are mature enough to ovulate but not so old that regular ovulation has ceased. For that purpose PGF$_{2\alpha}$, for example, is administered systemically at a dose level in the range 0.01 mg. to about 20 mg. per kg. of body weight of the female mammal, advantageously during a span of time starting approximately at the time of ovulation and ending approximately at the time of menses or just prior to menses. Intravaginal and intrauterine are alternative routes of administration. Additionally, expulsion of an embryo or a fetus is accomplished by similar administration of the compound during the first third of the normal mammalian gestation period.

The PGE and PGF compounds are useful in causing cervical dilation in pregnant and nonpregnant female mammals for purposes of gynecology and obstetrics. In labor induction and in clinical abortion produced by these compounds, cervical dilation is also observed. In cases of infertility, cervical dilation produced by PGE and PGF compounds is useful in assisting sperm movement to the uterus. Cervical dilation by prostaglandins is also useful in operative gynecology such as D and C (Cervical Dilation and Uterine Curettage) where mechanical dilation may cause perforation of the uterus, cervical tears, or infections. It is also useful in diagnostic procedures where dilation is necessary for tissue examination. For these purposes, the PGE and PGF compounds are administered locally or systemically. PGE$_2$, for example, is administered orally or vaginally at doses of about 5 to 50 mg. per treatment of an adult female human, with from one to five treatments per 24 hour period. PGE$_2$ is also administered intramuscularly or subcutaneously at doses of about one to 25 mg. per treatment. The exact dosages for these purposes depend on the age, weight, and condition of the patient or animal.

As mentioned above, the PGE compounds are potent antagonists of epinephrine-induced mobilization of free fatty acids. For this reason, this compound is useful in experimental medicine for both in vitro and in vivo studies in mammals, including man, rabbits, and rats, intended to lead to the understanding, prevention, symptom alleviation, and cure of diseases involving abnormal lipid mobilization and high free fatty acid levels, e.g., diabetes mellitus, vascular diseases, and hyperthyroidism.

The PGA compounds and derivatives and salts thereof increase the flow of blood in the mammalian kidney, thereby increasing volume and electrolyte content of the urine. For that reason, PGA compounds are useful in managing cases of renal disfunction, especially those involving blockage of the renal vascular bed. Illustratively, the PGA compounds are useful to alleviate and correct cases of edema resulting, for example, from massive surface burns, and in the management of shock. For these purposes, the PGA compounds are preferably first administered by intravenous injection at a dose in the range of 10 to 1000 $\mu$g. per kg. of body weight or by intravenous infusion at a dose in the range 0.1 to 20 μg. per kg. of body weight per minute until the desired effect is obtained. Subsequent doses are given by intravenous, intramuscular, or subcutaneous injection or infusion in the range 0.05 to 2 mg. per kg. of body weight per day.

The PGE and PGB compounds promote and accelerate the growth of epidermal cells and keratin in animals, including humans, useful domestic animals, pets, zoological specimens, and laboratory animals. For that reason, these compounds are useful to promote and accelerate healing of skin which has been damaged, for example, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection of homografts.

For these purposes, these compounds are preferably administered topically at or near the cite where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, when there is substantial fluid loss as in the case of extensive burns or skin loss due to other causes, systemic administration is advantageous, for example, by intravenous injection or infusion, separate or in combination with the usual infusions of blood, plasma, or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. To illustrate, a wet dressing for topical application to second and/or third degree burns of skin area 5 to 25 square centimeters would advantageously involve use of an isotonic aqueous solution containing 1 to 500 μg./ml. of the PGB compound or several times that concentration of the PGE compound. Especially for topical use, these prostaglandins are useful in combination with antibiotics, for example, gentamycin, neomycin, polymyxin B, bacitracin, spectinomycin, and oxytetracycline, with other antibacterials, for example, mafenide hydrochloride, sulfadiazine, furazolium chloride, and nitrofurazone, and with corticoid steroids, for example, hydrocortisone, prednisolone, methylprednisolone, and fluprednisolone, each of those being used in the combination at the usual concentration suitable for its use alone.

SUMMARY OF THE INVENTION

It is a purpose of this invention to provide novel 3-oxa and 4-oxa prostaglandin analogs, and processes for making them.

The novel prostaglandin analogs of this invention each have an oxygen (—O—) in place of the methylene (—CH$_2$—) moiety at the 3-position or at the 4-position of the prostanoic acid formula (I). For example, 3-oxa-PGE$_1$, one of the novel compounds of this invention, is represented by the formula:

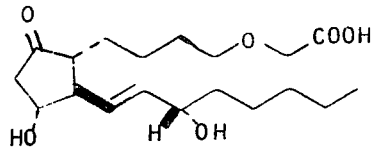

XI

The novel compound, 4-oxa-PGE$_1$, is represented by the formula:

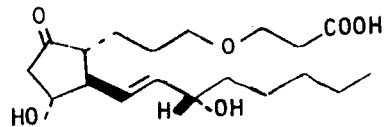

XII

Some of the novel prostaglandin analogs of this invention have a smaller or greater number of carbon atoms than the formulas shown above, in either the carboxy-terminated side chain or the alkyl-terminated side chain.

For example, five of the novel prostaglandin analogs of this invention are represented by the formulas:

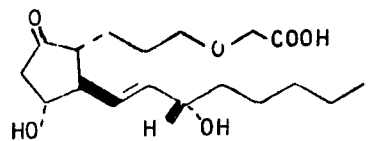

XIII

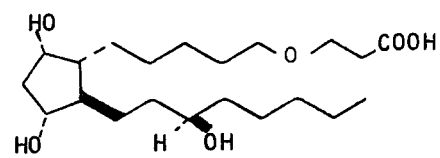

XIV

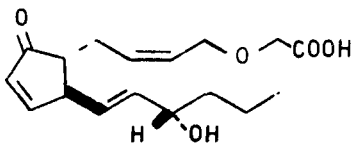

XV

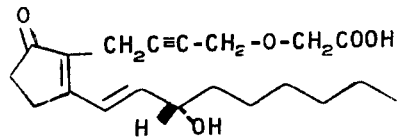

XVI

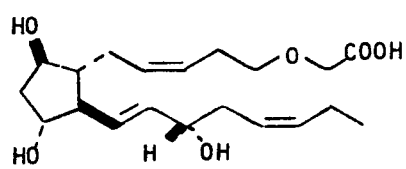

XVII

Based on its relationship to $PGE_1$ and prostanoic acid, the compound of formula XIII is named 3-oxa-4-nor-$PGE_1$; the compound of formula XIV is named 4-oxa-4a,4b-dihomo-13,14-dihydro-15-beta-$PGF_{1\alpha}$; the compound of formula XV is named 3-oxa-19,20-dinor-$PGA_2$; the compound of formula XVI is named 3-oxa-5,6-dehydro-20-methyl-$PGB_2$; and the compound of formula XVII is named 3-oxa-4a-homo-$PGF_{3\beta}$.

These names for the compounds of formulas XIII to XVII are typical of the names used hereinafter for the novel compounds of this invention. These names can better be understood by reference to the structure and numbering system of prostanoic acid (Formula I, above). That formula has seven carbon atoms in the carboxy-terminated chain and eight carbon atoms in the hydroxy-containing chain. In these names, "3-oxa" and "4-oxa" indicate an oxa oxygen (—O—) in place of the 3-methylene and 4-methylene, respectively of the PG compound.

The use of "nor" or "dinor" in the names for the novel compounds of this invention indicates the absence of one or two of the chain carbon atoms and the attached hydrogen atoms. The number or numbers in front of nor, or dinor indicate which of the original prostanoic acid carbon atoms are missing in the named compound.

The use of "homo" or "dihomo" as in the names of the formula-XIV and -XVII examples indicate one or two additional carbon atoms in the carboxy-terminated side chain. In the name of the formula-XIV example "4a,4b-dihomo" indicates two additional carbon atoms specifically between the oxygen atom at 4 and the C-5 carbon atom. There are, therefore, eight carbon atoms and one oxygen atom in that side chain instead of the six carbon atoms and one oxygen atom of the normal 3-oxa structure of this invention.

In the name of the formula-XVI example, "20-methyl" indicates that a methyl group replaces a hydrogen on C-20. The methyl-terminated chain of that example therefore has nine carbon atoms.

Where there is branching or fluoro substitution in the side chains, the points of attachment to the side chains are indicated in the conventional manner, following the atomic numbering of the prostanoic acid skeleton (I).

Novel compounds of this invention with epi configuration for the hydroxy at C-15 are so designated by using "15-beta" in the name. An example is the name given above for the compound of formula XIV. If 15-beta does not appear in the name, the natural configuration for the C-15 hydroxy, identified as the "S" configuration for $PGE_1$, is to be assumed.

The following formulas represent the novel 3-oxa and 4-oxa compounds of this invention in the same optically active form as the naturally occuring prostaglandins.

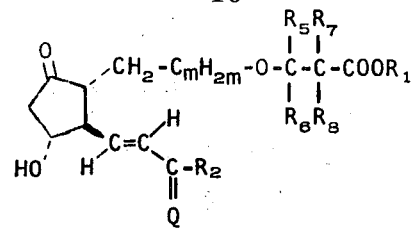

XIX

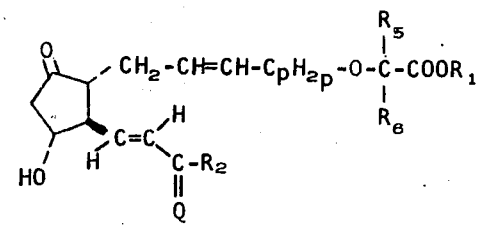

XX

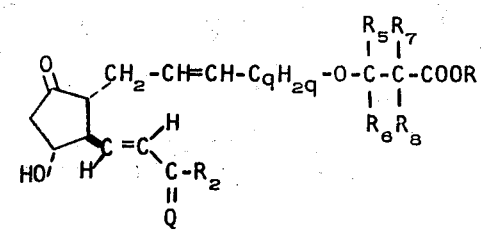

XXI

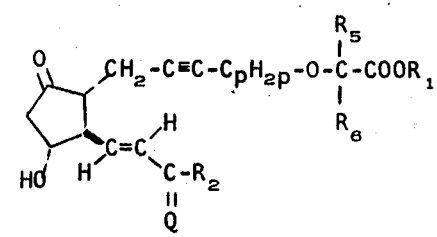

XXII

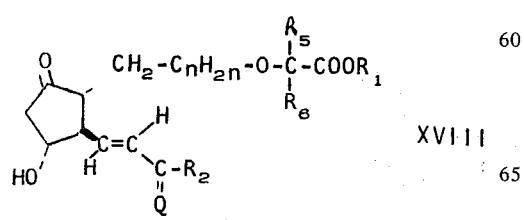

XVIII

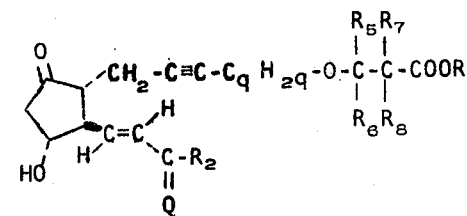

XXIII

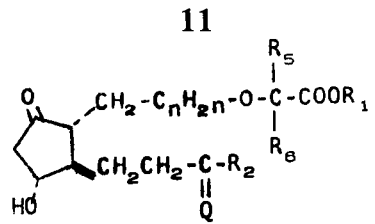 XXIV
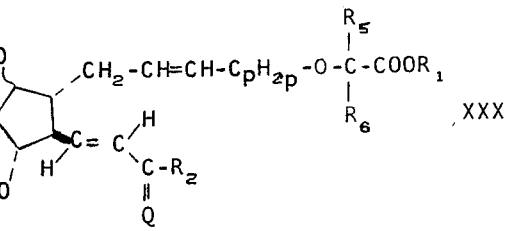 XXIX
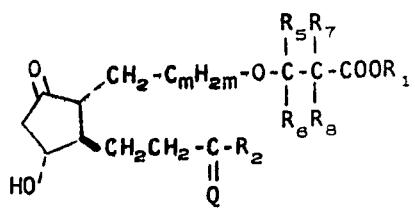 XXV
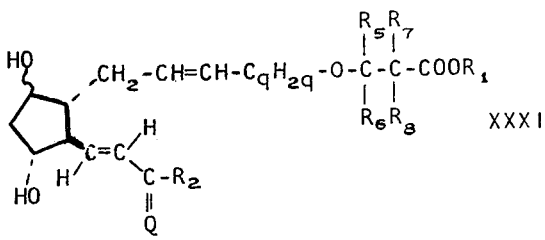 XXX
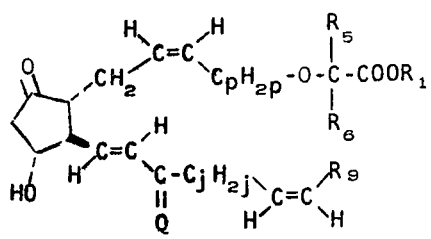 XXVI
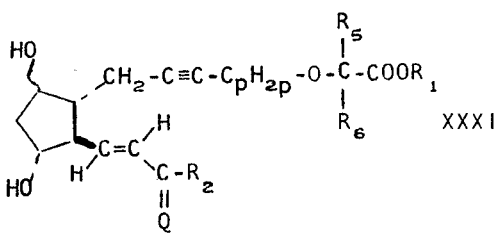 XXXI
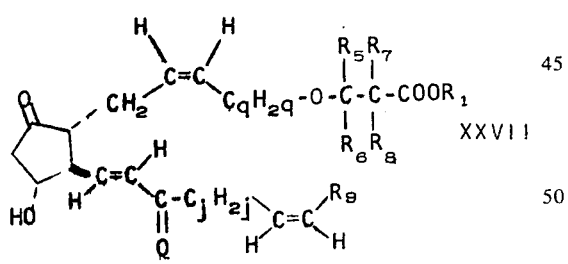 XXVII
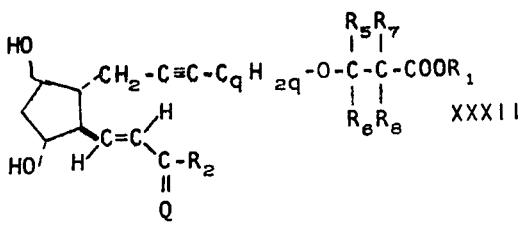 XXXII
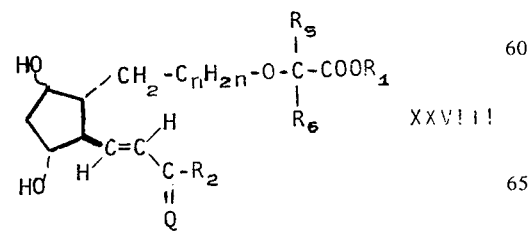 XXVIII
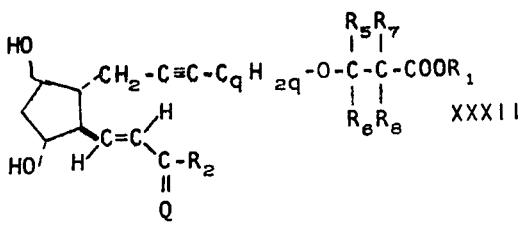 XXXIII

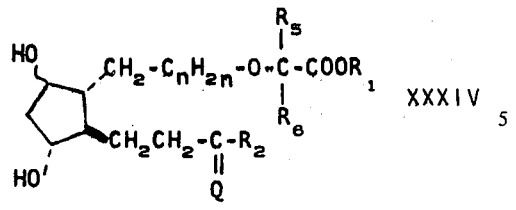 XXXIV
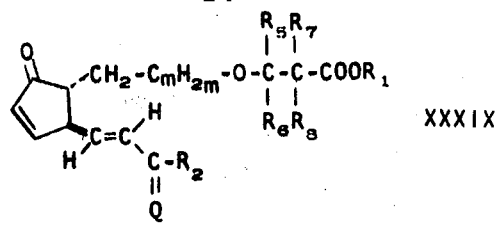 XXXIX
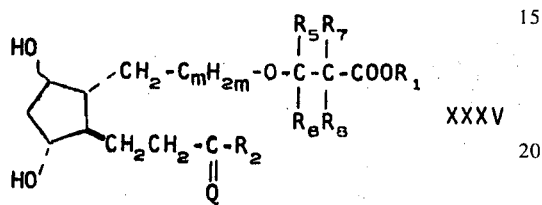 XXXV
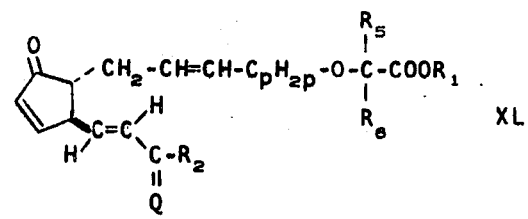 XL
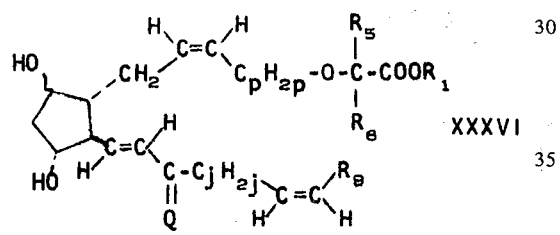 XXXVI
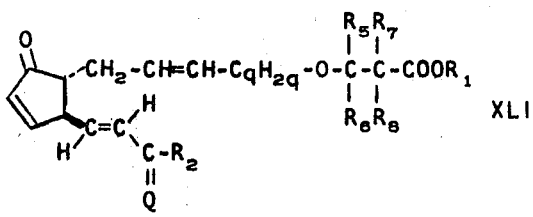 XLI
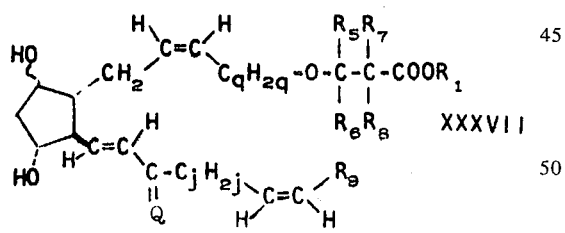 XXXVII
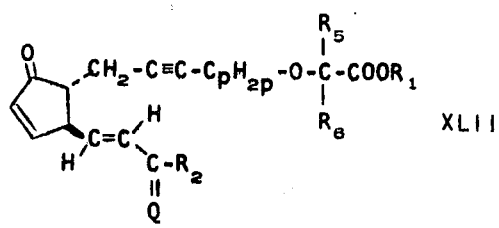 XLII
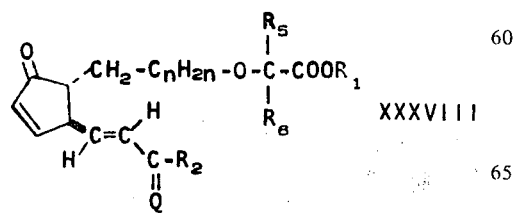 XXXVIII
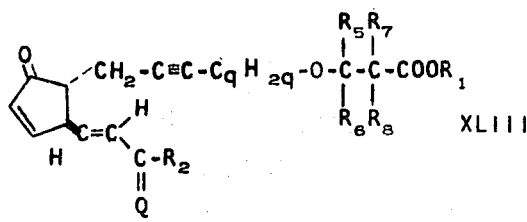 XLIII

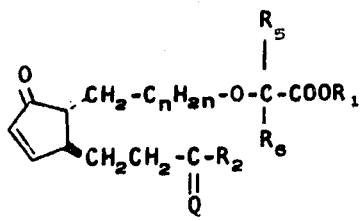 XLIV
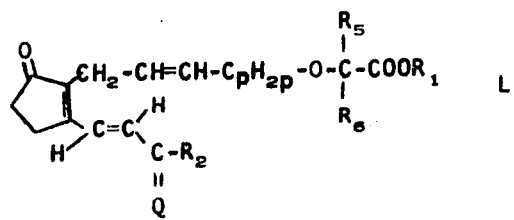 L
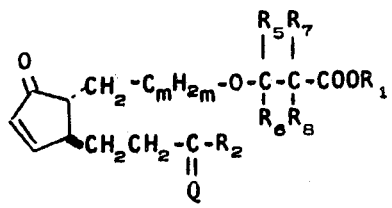 XLV
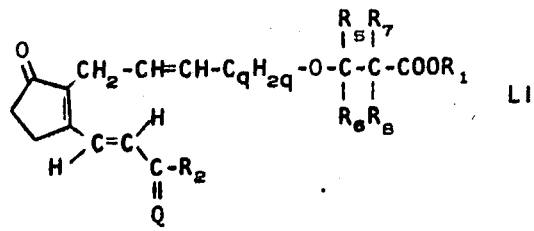 LI
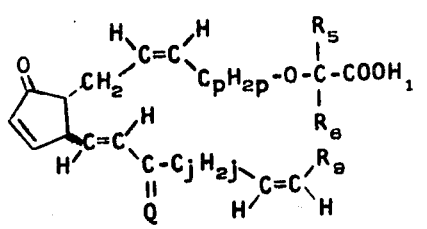 XLVI
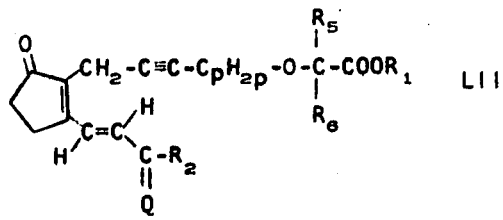 LII
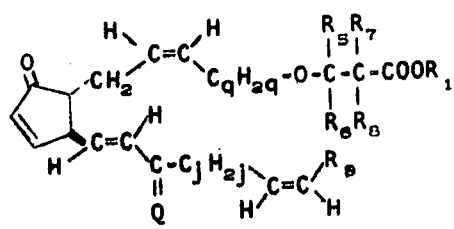 XLVII
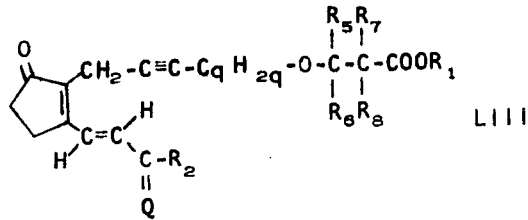 LIII
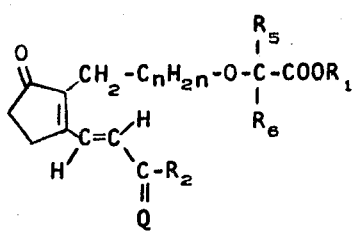 XLVIII
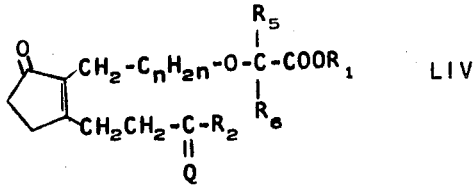 LIV
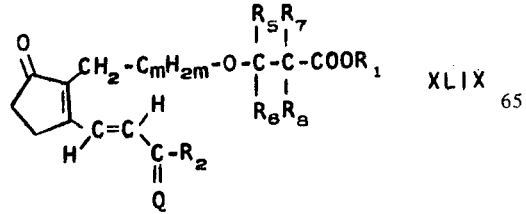 XLIX
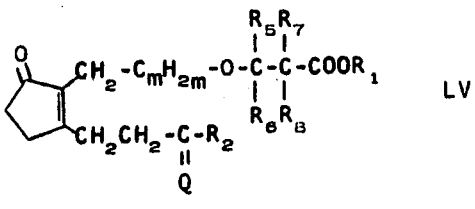 LV

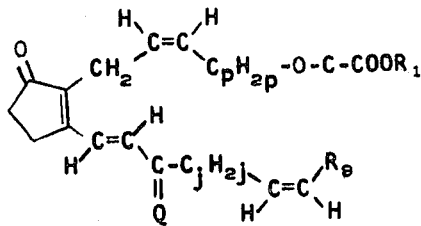

LVI

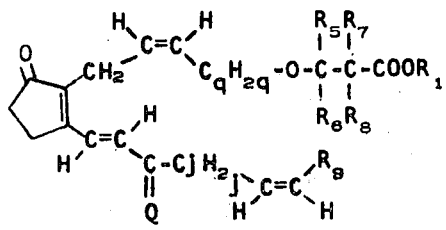

LVII

Formulas XVIII to XXVII represent 3-oxa and 4-oxa compounds of the PGE type. Formulas XXVIII to XXXVII represent 3-oxa and 4-oxa compounds of the PGF type. Formulas XXXVIII to XLVII represent 3-oxa and 4-oxa compounds of the PGA type. Formulas XLVIII to LVII represent 3-oxa and 4-oxa compounds of the PGR type.

In formulas XVIII to LVII, $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one to 3 chloro or alkyl of one to 4 carbon atoms, inclusive, or ethyl substituted in the β-position with 3 chloro, 2 or 3 bromo, or 1, 2, or 3 iodo. $R_2$ is alkyl of one to 10 carbon atoms, inclusive, substituted with zero to 3 fluoro. Q is

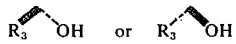

wherein $R_3$ is hydrogen or alkyl of one to 4 carbon atoms, inclusive. $R_9$ is alkyl of one to 4 carbon atoms, inclusive, substituted with zero, one, 2 or 3 fluoro. $R_5$, $R_6$, $R_7$, and $R_8$ are hydrogen or alkyl of one to 4 carbon atoms, inclusive. The divalent moiety —$C_nH_{2n}$— represents alkylene of one to 10 carbon atoms, inclusive, with one to 5 carbon atoms, inclusive, between —$CH_2$— and —O—. The divalent moiety —$C_mH_{2m}$— represents alkylene of one to 9 carbon atoms, inclusive, with one to 4 carbon atoms, inclusive, between —$CH_2$— and —O—. The divalent moiety —$C_pH_{2p}$— represents alkylene of one to 8 carbon atoms, inclusive, with one, 2, or 3 carbon atoms between —CH=CH— or —C≡C— and —O—. The divalent moiety —$C_qH_{2q}$— represents alkylene of one to 7 carbon atoms, inclusive, with one or 2 carbon atoms between —CH=CH— or —C≡C— and —O—. The divalent moiety —$C_jH_{2j}$— represents alkylene of one to 4 carbon atoms, inclusive. The wavy line ~ indicates attachment of the hydroxyl group to the ring in alpha or beta configuration.

Formulas XVIII through LVII include the separate isomers wherein Q is either

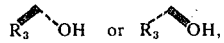

i.e., where the hydroxyl is in either alpha (natural) or beta configuration. Referring to the prostanoic acid atom numbering (formula I above), the point of attachment corresponds to C-15, and, herein, regardless of the variation in the C-1 to C-7 carboxy chain, these epimers are referred to as "C-15 epimers".

Formulas XXVIII through XXXVII wherein the C-9 hydroxyl (following prostanoic acid atom numbering) is attached to the cyclopentane with a wavy line ~ include both PGF$_\alpha$ - and PGF$_\beta$ -type compounds.

Included in formulas XX, XXI, XXX, XXXI, XL, XLI, l, and LI are both the cis and the trans compounds with respect to the C-5 to C-6 double bond in the carboxyl-terminated side chain. In all of the compounds containing the $C_{13}$-to-$C_{14}$ double bond, that double bond is in trans configuration, and the chain containing that moiety is attached to the cyclopentane ring in beta configuration in compounds encompassed by formulas XVIII to XLVII.

The novel 3-oxa and 4-oxa compounds of this invention include racemic compounds and both optically active enantiomeric forms thereof. As discussed hereinabove, two structural formulas are required to define accurately these racemic compounds. The formulas as drawn herein are intended to represent compounds with the same configuration as the naturally-occurring prostaglandins. However, for convenience in the charts herein only a single structural formula is used, for example in Chart E, to define not only the optically acive form but also the racemic compounds which generally undergo the same reactions.

Formula XVIII represents 3-oxa-PGE$_1$ (formula XI hereinabove) when $C_nH_{2n}$ is —$(CH_2)_3$—, Q is

$R_1$, $R_5$, and $R_6$ are hydrogen, and $R_2$ is n-pentyl.

With regard to formulas XVIII to LVII, examples of alkyl of one to 4 carbon atoms, inclusive, are methyl, ethyl, propyl, butyl, and isomeric forms thereof. Examples of alkyl of one to 8 carbon atoms, inclusive, are those given above, and pentyl, hexyl, heptyl, octyl, and isomeric forms thereof. Examples of alkyl of one to 12 carbon atoms, inclusive, are those given above, and nonyl, decyl, undecyl, dodecyl, and isomeric forms thereof. Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 3-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl. Examples of aralkyl of 7 to 12 carbon atoms, inclusive, are benzyl, phenethyl, 1-phenylethyl, 2-phenylpropyl, 4-phenylbutyl, 3-phenylbutyl, 2-(1-naphthylethyl), and 1-(2-naphthylmethyl), Examples of phenyl substituted by one to 3 chloro or alkyl of one to 4 carbon atoms, inclusive, are p-chlorophenyl, m-chlorophenyl, o- chlorophenyl, 2,4-dichlorophenyl, 2,4,6-trichlorophenyl, p-tolyl, m-tolyl, o-tolyl, p-ethylphenyl, p-tert-butylphenyl, 2,5-dimethylphenyl, 4-chloro-2-methylphenyl, and 2,4-dichloro-3-methylphenyl.

Examples of alkyl of one to 10 carbon atoms, inclusive, substituted with one to 3 fluoro, are fluoromethyl, 2-fluoroethyl, 2-fluorobutyl, 3-fluorobutyl, 4-fluorobutyl, 5-fluoropentyl, 4-fluoro-4-methylpentyl, 3-fluoroisoheptyl, 8-fluorooctyl, 3,4-difluorobutyl, 4,4-difluoropentyl, 5,5-difluoropentyl, 5,5,5-trifluoropentyl, and 10,10,10-trifluorodecyl.

Examples of alkylene within the various scopes of $C_jH_{2j}$, $C_mH_{2m}$, $C_nH_{2n}$, $C_pH_{2p}$, and $C_qH_{2q}$, as those are defined above, are methylene, ethylene, trimethylene, tetramethylene, pentamethylene, and those alkylene with one or more alkyl substituents on one or more carbon atoms thereof, e.g., $-CH(CH_3)-$, $-C(CH_3)_2-$, $-CH(CH_2CH_3)-$, $-CH_2-CH(CH_3)-$, $-CH(CH_3)-CH(CH_3)-$, $-CH_2-C(CH_3)_2-$, $-CH_2-CH(CH_3)-CH_2-$, $-CH_2-CH_2-CH(CH_2CH_2CH_3)-$, $-CH(CH_3)-CH(CH_3)-CH_2-CH_2-$, $-CH_2-CH_2-CH_2-C(CH_3)_2-CH_2-$, and $-CH_2-CH_2-CH_2-CH(CH_3)-$.

The novel formula XVIII-XXVII PGE-type 3-oxa and 4-oxa compounds, the novel formula XXVIII-XXXVII PGFα-type and PGFβ-type 3-oxa and 4-oxa compounds, the novel formula XXXVIII-XLVII PGA-type 3-oxa and 4-oxa compounds, and the novel formula XLVIII-LVII PGB-type 3-oxa and 4-oxa compounds, and their racemic forms, each cause the biological responses described above for the PGE, PGFα, PGFβ, PGA, and PGB compounds, respectively, and each of these novel compounds is accordingly useful for the above-described corresponding purposes, and is used for those purposes in the same manner as described above.

The known PGE, PGFα, PGFβ, PGA, and PGB compounds uniformly cause multiple biological responses even at low doses. For example, PGE₁ and PGE₂ both cause vasodepression and smooth muscle stimulation at the same time they exert antipolytic activity. Moreover, for many applications, these known prostaglandins have an inconveniently short duration of biological activity. In striking contrast, the novel formula XVIII-to-LVII analogs and their racemic forms are substantially more specific with regard to potency in causing prostaglandin-like biological responses, and have a substantially longer duration of biological activity. Therefore, each of these novel prostaglandin analogs is useful in place of one of the corresponding above-mentioned known prostaglandins for at least one of the pharmacological purposes indicated above for the latter, and is surprisingly and unexpectedly more useful for that purpose because it has a different and narrower spectrum of biological activity than the known prostaglandin, and therefore is more specific in its activity and causes smaller and fewer undesired side effects than the known prostaglandin. Moreover, because of its prolonged activity, fewer and smaller doses of the novel prostaglandin analog can frequently be used to attain the desired result.

To obtain the optimum combination of biological potency specificity and duration of activity, certain compounds within the scope of formulas XVIII to LVII are preferred. For example, it is preferred that the carboxyterminated chain in each formula contain a chain of six atoms between the carboxyl and the cyclopentane ring. One of those six atoms will be the oxa atom and the other five will be carbon atoms. Accordingly and with reference to formulas XVIII to LVII, it is preferred that $-C_nH_{2n}-$ represent a 3-carbon divalent chain, that $-C_mH_{2m}-$ represent a 2-carbon divalent chain, and that $-C_pH_{2p}-$ represent a divalent carbon atom. These preferences do not exclude additional carbon atoms (alkyl groups) as branching.

A seven-atom carboxy terminated chain is not included in the compounds of formulas XXI, XXIII, XXVII, XXXI, XXXIII, XXXVII, XLI, XLIII, XLVII, LI, LIII, and LVII, i.e., formulas wherein the carboxy-terminated side chain is 4-oxa and contains a carbon-carbon double or triple bond. In each of those compounds, the $q$ of $-C_qH_{2q}$ is at least one, and at least seven atoms, one oxygen (oxa) and six carbons, are present between the carboxyl and the cyclopentane ring. In these compounds, the preference is for that minimum chain, i.e., $q$ is one.

Another preference for the compounds of formulas XVIII to LVII is that $R_3$, $R_5$, $R_6$, $R_7$, and $R_o$ be hydrogen or methyl. All of those R groups can be hydrogen, all can be methyl, or there can be any of the possible combinations of hydrogen and methyl. It is especially preferred for prolonged duration of biological activity that both $R_5$ and $R_6$ be methyl, and/or that $R_3$ be methyl.

Certain variations in the nature of $R_2$ in formulas XVIII–XXV, XXVIII–XXXV, XXXVIII–XLV, and XLVIII–LV are especially important. In the known prostaglandins, e.g., PGE₁, the portion of the molecule corresponding to $R_2$ in the above-mentioned formulas is pentyl. It is preferred that $R_2$ be pentyl in formulas XVIII–XXV, XXVIII–XXXV, XXXVII–XLV, and XLVIII–LV. It is also preferred that $R_2$ be straight chain alkyl of 3 to 7 carbon atoms, inclusive, with or without a fluoro substituent at the 1-position, e.g., $-CHF-(CH_2)_g-CH_3$ wherein $g$ is one to 5. Alternately, $R_2$ is represented by

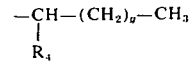

wherein $R_4$ is hydrogen or fluoro and $g$ is 1, 2, 3, 4, or 5. Pentyl and 1-fluoropentyl are, of course, included in this preference.

In compounds of formulas XXVI, XXVII, XXXVI, XXXVII, XLVI, XLVII, LVI, and LVII, it is preferred that $C_jH_{2j}$ be methylene and that $R_a$ be ethyl.

Another advantage of the novel compounds of this invention, especially the preferred compounds defined hereinabove, compared with the known prostaglandins, is that these novel compounds are administered effectively orally, sublingually, intravaginally, buccally, or rectally, in addition to usual intravenous, intramuscular, or subcutaneous injection or infusion methods indicated above for the uses of the known prostaglandins. These qualities are advantageous because they facilitate maintaining uniform levels of these compounds in the body with fewer, shorter, or smaller doses, and make possible self-administration by the patient.

The PGE, PGFα, PGFβ, PGA, and PGB type 3-oxa and 4-oxa compounds encompassed by formulas XVIII to LVII including the special classes of compounds described above, are used for the purposes described above in the free acid form, in ester form, or in pharmacologically acceptable salt form. When the ester form is used the ester is any of those within the above definition of $R_1$. However, it is preferred that the ester be alkyl of one to 12 carbon atoms, inclusive. Of those alkyl, methyl and ethyl are especially preferred for optimum absorption of the compound by the body or experimental animal system; and straight-chain octyl, nonyl, decyl, undecyl, and dodecyl are especially preferred for prolonged activity in the body or experimental animal.

Pharmacologically acceptable salts of these formula XVIII-to-LVII compounds useful for the purposes described above are those with pharmacologically acceptable metal cations, ammonium, amine cations, or quaternary ammonium cations.

Especially preferred metal cations are those derived from the alkali metals, e.g., lithium, sodium and potassium, and from the alkaline earth metals, e.g., magnesium and calcium, although cationic forms of other metals, e.g., aluminum, zinc, and iron, are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, $\alpha$-phenylethylamine, $\beta$-phenylethylamine, ethylenediamine, diethylenetriamine, and like aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, n-butylethanolamine, 2-amino-1-butanol, 2-amino-2-ethyl-1,3-propanediol, 2-amino-2-methyl-1-propanol, tris-(hydroxymethyl)aminomethane, N-phenylethanolamine, N-(p-tert-amylphenyl)-diethanolamine, galactamine, N-methylglucamine, n-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

The 3-oxa and 4-oxa PGE, PGF $\alpha$, PGF $\beta$, PGA, and PGB type compounds encompassed by formulas XVIII to LVII including the special classes of compounds described above, are also used for the purposes described above in free hydroxy form or in the form wherein the hydroxy moieties are transformed to lower alkanoate moieties, e.g., —OH to —OCOCH$_3$. Examples of lower alkanoate moieties are acetoxy, propionyloxy, butyryloxy, valeryloxy, hexanoyloxy, heptanoyloxy, octanoyloxy, and branched chain alkanoyloxy isomers of those moieties. Especially preferred among these alkanoates for the above described purposes are the acetoxy compounds. These free hydroxy and alkanoyloxy compounds are used as free acids, as esters, and in salt form all as described above.

As discussed above, the compounds of formulas XVIII to LVII are administered in various ways for various purposes; e.g., intravenously, intramuscularly, subcutaneously, orally, intravaginally, rectally, buccally, sublingually, topically, and in the form of sterile implants for prolonged action. For intravenous injection or infusion, sterile aqueous isotonic solutions are preferred. For that purpose, it is preferred because of increased water solubility that $R_1$ in the formula XVIII-to-LVII compound be hydrogen or a pharmacologically acceptable cation. For subcutaneous or intramuscular injection, sterile solutions or suspensions of the acid, salt, or ester form in aqueous or non-aqueous media are used. Tablets, capsules, and liquid preparations such as syrups, elixirs, and simple solutions, with the usual pharmaceutical carriers are used for oral sublingual administration. For rectal or vaginal administration, suppositories prepared as known in the art are used. For tissue implants, a sterile tablet or silicone rubber capsule or other object containing or impregnated with the substance is used.

The 3-oxa and 4-oxa PGE, PGF $\alpha$, PGF $\beta$, PGA, and PGB type compounds encompassed by formulas XVIII to LVII are produced by the reactions and procedures described and exemplified hereinafter.

The various 3-oxa and 4-oxa PGF $\alpha$ -type and PGF $\beta$ -type compounds encompassed by formulas XXVIII–XXXVII are prepared by carbonyl reduction of the corresponding PGE type compounds encompassed by formulas XVIII–XXVII. For example, carbonyl reduction of 3-oxa PGE$_1$ gives a mixture of 3-oxa PGF$_1$ $\alpha$ and 3-oxa PGF$_1\beta$.

These ring carbonyl reductions are carried out by methods known in the art for ring carbonyl reductions of known prostanoic acid derivatives. See, for example, Bergstrom et al., Arkiv Kemi 19, 563 (1963), Acta Chem. Scand. 16, 969 (1962), and British Pat. Specification No. 1,097,533. Any reducing agent is used which does not react with carbon-carbon double bonds or ester groups. Preferred reagents are lithium(tri-tert-butoxy)aluminum hydride, the metal borohydrides, especially sodium, potassium and zinc borohydrides, and metal trialkoxy borohydrides, e.g., sodium trimethoxyborohydride. The mixtures of alpha and beta hydroxy reduction products are separated into the individual alpha and beta isomers by methods known in the art for the separation of analogous pairs of known isomeric prostanoic acid derivatives. See, for example, Bergstrom et al., cited above, Granstrom et al., J. Biol. Chem. 240, 457 (1965), and Green et al., J. Lipid Research 5, 117 (1964). Expecially preferred as separation methods are partition chromatographic procedures, both normal and reversed phase, preparative thin layer chromatography, countercurrent distribution procedures, and column chromatography.

The various 3-oxa and 4-oxa PGA-type compounds encompassed by formulas XXXVIII–XLVII are prepared by acidic dehydration of the corresponding PGE type compounds encompassed by formulas XVIII–XXVII. For example, acidic dehydration of 3-oxa PGE$_1$ gives 3-oxa PGA$_1$.

These acidic dehydrations are carried out by methods known in the art for acidic dehydrations of known prostanoic acid derivatives. See, for example, Pike et al., Proc. Nobel Symposium II, Stockholm (1966), Interscience Publishers, New York, pp. 162–163 (1967); and British Pat. Specification No. 1,097,533. Alkanoic acids of 2 to 6 carbon atoms, inclusive, especially acetic acid, are preferred acids for this acidic dehydration. Dilute aqueous solutions of mineral acids, e.g., hydrochloric acid, especially in the presence of a solubilizing diluent, e.g., tetrahydrofuran, are also useful as reagents for this acidic dehydration, although these reagents may cause partial hydrolysis of an ester reactant.

The various 3-oxa and 4-oxa PGB-type compounds encompassed by formulas XLVII–LVII are prepared by basic dehydration of the corresponding PGE type compounds encompassed by formulas XVIII–XXVII, or by contacting the corresponding PGA compounds encompassed by formulas XXXVIII–XLVII with base. For example, both 3-oxa $PGE_1$ and 3-oxa $PGA_1$ give 3-oxa $PGB_1$ on treatment with base.

These basic dehydrations and double bond migrations are carried out by methods known in the art for similar reactions of known prostanoic acid derivatives. See, for example, Bergstrom et al., J. Biol. Chem. 238, 3555 (1963). The base is any whose aqueous solution has pH greater than 10. Preferred bases are the alkali metal hydroxides. A mixture of water and sufficient of a water-miscible alkanol to give a homogeneous reaction mixture is suitable as a reaction medium. The PGE-type or PGA-type compound is maintained in such a reaction medium until no further PGB-type compound is formed, as shown by the characteristic ultraviolet light absorption near 278 nm for the PGB type compound.

CHART A

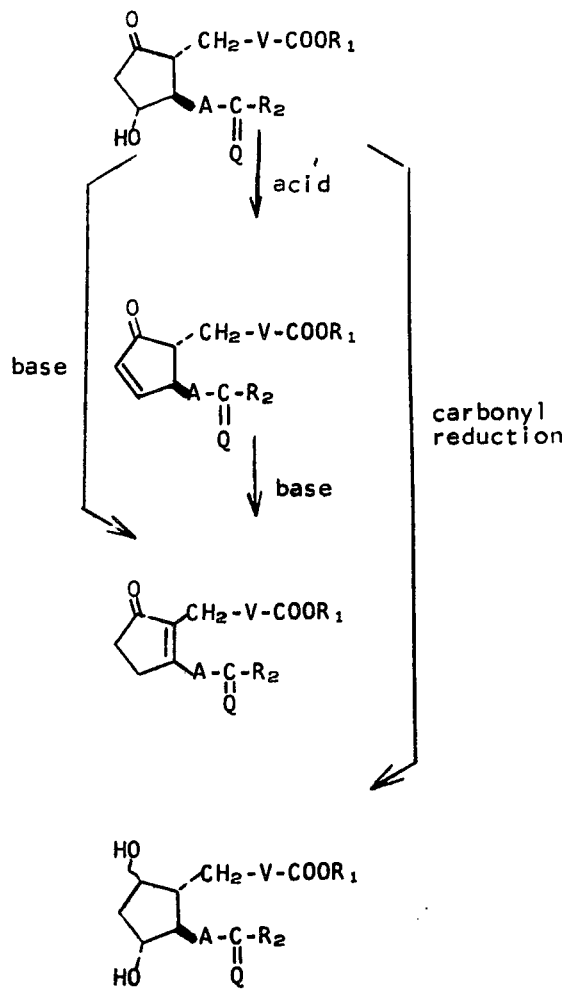

The various transformations of 3-oxa and 4-oxa PGE type compounds of formulas XVIII to XXV to the corresponding 3-oxa and 4-oxa $PGF_\alpha$, $PGF_\beta$, PGA, and PGB type compounds are shown in Chart A, wherein Q, $R_1$, $R_2$, and ~ are as defined above, and wherein A is $-CH_2-CH_2-$ or trans $-CH=CH-$, Q is

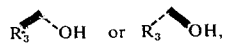

and V is $-C_nH_{2n}-O-CR_5R_6-$, $-C_mH_{2m}-O-CR_5R_6-CR_7R_8-$, $-CH=CH-C_pH_{2p}-O-CR_5R_6-$ (cis or trans), $-CH=CH-C_qH_{2q}-O-CR_5R_6-CR_7R_8-$ (cis or trans), $-C\equiv C-C_pH_{2p}-O-CR_5R_6-$, or $-C\equiv C-C_qH_{2q}-O-CR_5R_6-CR_7R_8-$, wherein $R_5$, $R_6$, $R_7$, $R_8$, $C_nH_{2n}$, $C_mH_{2m}$, $C_pH_{2p}$, and $C_qH_{2q}$ are as defined above, with the proviso that V is $-C_nH_{2n}-O-CR_5R_6-$ or $-C_mH_{2m}-O-CR_5R_6-CR_7R_8-$ when A is $-CH_2-CH_2-$. The 3-oxa and 4-oxa $PGE_3$ type compounds of formulas XXVI and XXVII are transformed to the corresponding 3-oxa and 4-oxa $PGF_{3\alpha}$, $PGF_3\beta$, $PGA_3$, and $PGB_3$ compounds by analogous reactions.

The various 3-oxa and 4-oxa dihydro-$PGE_1$, dihydro-$PGF_1\alpha$, dihydro-$PGF_1\beta$, dihydro-$PGA_1$, and dihydro-$PGB_1$ type compounds encompassed by formulas XXIV, XXV, XXXIV, XXXV, XLIV, XLV, LIV, and LV are prepared by carbon-carbon double bond reduction of the corresponding PGE, $PGF_\alpha$, $PGF_\beta$, PGA, and PGB type compound containing a trans double bond in the hydroxy-containing side chain. A cis or trans double bond or an acetylenic bond can also be present in the carboxy-terminated side chain of the unsaturated reactant, and will be reduced at the same time to $-CH_2CH_2-$. For example, dihydro-3-oxa-$PGE_1$ is produced by reduction of 3-oxa-$PGE_1$, 3-oxa-$PGE_2$, or 5,6-dehydro-3-oxa-$PGE_2$.

These reductions are carried out by reacting the unsaturated PGE, PGF $\alpha$, PGF $\beta$, PGA, or PGB type compound with diimide, following the general procedure described by van Tamelen et al., J. Am. Chem. Soc., 83, 3726 (1961). See also Fieser et al., "Topics in Organic Chemistry," Reinhold Publishing Corp., New York, pp. 432–434 (1963) and references cited therein. The unsaturated acid or ester reactant is mixed with a salt of azodiformic acid, preferably an alkali metal salt such as the disodium or dipotassium salt, in the presence of an inert diluent, preferably a lower alkanol such as methanol or ethanol, and preferably in the absence of substantial amounts of water. At least one molecular equivalent of the azodiformic acid salt is used for each multiple bond equivalent of the unsaturated reactant. The resulting suspension is then stirred, preferably with exclusion of oxygen, and the mixture is made acid, advantageously with a carboxylic acid such as acetic acid. When a reactant wherein $R_1$ is hydrogen is used, that carboxylic acid reactant also serves to acidify an equivalent amount of the azodiformic acid salt. A reaction temperature in the range about 10° to about 40° C. is usually suitable. Within that temperature range, the reaction is usually complete within less than 24 hours. The desired dihydro product is then isolated by conventional methods, for example, evaporation of the diluent, followed by separation from inorganic materials by solvent extraction.

In the case of the 3-oxa and 4-oxa unsaturated PGE, $PGF_\alpha$, and $PGF_\beta$ type reactants, the reductions to the corresponding 3-oxa and 4-oxa dihydro-$PGE_1$, dihydro-$PFG_{1\alpha}$, and dihydro-$PGF_{1\beta}$ compounds are also carried out by catalytic hydrogenation. For that purpose, palladium catalysts, expecially on a carbon carrier, are preferred. It is also preferred that the hydrogenation be carried out in the presence of an inert liquid diluent, for example, methanol, ethanol, dioxane, ethyl acetate, and the like. Hydrogenation pressures ranging from about atmospheric to about 50 p.s.i., and hydrogenation temperatures ranging from about 0° to about 100° C. are preferred. The resulting dihydro product is isolated from the hydrogenation reaction mixture by conventional methods, for example, removal of the catalyst by filtration or centrifugation, followed by evaporation of the solvent.

Diimide reductions and catalytic hydrogenations to produce the various novel 3-oxa and 4-oxa dihydro compounds of this invention from the corresponding 3-oxa and 4-oxa $PGE_1$, $PGF_{1\alpha}$, $PGF_{1\beta}$, $PGA_1$, and $PGB_1$ type compounds are shown in Chart B, wherein Q, $R_1$, $R_2$, and ~ are as defined above, and W is —$C_nH_{2n}$—O—$CR_5R_6$— or —$C_mH_{2m}$—o—$CR_5R_6$—$CR_7R_8$—, wherein $C_nH_{2n}$, $C_mH_{2m}$, $R_5$, $R_6$, $R_7$, and $R_8$ are as defined above.

CHART B

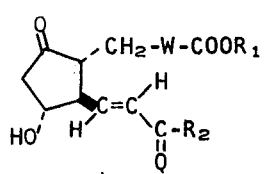

diimide or
hydrogen +
catalyst

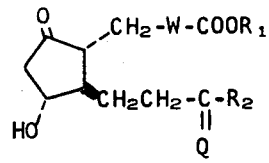

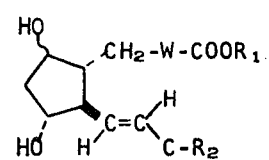

diimide or
hydrogen +
catalyst

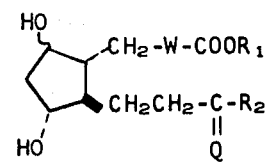

CHART B continued

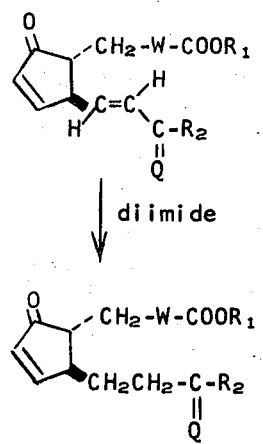

diimide

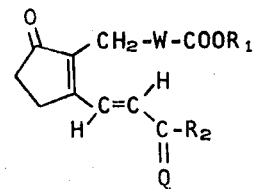

diimide

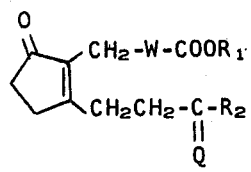

These diimide reductions and catalytic hydrogenations to produce the same novel 3-oxa and 4-oxa dihydro compounds of this invention from the corresponding 3-oxa and 4-oxa $PGE_2$, $PGF_{2\alpha}$, $PGF_{2\beta}$, $PGA_2$, and $PGB_2$ type compounds and also from the corresponding compounds with a trans-ethylenic or an acetylenic linkage in place of the cis-ethylenic linkage in the carboxyl-terminated side chain, are shown in Chart C, wherein Q, $R_1$, $R_2$, and ~ are as defined above, U is cis—CH=CH—, trans—CH=CH—, or —C≡C—, and Y is —$C_pH_{2p}$—O—$CR_5R_6$— or —$C_qH_{2q}$— O—$CR_5R_6$—$CR_7R_8$—, wherein p, q, $R_5$, $R_6$, $R_7$, and $R_8$ are as defined above.

The 3-oxa and 4-oxa compounds of the $PGE_2$, $PGF_{2\alpha}$, $PGF_{2\beta}$, $PGA_2$, and $PGB_2$ type wherein the carbon-carbon double bond in the carboxy-terminated side chain is in cis configuration are prepared by reduction of the corresponding acetylenic 3-oxa and 4-oxa compounds, i.e., those with a carbon-carbon triple bond in place of said carbon-carbon double bond. For that purpose, there are used any of the known reducing agents which reduce an acetylenic linkage to a cis-ethylenic linkage. Especially preferred for that purpose are diimide or hydrogen and a catalyst, for example, palladium (5%) on barium sulfate, especially in the presence of pyridine. See Fieser et al., "Reagents for Organic Synthesis," pp. 566–567, John Wiley & Sons, Inc., New York, N.Y. (1967). These reductions are shown in Chart D, wherein Q, $R_1$, $R_2$, and ~ are as defined above, and Y is —$C_pH_{2p}$—O—$CR_5R_6$— or —$C_qH_{2q}$—O—$CR_5R_6$— $CR_7R_8$—. These 3-oxa and 4-oxa cis compounds of the PGE$_2$, PGF$_{2\alpha}$, PGF$_{2\beta}$, PGA$_2$, and PGB$_2$ type are also prepared as described hereinafter.

CHART C

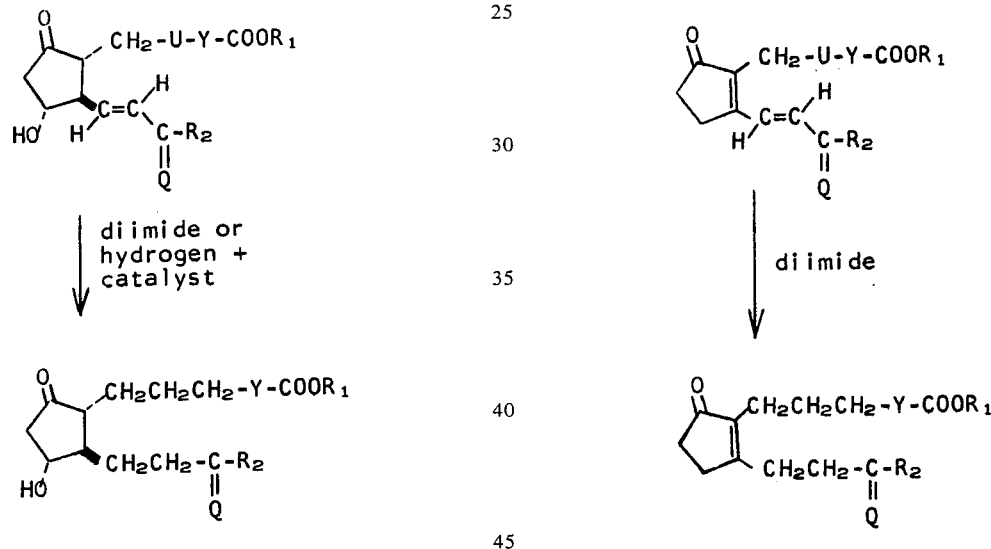

CHART C continued

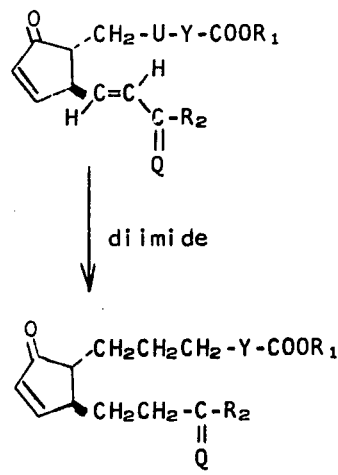

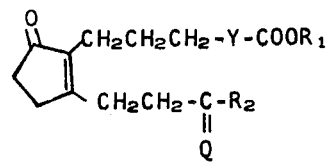

CHART D

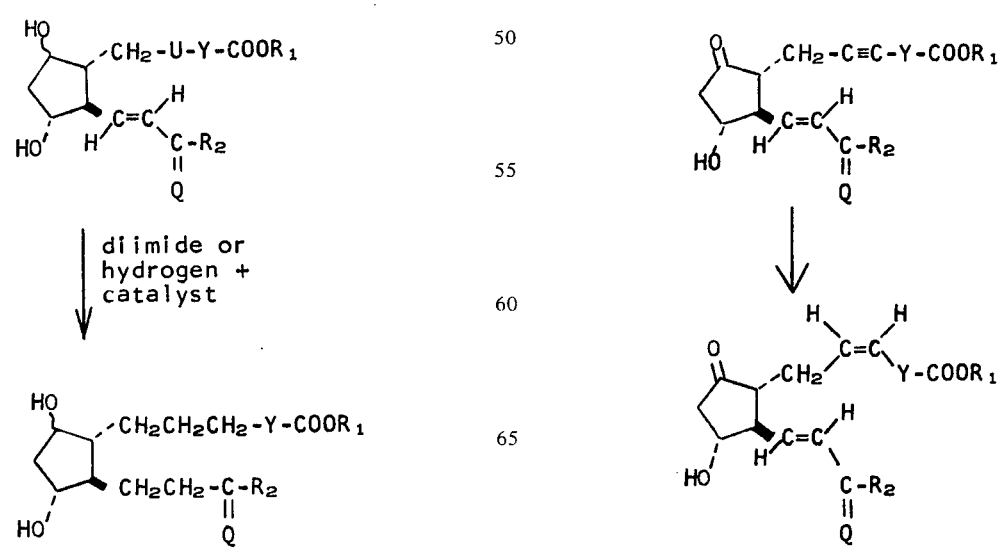

CHART D continued

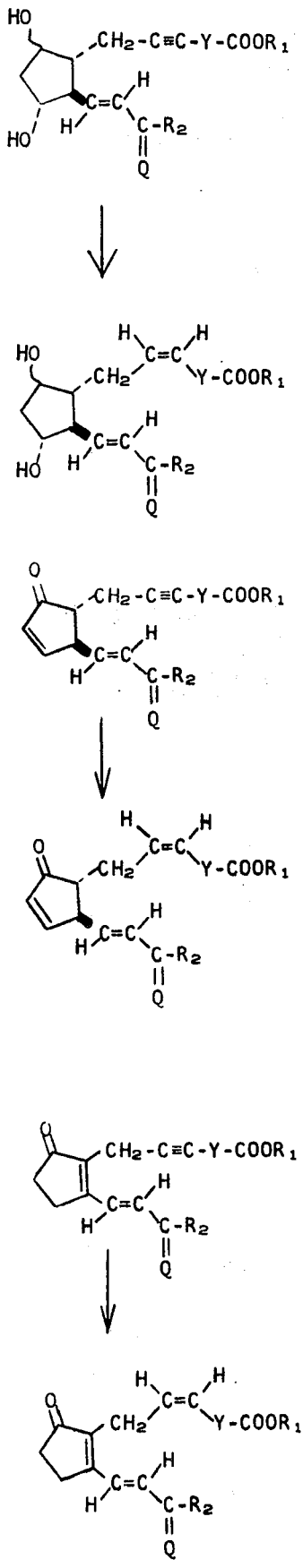

The 3-oxa and 4-oxa PGE type compounds of formulas XVIII to XXIII except wherein $R_1$ is hydrogen, and the 3-oxa and 4-oxa PGA type compounds of formulas XXXVIII to XLIII except wherein $R_1$ is hydrogen are prepared by the series of reactions shown in Chart E, wherein Q, $R_2$, and V are as defined above, $R_{11}$ and $R_{12}$ are alkyl of one to 4 carbon atoms, inclusive $R_{10}$ is the same as the above definition of $R_1$ except that $R_{10}$ does not include hydrogen, $R_{13}$ is alkyl of one to 5 carbon atoms, inclusive, and ~ indicates exo or endo configuration with respect to the moiety attached to the cyclopropane ring.

The 3-oxa and 4-oxa $PGE_1$ type compounds of formulas XVIII and XIX, the 3-oxa and 4-oxa 5,6-dehydro-$PGE_2$ type compounds of formulas XXII and XXIII, the 3-oxa and 4-oxa $PGA_1$ type compounds of formulas XXXVIII and XXXIX, and the 3-oxa and 4-oxa 5,6-dehydro-$PGA_2$ type compounds of formulas XLII and XLIII are also prepared by the series of reactions shown in Chart F, wherein Q, $R_2$, $R_9$, $R_{10}$, and $R_{13}$, are as defined above, Z is $-C_nH_{2n}-O-CR_5R_6-$, $-C_mH_{2m}-O-CR_5R_6-CR_7R_8-$, $-C\equiv C-C_pH_{2p}-O-CR_5R_6-$, or $-C\equiv C-C_qH_{2q}-O-CR_5R_6-CR_7R_8-$, and ~ indicates exo or endo configuration with respect to the moiety attached to the cyclopropane ring.

It should be observed regarding the series of reactions shown in Charts E and F, that the reactions starting with glycol LX in Chart E are similar to the reactions starting with glycol LXVII in Chart F. The only differences here are the definitions of the divalent moieties V (Chart E) and Z (Chart F). V includes saturated, cis and trans ethylenic, and acetylenic divalent moieties. Z is limited to the saturated and acetylenic divalent moieties encompassed by V.

CHART E

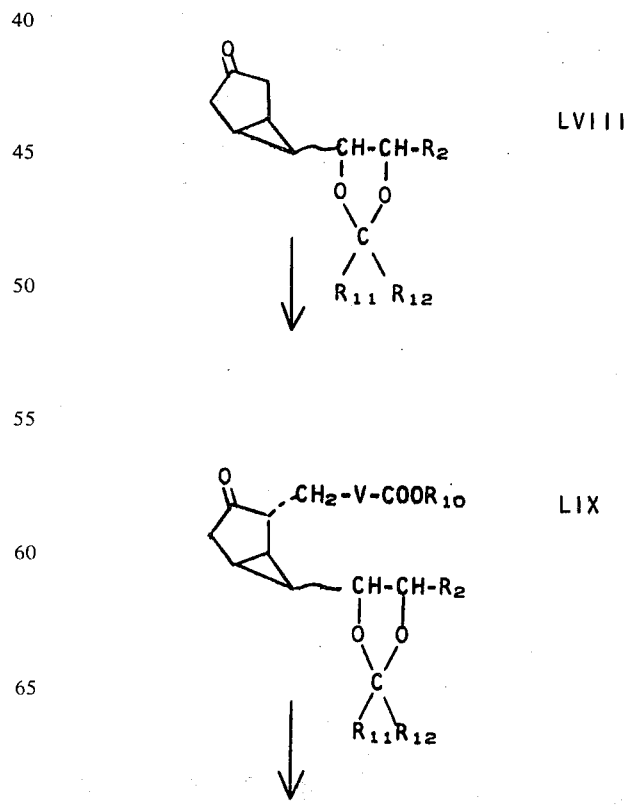

31
CHART E continued
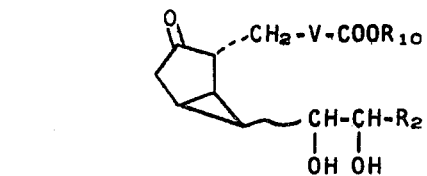 LX
↓
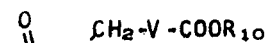 LXI
↓
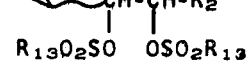 LXII
↓
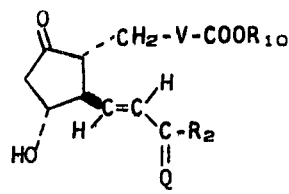 LXIII
↓
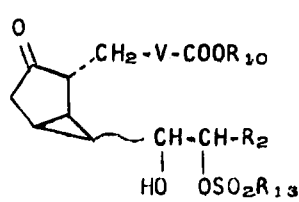 LXIV
32
CHART F
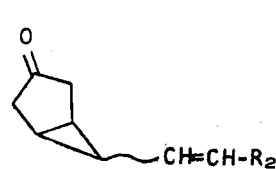 LXV
↓
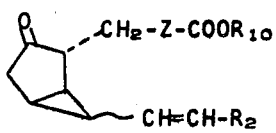 LXVI
↓
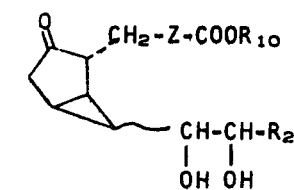 LXVII
↓

CHART F continued

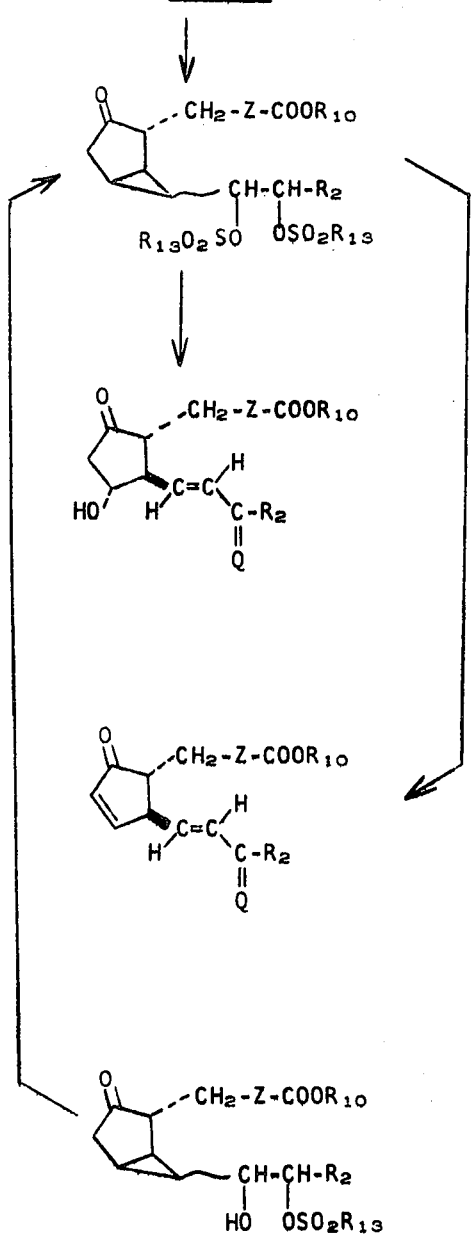

In other words, final 3-oxa and 4-oxa PGE type compounds of formula LXII (Chart E) encompass compounds of formulas XVIII to XXIII. Final 3-oxa and 4-oxa PGA type compounds of formula LXIII (Chart E) encompass compounds of formulas XXXVIII to XLIII. On the other hand, final 3-oxa and 4-oxa PGE type compounds of formula LXIX (Chart F) encompass only compounds of formulas XVIII, XIX, XXII, and XXIII, and final 3-oxa and 4-oxa PGA type compounds of formula LXX (Chart F) encompass only compounds of formulas XXXVIII, XXXIX, XLII, and XLIII.

As will subsequently appear, an acetylenic intermediate of formula LIX, formula LX, or formula LXVII is transformed by reduction to the corresponding cis or trans ethylenic intermediates of formulas LIX or LX, and an acetylenic intermediate of formulas LIX, LX, or LXVII, or a cis or trans ethylenic intermediate of formulas LIX or LX is transformed by reduction to the corresponding saturated intermediate of formulas LIX, LX, or LXVII.

The initial bicyclo-ketone reactant of formula LXV in Chart F is also used as an initial reactant to produce the initial bicyclo-ketone cyclic ketal reactant of formula LVIII in Chart E. The reactions of Chart G will produce cyclic ketal LVIII. Therein THP is tetrahydropyranyl, and $\phi$ is phenyl.

The bicyclo-ketone reactant of formula LXV exists in four isomeric forms, exo and endo with respect to the attachment of the $-CH=CH-R_2$ moiety, and cis and trans with respect to the double bond in that moiety. Each of those isomers separately or various mixtures thereof are used as reactants according to this invention to produce substantially the same final 3-oxa or 4-oxa PGE or PGA type product mixture.

CHART G

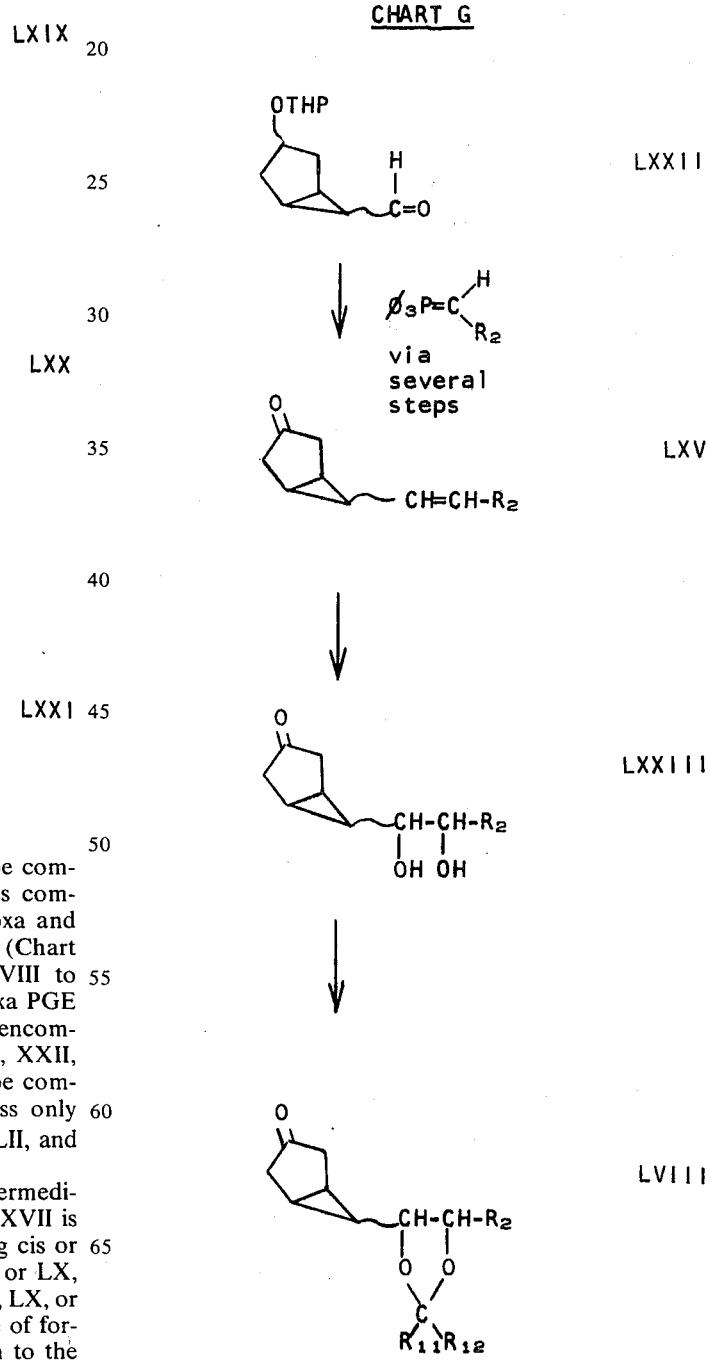

The process for preparing either the exo or endo configuration of the formula-LXV bicyclo-ketone is known to the art. See Belgian Pat. No. 702,477; reprinted in Farmdoc Complete Specifications, Book 714, No. 30.905, page 313, Mar. 12, 1968. See West Germany Offenlegungsschrift No. 1,937,912; reprinted in Farmdoc Complete Specifications, Book No. 14, No. 6869 R, Week $R_5$, Mar. 18, 1970.

In said Belgian Pat. No. 702,477, a reaction sequence capable of forming exo ketone LXV is as follows: The hydroxy of 3-cyclopentenol is protected, for example, with a tetrahydropyranyl group. Then a diazoacetic acid ester is added to the double bond to give an exo-endo mixture of a bicyclo[3.1.0]hexane substituted at 3 with the protected hydroxy and at 6 with a esterified carboxyl. The exo-endo mixture is treated with a base to isomerize the endo isomer in the mixture to more of the exo isomer. Next, the carboxylate ester group at 6 is transformed to an aldehyde group, —CHO. Then, said aldehyde group is transformed by the Wittig reaction, in this case to a moiety of the formula $-CH=CH-R_2$ which is in exo configuration relative to the bicyclo ring structure. Next, the protective group is removed to regenerate the 3-hydroxy which is then oxidized, for example, by the Jones reagent, i.e., chromic acid (see J. Chem. Soc. 39 (1946)), to give said exo ketone LXV.

Separation of the cis-exo and trans-exo isomers of LXV is described in said Belgian Pat. No. 702,477. However, as mentioned above, that separation is usually not necessary since the cis-trans mixture is useful as a reactant in the next process step.

The process described in said Belgian Pat. No. 702,477 producing the exo form of bicyclo-ketone LXV uses, as an intermediate, the exo form of a bicyclo [3.1.0]hexane substituted at 3 with a protected hydroxy, e.g., tetrahydropranyloxy, and at 6 with an esterified carboxyl. When the corresponding endo compound is substituted for that exo intermediate, the process in said Offenlegungsschrift No. 1,937,912 leads to the endo form of bicyclo-ketone LXV. That endo compound to be used has the formula:

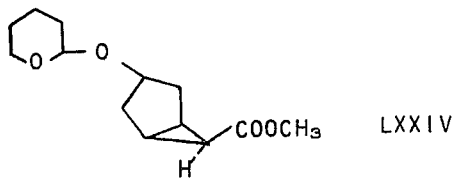

LXXIV

Compound LXXIV is prepared by reacting endo-bicyclo[3.1.0]-hexane-3-ol-6-carboxylic acid methyl ester which is then reacted with dihydropyran in the presence of a catalytic amount of $POCl_3$ to give the desired compound. This is then used as described in said Offenlegungsschrift No. 1,937,912 to produce the endo form of bicyclo-ketone LXV.

As for exo LXV, the above process produces a mixture of endo-cis and endo-trans compounds. These are separated as described for the separation of exo-cis and exo-trans LXV, but this separation is usually not necessary since, as mentioned above, the cis-trans mixture is useful as a reactant in the next process step.

In the processes of said Belgian patent and said Offenlegungsschrift, certain organic halides, e.g., chlorides and bromides, are necessary to prepare the Wittig reagents used to generate the generic moiety, $-CH=CH-R_2$ of bicyclo-ketone LXV. These organic chlorides and bromides $R_2-CH_2-Cl$ and $R_2-CH_2-Br$, are known in the art or can be prepared by methods known in the art.

To illustrate the availability of these organic chlorides consider first the above-described 3-oxa and 4-oxa PGE-type compounds of formulas XVIII to XXVII wherein G is alkyl of one to 10 carbon atoms, inclusive, substituted with zero, one, 2, or 3 fluoro.

For those products wherein $R_2$ is alkyl of one to 10 carbon atoms, substituted with zero to 3 fluoro atoms, there are available the monohalo hydrocarbons, e.g., bromo(or chloro-)methane, -ethane, -propane, -pentane, -octane, and -decane; and the monohalofluorohydrocarbons, e.g., $CH_2FCl$, $CH_2FCH_2Br$, $CHF_2CH_2Cl$, $CF_3CH_2Br$, $F(CH_2)_3Br$, $CH_3CF_2CH_2Cl$, $CF_3(CH_2)_2Br$, $F(CH_2)_4Cl$, $CH_3CF_2CH_2CH_2Cl$, $C_4H_9CFHCH_2Br$, $CF_3(CH_2)_3Cl$, $CF(CH_2)_2BrCH_3$, $CH_2F(CH_2)_4Cl$, $C_2H_5CF_2(CH_2)_2Cl$, $CF_3(CH_2)_4Cl$, $CH_3(CH_2)_4CF_2(CH_2)_2CH_2Cl$, and $CH_3(CH_2)_3CF_2(CH_2)_3CH_2Cl$, as described in "Aliphatic Fluorine Compounds", A. M. Lovelace et al., Am. Chem. Soc. Monograph Series 1958, Reinhold Publ. Corp. Those halides not available are prepared by methods known in the art by reacting the corresponding primery alcohol $R_2-CH_2OH$ with $PCl_3$, $PBr_3$, or any of the other halogenating agents useful for this purpose. Available alcohols include $CH_3CH(CF_3)CH_2OH$, $(CH_3)_2CHCH_2CH_2OH$, $(CH_3)_3CCH_2OH$, $CF_3CH(CH_3)CH_2CH_2OH$, for example. For those halides of the formula $R_2-CH_2-Hal$ wherein Hal is chloro or bromo $R_2$ is $R_{14}(CH_2)_d$, $d$ being 1, 2, 3, or 4, and $R_{14}$ being isobutyl, tert-butyl, 3,3-difluorobutyl, 4,4-difluorobutyl, or 4,4,4-trifluorobutyl, the intermediate alcohols are prepared as follows.

In the case of $R_{14}$ being isobutyl or tert-butyl, known alcohols are converted to bromides, thence to nitriles with sodium cyanide, thence to the corresponding carboxylic acids by hydrolysis, and thence to the corresponding primary alcohols by reduction, e.g. with lithium aluminum hydride, thus extending the carbon chain one carbon atom at a time until all primary alcohols are prepared.

In the case of $R_{14}$ being 3,3-difluorobutyl, the necessary alcohols are prepared from keto carboxylic acids of the formula, $CH_3-CO-(CH_2)_r-COOH$, wherein $r$ is 2, 3, 4, 5, or 6. All of those acids are known. The methyl esters are prepared and reacted with sulfur tetrafluoride to produce the corresponding $CH_3-CF_2-(CH_2)_r-COOCH_3$ compounds, which are then reduced with lithium aluminum hydride to $CH_3-CF_2-(CH_2)_r-CH_2OH$. These alcohols are then transformed to the bromide or chloride by reaction with $PBr_3$ or $PCl_3$.

In the case of $R_{14}$ being 4,4-difluorobutyl, the initial reactants are the known dicarboxylic acids, HOO- C—$(CH_2)_f$—COOH, wherein $f$ is 3, 4, 5, 6, or 7. These dicarboxylic acids are esterified to $CH_3OOC$—$(CH_2)_f$—$COOCH_3$ and then half-saponified, for example with barium hydroxide, to give HOOC—$(CH_2)_f$—$COOCH_3$. The free carboxyl group is transformed first to the acid chloride with thionyl chloride and then to an aldehyde by the Rosenmund reduction. Reaction of the aldehyde with sulfur tetrafluoride then gives $CHF_2$—$(CH_2)_f$—$COOCH_3$ which by successive treatment with lithium aluminum hydride and $PB_{r3}$ or $PCl_3$ gives the necessary bromides or chlorides, $CHF_2$—$(CH_2)_f$—$CH_2Br$ or $CHF_2$—$(CH_2)_f$—$CH_2Cl$.

In the case of $R_{14}$ being 4,4,4-trifluorobutyl, aldehydes of the formula $CH_3OOC$—$(CH_2)_f$—CHO are prepared as described above. Reduction of the aldehyde with sodium borohydride gives the alcohol $CH_3OOC$—$(CH_2)_f$—$CH_2OH$. Reaction with a hydrogen halide, for example hydrogen bromide, gives the corresponding halocarboxylic acid which by reaction with sulfur tetrafluoride gives the necessary $CF_3$—$(CH_2)_f$—$CH_2$—Br or $CF_3$—$(CH_2)_f$—$CH_2$—Cl.

For the above reactions of $SF_4$, see U.S. Pat. No. 3,211,723 and J. Org. Chem. 27, 3164 (1962).

As mentioned above, formula XVIII-to-LVII compounds with an alpha-fluoro substituent in a straight chain 3 to 7-carbon $R_2$, i.e., $R_2$ being —CHF—$(CH_2)_g$—$CH_3$ wherein $g$ is 1, 2, 3, 4, or 5, represent preferred embodiments among the novel 3-oxa and 4-oxa compounds of this invention. Among those, for example, is 3-oxa-16-fluoro-$PGE_1$. The formula-LXV bicycloketones necessary to produce those monofluoro compounds are advantageously prepared by reacting either of the above-mentioned bicyclo-aldehydes, exo or endo, with a Wittig reagent prepared from $CH_3$—$(CH_2)_g$—CO—$CH_2$—Br and triphenylphosphine. The aldehyde group is thereby transformed to

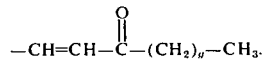

The resulting unsaturated ketone is reduced to the corresponding

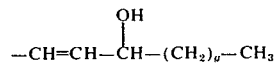

compound. Then —OH in that group is replaced with fluoro by known methods, for example, directly by reaction with 2-chloro1,1,1-trifluorotriethylamine or indirectly, for example, by transforming the hydroxy to tosyloxy or mesyloxy, and reacting the resulting compound with anhydrous potassium fluoride in diethylene glycol.

The transformation of bicyclo-ketone-olefin LXV to glycol LXXIII is carried out by reacting olefin LXV with a hydroxylation reagent. Hydroxylation reagents and procedures for this purpose are known in the art. See, for example, Gunstone, Advances in Organic Chemistry, Vol. 1, pp. 103–147, Interscience Publishers, New York, N.Y. (1960). Especially useful hydroxylation reagents for this purpose are osmium tetroxide and performic acid (formic acid plus hydrogen peroxide). Variosu isomeric glycols are obtained depending on such factors as whether olefin LXV is cis or trans and endo or exo, and whether a cis or a trans hydroxylation reagent is used. These various glycol mixtures can be separated into individual isomers by silica gel chromatography. However, this separation is usually not necessary, since all isomers of a particular glycol are equally useful as intermediates according to this invention and the processes outlined in Chart E to produce final products of formulas LXII and LXIII, and then, according to Chart A, B, C, and D to produce the other final products of this invention.

The transformation of glycol LXXIII to the cyclic ketal of formula LVIII (Chart E) is carried out by reacting said glycol with a dialkyl ketone of the formula

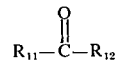

wherein $R_{11}$ and $R_{12}$ are alkyl of one to 4 carbon atoms, inclusive, in the presence of an acid catalyst, for example potassium bisulfate or 70% aqueous perchloric acid. A large excess of the ketone and the absence of water is desirable for this reaction. Examples of suitable dialkyl ketones are acetone, methyl ethyl ketone, diethyl ketone, methyl propyl ketone, and the like. Acetone is preferred as a reactant in this process.

Referring again to Chart E, cyclic ketal LVIII is transformed to cyclic ketal LIX by alkylating with an alkylation agent of the formula Hal—$CH_2$—V—$COOR_{10}$ wherein $R_{10}$ and V are as defined above, and Hal is chlorine, bromine, or iodine. Similarly, referring to Chart F, olefin LXV is transformed to olefin LXVI by alkylating with an alkylation agent of the formula Hal—$CH_2$—Z—$COOR_{10}$ wherein $R_{10}$, Z, and Hal are as defined above.

Any of the alkylation procedures known in the art to be useful for alkylating cyclic ketones with alkyl halides and haloalkanoic esters are used for the transformations of LVIII to LIX and LXV to LXVI. See, for example, the abovementioned Belgian Pat. No. 702,477 for procedures useful here and used there to carry out similar alkylations, e.g., employing the bicyclo enamines.

For these alkylations, it is preferred that Hal be bromo or iodo. Any of the usual alkylation bases, e.g., alkali metal alkoxides, alkali metal amides, and alkali metal hydrides, are useful for this alkylation. Alkali metal alkoxides are preferred, especially tert-alkoxides. Sodium and potassium are preferred alkali metals. Especially preferred is potassium tert-butoxide. Preferred diluents for this alkylation are tetrahydrofuran and 1,2-dimethoxyethane. otherwise, procedures for producing and isolating the desired formula LIX and LXVI compounds are within the skill of the art.

These alkylation procedures produce mixtures of alpha and beta alkylation products, i.e., a mixture of the formula-LIX products wherein the —$CH_2$—V—$COOR_{10}$ moiety is attached in alpha configuration, with corresponding compounds having that moiety attached in beta configuration, or a mixture of the formula-LXVI products with corresponding compounds having the —$CH_2$—Z—$COOR_{10}$ moiety in the beta configuration. When about one equivalent of base per equivalent of formula LXV or LVIII ketone is used, the alpha configuration usually predominates. Use of an excess of base and longer reaction times usually result in production of larger amounts of beta products. These alphabeta isomer mixtures are separated at this stage or at any subsequent stage in the multi-step processes shown in Charts E and F. Silica gel chromatography is preferred for this separation.

The necessary alkylating agents for the above-described alkylations, i.e., compounds of the formulas $Hal-CH_2-V-COOR_{10}$ and $Hal-CH_2-Z-COOR_{10}$, are prepared by methods known in the art.

There are eight groups of compounds encompassed by these two genera of alkylating agents. Alkylating agents of the formula $Hal-CH_2-Z-COOR_{10}$ include compounds of the following formulas:

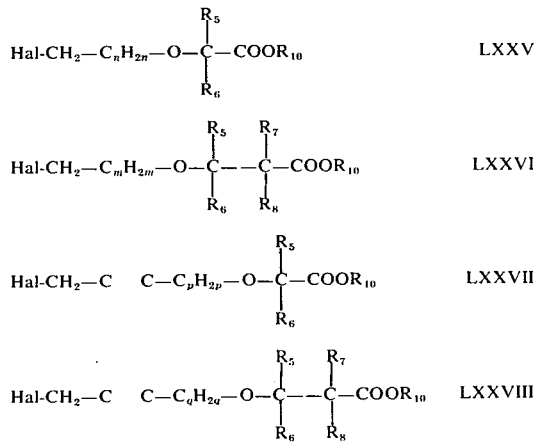

Alkylating agents of the formula $Hal-CH_2-V-COOR_{10}$ include the above-listed compounds of formulas LXXV, LXXVI, LXXVII, and LXXVIII, and also compounds of the following formulas:

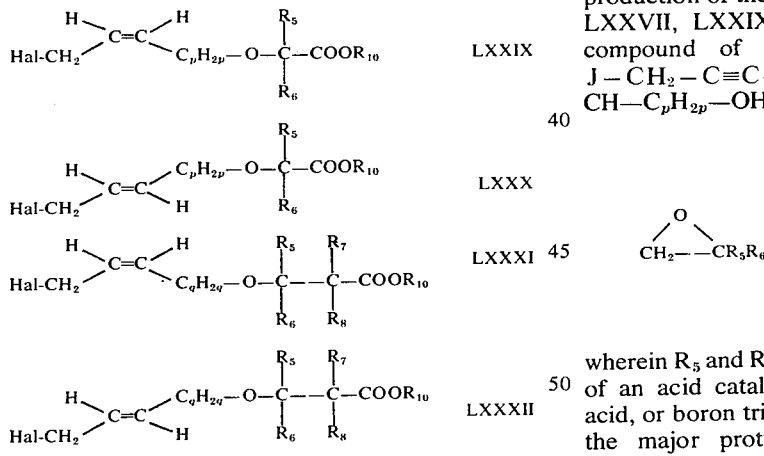

These alkylating agents of formulas LXXV to LXXXII are accessible to those of ordinary skill in the art. For example, the 3-oxa alkylating agents of formulas LXXV, LXXVII, LXXIX, and LXXX are advantageously prepared by reacting an alpha-hydroxy ester or acid of the formula $HO-CR_5R_6-COOR_1$, wherein $R_1$, $R_5$, and $R_6$ are as defined above, with a compound of the formula, $J-CH_2-C_nH_{2n}-G$, $J-CH_2-C \equiv C-C_pH_{2p}-G$, and $J-CH_2-CH=CH-C_pH_{2p}-G$, respectively, wherein $C_nH_{2n}$ and $C_pH_{2p}$ are as defined above, J is chloro, bromo, iodo, or a group transformable to one of those, for example, tetrahydropyranyloxy or mesyloxy, and G is chloro, bromo, iodo, mesyloxy, tosyloxy, or the like, in the presence of a strong base, for example, sodium hydride when $R_1$ is a carbon-containing group, and lithium diisopropyl amide when $R_1$ is hydrogen. Alternatively, an alpha-bromo ester or acid of the formula $Br-CR_5R_6-COOR_1$, wherein $R_1$, $R_5$, and $R_6$ are as defined above, is reacted in the presence of a similar strong base with a compound of the formula $J-CH_2-C_nH_{2n}-OH$, $J-CH_2-C \equiv C-C_pH_{2p}-OH$, or $J-CH_2-CH=CH-C_pH_{2p}-OH$. When both $R_5$ and $R_6$ in the ester are alkyl, it is preferred to use the hydroxy acid or ester route. When there are two alkyl groups in $C_nH_{2n}$ or $C_pH_{2p}$ on the carbon to which —OH or —G is attached, it is preferred to use the bromo acid or ester route. When a formula LXXV, LXXVII, LXXIX, or LXXX alkylating agent is desired wherein both $R_5$ and $R_6$ are alkyl and $C_nH_{2n}$ or $C_pH_{2p}$ has two alkyl groups attached to the carbon to which —O— is attached, it is preferred that G be mesyloxy or tosyloxy, or that the Br of the bromo acid or ester be replaced with mesyloxy or tosyloxy, whereupon bases and reaction conditions known in the art may be used, for example, potassium tert-butoxide in dimethyl sulfoxide. Alternatively, this group of tetraalkyl compounds is advantageously prepared by using the hydroxy acid or ester route with a compound wherein G is chloro, or by using the bromo acid or ester route wherein the bromo is replaced with chloro, using freshly precipitated wet magnesium hydroxide in an inert solvent suspension as the base. Alternatively this group of tetraalkyl compounds is advantageously prepared by the hydroxy acid or ester route wherein G is iodo, and silver oxide is used as the base. Any of these alternative routes is, of course, useful to make the other compounds within the scope of formulas LXXV, LXXVII, LXXIX, and LXXX.

An alternative procedure generally applicable to the production of the alkylating agents of formulas LXXV, LXXVII, LXXIX, and LXXX comprises reacting a compound of the formula $J-CH_2-C_nH_{2n}-OH$, $J-CH_2-C \equiv C-C_pH_{2p}-OH$, or $J-CH_2-CH=CH-C_pH_{2p}-OH$ with an ethylene oxide of the formula

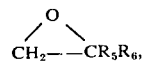

wherein $R_5$ and $R_6$ are as defined above, in the presence of an acid catalyst, e.g., hydrochloric acid, sulfuric acid, or boron trifluoride. The alcohol which is usually the major protuct, i.e., $J-CH_2-C_nH_{2n}-O-CR_5R_6-CH_2OH$, $J-CH_2-C \equiv C-C_pH_{2p}-O-CR_5R_6-CH_2OH$, or cis or trans $J-CH_2-CH=CH-C_pH_{2p}-O-CR_5R_6-CH_2OH$, is isolated, oxidized to the corresponding carboxylic acid with Jones reagent, and the acid esterified ($R_{10}$).

The 4-oxa alkylating agents of formulas LXXVI, LXXVIII, LXXXI, and LXXXII are advantageously prepared as described above for the 3-oxa compounds, combining compounds of the formula $J-CH_2-C_mH_{2m}-G$, $J-CH_2-C_mH_{2m}-OH$, $J-CH_2-C \equiv C-C_qH_{2q}-G$, $J-CH_2-C \equiv C-C_qH_{2q}-OH$, $J-CH_2-CH=CH-C_qH_{2q}-G$, and $J-CH_2-CH=CH-C_qH_{2q}-OH$, with β-hydroxy acids or esters and β-halo acids or esters of the formulas $HO-CR_5R_6-CR_7R_8-COOR_1$ and $Br-CR_5R_6-CR_7R_8-COOR_1$, or trimethylene oxides of the formula

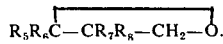

All of the procedures, preferences, and alternatives described above for the preparation of the 3-oxa alkylating agents are applicable to the preparation of these 4-oxa alkylating agents.

The alkylating agents of formulas LXXV to LXXXII are esters. When an alpha or beta hydroxy acid or bromo acid is used as a reactant as described above, the resulting product is a carboxylic acid. This acid is esterified to the corresponding formulas LXXV-to-LXXXII alkylating agent by known procedures. As will be described hereinafter, the ester moiety $R_{10}$ is chosen according to the desired type of final 3-oxa or 4-oxa prostaglandin-like product.

The alpha-hydroxy, alpha-halo, beta-hydroxy, and beta-halo acids and esters and the ethylene and trimethylene oxides used as described above to produce the formula LXXV to LXXXII alkylating agents are all known in the art or are readily accessible through known methods to those of ordinary skill in the art.

The other reactants of the formulas $J—CH_2—C_nH_{2n}—OH$, $J—CH_2—C_mH_{2m}—OH$, $J—CH_2—C≡C—C_pH_{2p}—OH$, $J—CH_2—CH=CH—C_pH_{2p}—OH$, $J—CH_2—C≡C—C_qH_{2q}—OH$, $J—CH_2—CH=CH—C_qH_{2q}—OH$, and the corresponding reactants with halogen, mesyloxy, or tosyloxy in place of —OH also are known in the art or are readily accessible through known methods to those of ordinary skill in the art.

For example, consider the compounds

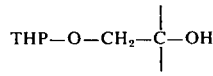

wherein THP represents 2-tetrahydropyranyl, and each free valence— is attached to hydrogen or to alkyl, with a total of zero to 9 attached alkyl carbon atoms. Said compounds are within the scope of $J—CH_2—C_nH_{2n}—OH$ as above defined, and are advantageously prepared by hydroxylating by known methods, olefins of the formula

to give the glycols

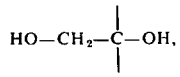

which are transformed by known methods to the above tetrahydropyranyl ethers. These ethers are also transformed by known methods to

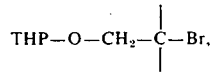

compounds within the scope of $J—CH_2—C_nH_{2n}—G$ as above defined.

Consider the compounds

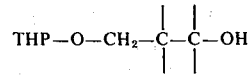

wherein THP is as above defined, and the free valences are attached to hydrogen or to alkyl, with a total of zero to 8 attached alkyl carbon atoms. Said compounds are within the scope of $J—CH_2—C_nH_{2n}—OH$ as above defined, and are advantageously prepared by known methods from beta-hydroxyesters of the formula

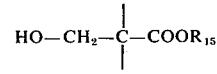

wherein $R_{15}$ is methyl or ethyl and the free valences are attached to hydrogen or to alkyl. Said esters are available through methods known in the art, e.g., the Reformatsky reaction. Said compounds are also transformed by known methods to

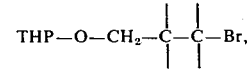

compounds within the scope of $J—CH_2—C_nH_{2n}—G$ as above defined.

Consider the compounds

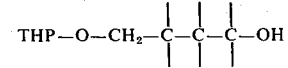

wherein THP is as defined above and the free valences are attached to hydrogen or to alkyl, with a total of zero to 7 attached alkyl carbon atoms. Said compounds are within the scope of $J—CH_2—C_nH_{2n}—OH$ as above defined, and are advantageously prepared by known methods from the known succinic acid half esters of the formula

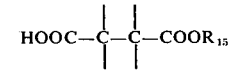

wherein $R_{15}$ is methyl or ethyl, the carboxyl end being transformed to $THP—O—CH_2—$, and then the —$COOR_{15}$ end being transformed to

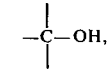

both by known methods. Said compounds are also transformed by known methods to

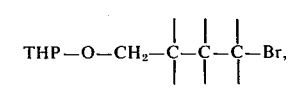

compounds within the scope of $J—CH_2—C_nH_{2n}—G$ as above defined.

Consider the compounds

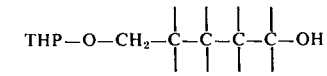

wherein THP is as defined above and the free valences are attached to hydrogen or to alkyl, with a total of zero to 6 attached alkyl carbon atoms. Said compounds are within the scope of J—CH$_2$—C$_n$H$_{2n}$—OH as above defined, and are advantageously prepared by known methods from

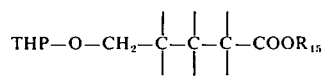

wherein THP and the free valence attachments are as above defined, and R$_{15}$ is methyl or ethyl. These ester reactants are prepared by known methods from

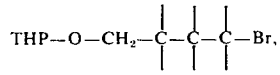

reactants whose preparation is described in the proceeding paragraph. Said compounds are also transformed by known methods to

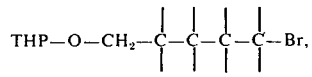

compounds within the scope of J—CH$_2$—C$_n$H$_{2n}$—G as above defined. In a similar manner, compounds of the formulas

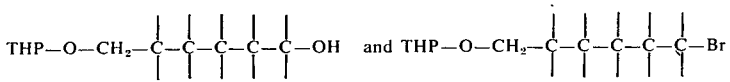

wherein the free valences are attached to hydrogen or to alkyl, with a total of zero to 5 attached alkyl carbon atoms, are prepared from

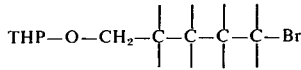

compounds.

Consider the compounds

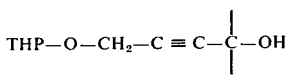

wherein THP is as above defined, and the free valences are attached to hydrogen or to alkyl, with a total of zero to seven attached alkyl carbon atoms. Said compounds are within the scope of of J—CH$_2$—C ≡ C—C$_p$H$_{2p}$—OH, as above defined, and are prepared by known methods from reactants of the formula

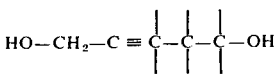

which are known in the art or are prepared by known methods. See, for example, U.S. Pat. No. 3,108,140. Said compounds are also transformed by known methods to

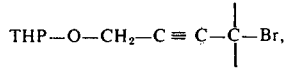

compounds within the scope of J—CH$_2$—C ≡ C—C$_p$H$_{2p}$—G as above defined.

Consider the compounds

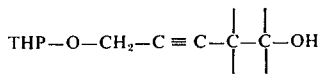

wherein THP is as above defined, and the free valences are attached to hydrogen or to alkyl, with a total of zero to six attached alkyl carbon atoms. Said compounds are within the scope of J—CH$_2$—C ≡ C—C$_p$H$_{2p}$—OH, as above defined, and are prepared by known methods form the known or easily accessible beta-hydroxy esters of the formula

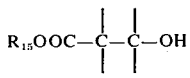

wherein R$_{15}$ is methyl or ethyl. The hydroxy end of those is changed to —O—THP and the R$_{15}$OOC—end is changed to

both by known methods. Then

is changed by known methods first to HC ≡ C— and then to HO—CHH$_2$—C ≡ C—. Finally

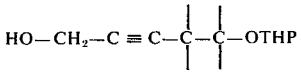

is transformed by known methods to

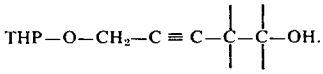

The latter is also transformed by known methods to THP—O—CH$_2$—C ≡ C—C—C—Br, compounds within the scope of J—CH$_2$—C ≡ C—C$_p$H$_{2p}$—G as above defined.

Another route to compounds

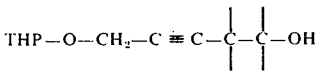

as above defined comprises Reformatsky-type reactions to propargyl bromides of the formula

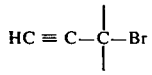

with ketones or aldehydes

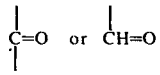

to give

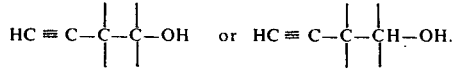

See, for example, J. Chem. Soc. (London) 2696 (1949). Then —OH is changed to —O—THP and HC ≡ C— is changed to HO—CH$_2$—C ≡ C—, both by known methods. Finally,

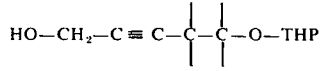

is changed to

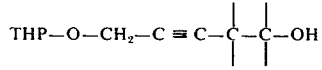

by known methods.

Consider the compounds

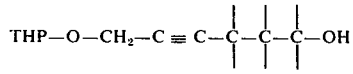

wherein THP is as above-defined, and the free valences are attached to hydrogen or to alkyl, with a total of zero to 5 attached alkyl carbon atoms. Said compounds are within the scope of J—CH$_2$—C ≡ C—C$_p$H$_{2p}$—OH as above defined, and are prepared by known methods from the known succinic acid half esters of the formula

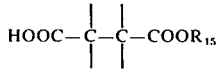

wherein R$_{15}$ is methyl or ethyl. The carboxyl end is changed to Br— and the -COOR$_{15}$ end is changed to

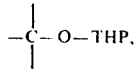

both by known methods. Then, BR- is changed first to HOOC- and then to

both by known methods. Then

is changed first to HC ≡ C- and then to HO-CH$_3$-C ≡ C-, both by known methods. Finally,

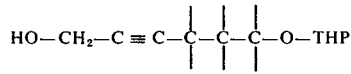

is transformed by known methods to

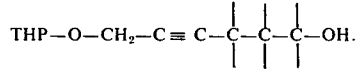

The latter is also transformed by known methods to

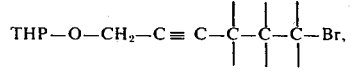

compounds within the scope of J-CH$_2$-C ≡ C-C$_p$H$_{2p}$-G as above defined.

Another route to compounds of the formulas

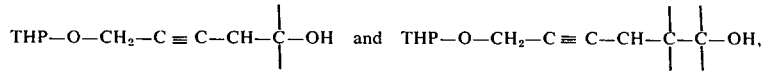

both types within the scope of J-CH$_2$-C ≡ C-C$_p$H$_{2p}$-OH as above defined comprises reaction of

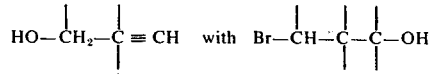

by known procedures. These latter reactants are known or easily accessible by known methods.

The reactants of formulas J-CH$_2$-C$_m$H$_{2m}$-OH and J-CH$_2$-C$_m$H$_{2m}$-G are prepared as described above for the preparation of the corresponding C$_n$H$_{2n}$ compounds, due consideration being given to the definition differences between CnH$_{2n}$ and CmH$_{2m}$. Similarly, reactants of formulas J-CH$_2$-C ≡ C-CqH$_{2q}$-OH and J-CH$_2$-C ≡ C-CqH$_{2q}$-G are prepared as described above for the preparation of the corresponding C$_p$H$_{2p}$ compounds, due consideration being given to the definition differences between C$_p$H$_{2p}$ and CqH$_{2q}$.

The cis and trans ethylenic reactants of formulas J-CH$_2$-CH=CH-C$_p$H$_{2p}$-OH, J-CH$_2$-CH=CH-C$_p$H$_{2p}$-G, J-CH$_2$-CH=CH-CqH$_{2q}$-OH, and J-CH$_2$-CH=CH-CqH$_{2q}$-G are prepared by cis or trans reduction of the corresponding acetylenic reactant prepared as above described, or by cis or trans reduction of any earlier acetylenic intermediate in which both ends of the acetylenic bond are substituted, i.e., not hydrogen as in the moiety HC ≡ C-. Alternatively, this cis or trans reduction is carried out on any subsequent acetylenic reaction product leading up to and including the final acetylenic alkylating agent of formula LXXVII or LXXVIII.

For these cis reductions of the acetylenic bonds, it is advantageous to use hydrogen plus a catalyst which catalyzes hydrogenation of -C ≡ C- only to cis-CH=CH-. Such catalysts and procedures are well known to the art. See, for example, Fieser et al., "Reagents for Organic Synthesis", pp. 566–567; John Wiley & Sons, Inc., New York, N.Y. (1967). Palladium (5%) on barium sulfate, especially in the presence of pyridine as a diluent, is a suitable catalyst for this purpose. Alternative reagents useful to transform these acetylenic compounds to cis-ethylenic compounds are bis-3-methyl-2-butylborane ("disiamylborane") and diisobutylaluminum hydride.

For trans reductions of the acetylenic bond, except for those compounds containing halogen, it is advantageous to use sodium or lithium in liquid ammonia or a liqiud alkylamine, e.g., ethylamine. When the moiety HO-CH$_2$-C ≡ C- is present in the acetylenic compound being reduced, the use of lithium aluminum hydride gives trans reduction of the triple bond. Procedures for these trans reductions are known in the art. See, for example, Fieser et al., above cited, pp. 577, 592–594, and 603, and J. Am. Chem. Soc. 85, 622 (1963).

Referring again to Chart E, after alkylation as discussed above, cyclic ketal LIX is transformed to glycol LX by reacting the cyclic ketal with an acid with pK less than 5. Suitable acids and procedures for hydrolyzing cyclic ketals to glycols are known in the art. Suitable acids are formic acid, hydrochloric acid, and boric acid. Especially preferred as diluents for this reaction are tetrahydrofuran and β-methoxyethanol.

Referring again to Chart F, after alkylation as discussed above, olefin LXVI is hydroxylated to glycol LXVII. As discussed above, the divalent moiety -Z- includes the moieties -C$_n$H$_{2n}$-O-CR$_5$R$_6$-, C$_m$H$_{2m}$-O-CR$_5$R$_6$-CR$_7$R$_8$-, wherein -C ≡ C-C$_p$H$_{2p}$-O-CR$_5$R$_6$-, and -C ≡ C-C$_q$H$_{2q}$-O-CR$_5$R$_6$-CR$_7$R$_8$-, wherein Cm$_2$m,C$_n$H$_{2n}$, C$_p$H$_{2p}$, C$_q$H$_{2q}$, R$_6$, R$_7$, and R$_8$are as defined above. When Z is -C$_n$H$_{2n}$-O-CR$_5$R$_6$- or -C$_m$H$_{2m}$-O-CR$_5$R$_6$-CR$_7$R$_8$-, this hydroxylation of LXVI is carried out as described above for the hydroxylation of olefin LXV to glycol LXXIII, i.e., with any of the known reagents and procedures described in Gunstone, above cited. When Z is -C ≡ C-C$_p$H$_{2p}$-O-CR$_5$R$_6$- or -C ≡ C-C$_q$H$_{2q}$-O-CR$_5$R$_6$-CR$_7$R$_8$-, some of the reagents and procedures described by Gunstone tend to attack the acetylenic linkage as well as the ethylenic linkage of the formula LXVI olefin. Therefore it is preferred to use a hydroxylation reagent and procedure which attacks the ethylenic linkage preferentially. For this, it is preferred to carry out hydroxylation of these acetylenic formula LXVI olefins with organic peracids, e.g., performic acid, peracetic acid, perbenzoic acid, or m-chloroperbenzoic acid, as described by Gunstone, above cited, pp. 124–130.

As discussed above regarding the hydroxylation of unalkylated olefin LXV to unalkylated glycol LXXIII, various isomeric glycols are obtained by hydroxylation of the formula LXVI alkylated olefin. The particular formula- LXVII glycol or glycol mixture obtained depends on such factors as whether the olefin LXVI is cis or trans and endo or exo, and whether a cis or a trans hydroxylation takes place. However, all of the isomeric formula-LXVI erytho and threo glycols and the various glycol mixtures each are useful as an intermediate according to this invention and the processes of Chart F to produce final products of formulas LXIX and LXX, and then according to Charts, A, B, C, and D, to produce the other final products of this invention. Therefore, it is usually not necessary to separate individual formula-LXVI glycol isomers before proceeding further in the synthesis, although that separation is accomplsihed by silica gel chromatography.

Referring again to Charts E and F, bis-alkanesulfonic acid esters LXI and LXVIII are prepared by reacting glycols LX and LXVII, respectively, with an alkanesulfonyl chloride or bromide, or with an alkanesulfonic acid anhydride, the alkyl in each containing one to 5 carbon atoms, inclusive. Alkanesulfonyl chlorides are preferred for this reaction. The reaction is carried out in the presence of a base to neutralize the byproduct acid. Expecially suitable bases are tertiary amines, e.g., dimethylaniline or pyridine. It is usually sufficient merely to mix the two reactants and the base, and maintain the mixture in the range 0° to 25°C. for several hours. The formula LXI and LXVIII bis-sulfonic acid esters are then isolated by procedures known to the art.

Referring now to Chart E, bis-sulfonic acid esters LXI are transformed either to 3-oxa or 4-oxa PGE-type compounds LXII, or to 3-oxa or 4-oxa PGA-type compounds LXIII. Referring to Chart F, bis-sulfonic acid esters LXVIII are transformed either to 3-oxa or 4-oxa PGE type compounds LXIX, or to 3-oxa or 4-oxa PGA type compounds LXX.

The transformations of LXI and LXVIII to the PGE type compounds LXII and LXIX respectively, are carried out by reacting bis-esters LXI and LXVIII with water in the range about 0° to about 60° C. In making 3-oxa-PGE$_1$ or 4-oxa-PGE$_1$, 25° C. is a suitable reaction temperature, the reaction then proceeding to completion in about 5 to 20 hours. It is advantageous to have a homogenous reaction mixture. This is accomplished by adding sufficient of a water-soluble organic diluent which does not enter into the reaction. Acetone is a suitable diluent. The desired product is isolated by evaporation of excess water and diluent if one is used. The residue contains a mixture of formula LXII or formula LXIX C-15 epimers which differ in the configuration of the side chain hydroxy, that being either "natural" (α) or "epi" (β). These are separated from byproducts and from each other by silica gel chromatography. A usual byproduct is the mono-sulfonic acid ester of formula LXIV (Chart E) or formula LXXI (Chart F). These mono-sulfonic acid esters are esterified to the formula LXI or LXVIII bis-sulfonic acid esters, respectively, in the same manner described above for the transformation of glycol LX or LXVII to bis-ester LXI or LXVIII and thus are recycled back to additional formula LXII or LXIX final product.

The transformations of LXI and LXVIII to the PGA type compounds LXIII and LXX, respectively, are carried out by heating bis-esters LXI and LXVIII in the range 40° to 100° C. with a combination of water, a base characterized by its water solution having a pH 8 to 12, and sufficient inert water-soluble organic diluent to form a basic and substantially homogenous reaction mixture. A reaction time of one to 10 hours is usually used. Preferred bases are the water-soluble salts of carbonic acid, especially alkali metal bicarbonates, e.g., sodium bicarbonate. A suitable diluent is acetone. The products are isolated and separated as described above for the transformation of bis-esters LXI and LXVIII to PGE type products LXII and LXIX. The same mono-sulfonic acid esters LXIV and LXXI observed as byproducts in those tranformations are also observed during preparation of PGA type products LXIII and LXX.

For the transformations of bis-sulfonic acid esters LXI and LXVIII to final products LXII, LXIII, LXIX, and LXX, it is preferred to use the bis-mesyl esters, i.e., compouonds LXI and LXVIII wherein $R_{13}$ is methyl.

Referring again to Charts E and F, the configuration of the $-CH_2-V-COOR_{10}$ moiety in the formual-LXI bis-esters or the configuration of the $-CH_2-Z-COOR_{10}$ moiety in the formula-LXVIII bis-esters does not change during these transformations of LXI to LXII, LXIII, and LXIV, and of LXVIII to LXIX, LXX, and LXXI. Therefore, when in formula LXI, for example, V is $-CH_2CH_2CH_2OCH_2-$ and $R_2$ is pentyl, natural and 15-epi 3-oxa-$PGE_1$ esters (LXII) are obtained when $-CH_2-V-COOR_{10}$ is attached initially (LXI) in alpha configuration, and natural and 15-epi 8-iso-3-oxa-$PGE_1$ esters are obtained when the moiety is attached in beta configuration. Similarly, when in formula LXI, V is cis-$CH=CHCH_2OCH_2-$ or $-C\equiv CCH_2OCH_2-$ and $R_2$ is pentyl, natural and 15-epi 3-oxa-$PGE_2$ esters and natural and 15-epi 5,6-dehydro-$PGE_2$ esters are obtained when $-CH_2-V-COOR_{10}$ is attached initially in alpha configuration, and the corresponding 8-iso compounds are obtained when that moiety is attached in beta configuration. The same retention of $-CH_2-V-COOR_{10}$ configuration occurs when formula LXIII and LXIV compounds are produced, and a similar retention of $-CH-Z-COOR_{10}$ configuration occurs when formula LXIX, LXX, and LXXI compounds are produced from formula LXVIII bis-esters.

The 3-oxa and 4-oxa $PGE_3$-type compounds encompassed by formulas XXVI and XXVII are prepared by the transformations shown in Chart H, wherein $C_jH_{2j}$, Q, $R_9$, $R_{10}$, $R_{13}$, THP, Y, and ~ are as defined above.

Starting material LXXII, previously discussed (Chart G) is converted to the formula -LXXXIII compound by several steps known in the art, employing first a Wittig reaction of a phosphonium salt of a haloalkyne of the formula $Br-CH_2-C_jH_{2j}-C\equiv C-R_9$ wherein $C_jH_{2j}$, and $R_9$ are as defined above. See, for example, U. Axen et al., Chem. Comm. 1969, 303, and ibid. 1970, 602.

Compound LXXXIII is then alkylated with an alkylation agent of the formula $Hal-CH_2-C\equiv C-Y-COOR_{10}$ wherein Y, $R_{10}$, and Hal are as defined above, i.e., Y is $-C_pH_{2p}-O-CR_5R_6-$ or $-C_qH_{2q}-O-CR_5R_6-CR_7R_8-$, $R_{10}$ is the same as the definition of $R_1$ except that $R_{10}$ does not include hydrogen, and Hal is chloro, bromo, or iodo. These alkylating agents have been discussed above in connection with Charts D and E and the procedures for alkylation are similar to those employed in preparing the acetylenic compounds above. See also Axen et al., references cited.

CHART H

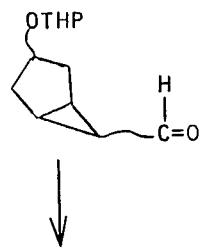

LXXII

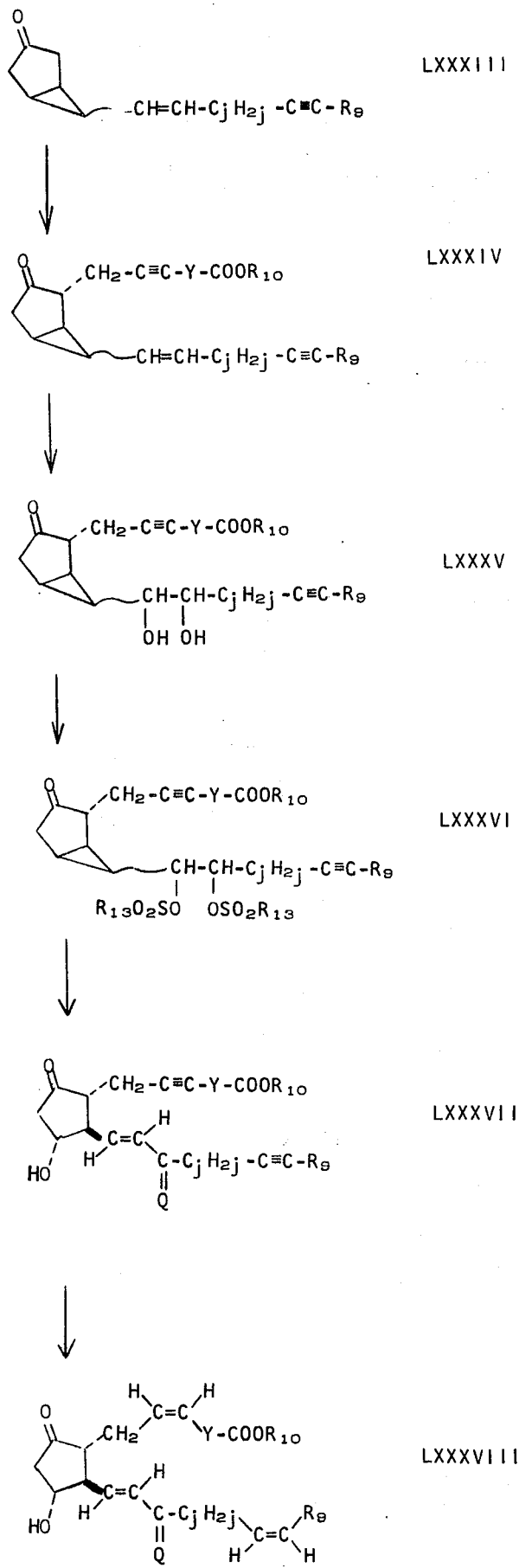

Accordingly, for the preparation of 3-oxa-PGE$_3$ compounds of formula XXVI wherein C$_p$H$_{2p}$ is methylene, there is used an alkylating agent of the formula Hal—CH$_2$—C ≡ C—CH$_2$—O—CH$_2$—COOR$_{10}$ prepared as discussed above in connection with alkylating agent LXXVII.

Referring again to Chart H, after alkylation, compound LXXXIV is hydroxylated to glycol LXXXV. Hydroxylation reagents and procedures for this purpose are known in the art. See also Axen et al., references cited.

Bis(alkanesulfonic acid) esters LXXXVI are prepared by reacting glycol LXXXV with an alkanesulfonyl chloride or bromide, for example methanesulfonyl chloride in the presence of a tertiary amine, by methods known in the art.

Referring again to Chart H, bis(sulfonic acid) esters LXXXVI are transformed to oxa-phenylene bisdehydro PGE$_3$-type compounds LXXXVII by reaction with water in the range about 0° to about 60° C., preferably in an acetone-water mixture, as known in the art and discussed hereinabove. See also Axen, references cited.

Transformation of LXXXVII to the PGE$_3$-type compounds LXXXVIII is accomplished by hydrogenation of LXXXVII using a catalyst which catalyzes hydrogenation of —C ≡ C— only to cis-CH=CH—, as known in the art and discussed hereinabove. Preferred is Lindlar catalyst in the presence of quinoline, see Axen, references cited.

The product is a mixture of formula-LXXXVIII C-15 epimers which are separated from by-products and from each other by silica gel chromatography.

The transformations of the formula-LXXXVIII PGE$_3$-type products to the corresponding PGF$_3$, PGA$_3$, and PGB$_3$ products are carried out by the steps shown in Chart A, discussed hereinabove.

The formula-LXII and LXIX 3-oxa and 4-oxa PGE-type compounds and the formula-LXIII and LXX 3-oxa and 4-oxa PGA-type compounds shown in Charts E and F and the formula-LXXXVIII 3-oxa and 4-oxa PGE$_3$-type compounds shown in Chart H are all R$_{10}$ carboxylic acid esters, wherein R$_{10}$ is as defined above. Moreover, when those PGE-type and PGA-type R$_{10}$ esters are used to prepare the other 3-oxa and 4-oxa prostaglandin-like compounds according to Charts A, B, C, and D, corresponding R$_{10}$ esters are likely to be produced, especially in the case of the 3-oxa and 4-oxa PGF-type compounds. For some of the uses described above, it is preferred that the novel formula XVIII-to-LVII 3 oxa and 4-oxa prostaglandin-like compounds of this invention be in free acid form, or in salt form which requires the free acid as a starting material. The PGF-type esters of formulas XXVII–XXXVII and the PGB-type compounds of formulas XLVIII–LVII are easily hydrolyzed or saponified to the free acids by the usual known procedures, especially when R$_1$ (R$_{10}$) is alkyl of one to 4 carbons, inclusive, preferably methyl or ethyl.

On the other hand, the PGE-type esters of formulas XVIII–XXVII and the PGA-type esters of formulas XXXVIII–XLVII are difficult to hydrolyze or saponify without causing unwanted structural changes in the desired acids. There are several other procedures to make the free acid forms of these PGE- and PGA-type compounds.

One of those procedures is applicable mainly in preparing the free acids from the corresponding alkyl esters wherein the alkyl group contains one to 8 carbon atoms, inclusive. That procedure comprises subjecting the alkyl ester to the acylase enzyme system of a microorganism species of Subphylum 2 of Phylum III, and thereafter isolating the acid. See West Germany Offenlegungsschrift No. 1,937,678; reprinted in Farmdoc Complete Specifications, Book No. 13, No. 6863 R, Week R5, Mar. 18, 1970.

Expecially preferred for this purpose are species of the orders Mucorales, Hypocreales, Moniliales, and Actinomycetales. Also especially preferred for this purpose are species of the families Mucoraceae, Cunninghamellaceae, Nectreaceae, Moniliaceae, Dematiaceae, Tuberculariaceae, Actinomycetaceae, and Streptomycetaceae. Also especially preferred for this purpose are species of the genera Absidia, Circinella, Gongronella, Rhizopus, Cunninghamella, Calonectria, Aspergillus, penicillium, Sporotrichum, Cladosporium, Fusarium, Nocardia and Streptomyces. Examples of microorganisms falling within the scope of those preferred orders, families, and genera are listed in U.S. pat. No. 3,290,226.

This enzymatic ester hydrolysis is carried out by shaking the PG-type alkyl ester in aqueous suspension with the enzyme contained in a culture of one of the above-mentioned microorganism species until the ester is hydrolyzed. A reaction temperature in the range 20° to 30° C. is usually satisfactory. A reaction time of one to 20 hours is usually sufficient to obtain the desired hydrolysis. Exclusion of air from the reaction mixture, for example, with argon or nitrogen is usually desirable.

The enzyme is obtained by harvest of cells from the culture, followed by washing and resuspension of the cells in water, and cell disintegration, for example, by stirring with glass beads or by sonic or ultrasonic vibrations. The entire aqueous disintegration mixture is used as a source of the enzyme. Alternatively and preferably, however, the cellular debris is removed by centrifugation or filtration, and the aqueous supernatant or filtrate is used.

In some cases, it is advantageous to grow the microorganism culture in the presence of an alkyl ester of an aliphatic acid, acid containing 10 to 20 carbon atoms, inclusive, and said alkyl containing one to 8 carbon atoms, inclusive, or to add such an ester to the culture and maintain the culture without additional growth for one to 24 hours before cell harvest. Thereby, the enzyme produced is sometimes made more effective in transforming the PG-type ester to the free acid. An example of a useful alkyl ester for this purpose is methyl oleate.

This enzymatic hydrolysis is also applicable to the above PFG- and PGB-type alkyl esters.

Another procedure for making the free acid form of the above PGE- and PGA-type compounds involves treatment of certain haloethyl esters of those acids with zinc metal and an alkanoic acid of 2 to 6 carbon atoms, preferably acetic acid. Those haloethyl esters are the esters wherein R$_{10}$ is ethyl substituted in the β-position with 3 chloro, 2 or 3 bromo, or one, 2, or 3 iodo. of those haloethyl moieties, β,β,β-trichloroethyl is preferred. Zinc dust is preferred as the physical form of the zinc. Mixing the haloethyl ester with the zinc dust at about 25° C. for several hours usually causes substantially complete replacement of the haloethyl moiety of the ester with hydrogen. The free acid is then isolated from the reaction mixture by procedures known to the art. This procedure is also applicable to the production of PFG- and PGB-type free acids.

Referring to Charts E and F, formula LIX cyclic ketals and formula LXVI olefins wherein $R_{10}$ is haloethyl as above defined are necessary as intermediates for this route to the final PGE, PGF, PGA, and PGB type free acids. These haloethyl ester intermediates can be prepared by alkylation of cyclic ketal LVIII (Chart E) or olefin LXV (Chart F), respectively, with the appropriate formula LXV to LXXXII alkylating agent wherein $R_{10}$ is haloethyl as above defined. However, preferred routes to the formula LIX and LXVI haloethyl ester intermediates are shown in Charts I and J.

In Charts I and J, $r_2$, $R_{11}$, $R_{12}$, V, Z, and ~ are as defined above. Haloethyl represents ethyl substituted in the β-position with 3 chloro, 2 or 3 bromo, or 1, 2, or 3 iodo, preferably —$CH_2CCl_3$. $R_{16}$ represents alkyl of one to 4 carbon atoms, inclusive, preferably methyl or ethyl.

Compound LXXXIX in Chart I is within the scope of compound LIX in Chart E. Compound LXV in Chart J is within the scope of compound LXVI in Chart F. Ketones LXXXIX and XCV are reduced to corresponding hydroxy compounds XC and XCVI, respectively, with a carbonyl reducing agent, e.g., sodium borohydride, as descried above in discussion of Chart A. Then, hydroxy esters XC and XCVI are saponified by known procedures to hydroxy acids XCI and XCVII, respectively. These two hydroxy acids are transformed to keto haloethyl esters XCIV and C, respectively, by oxidation of the hydroxy group to keto and esterification of the carboxyl group to —COO—haloethyl. As shown in Charts I and J, these two reactions are carried out in either order. However, it is preferred to oxidize first and then esterify.

CHART I

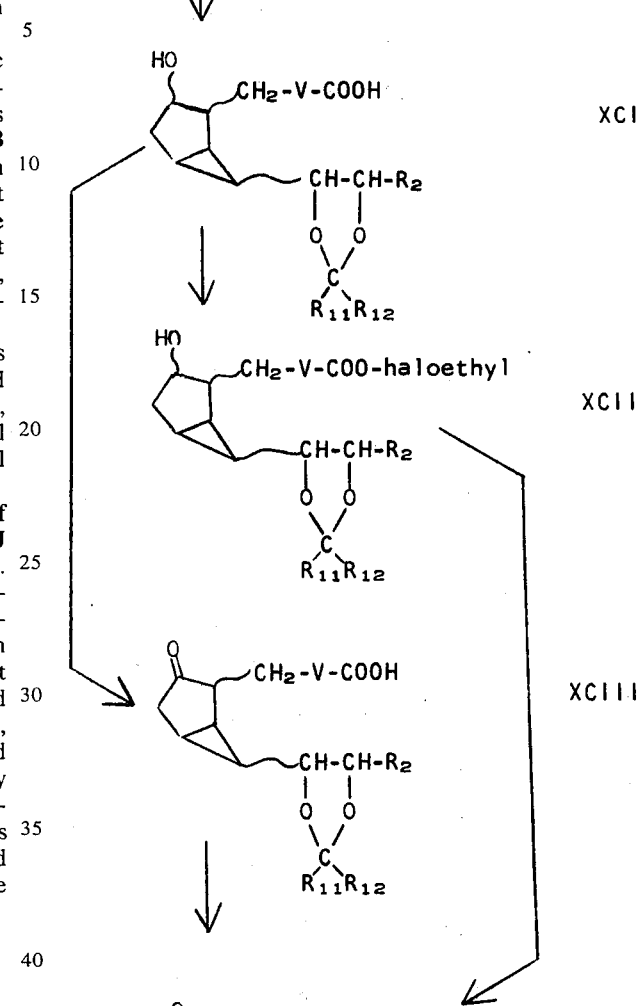

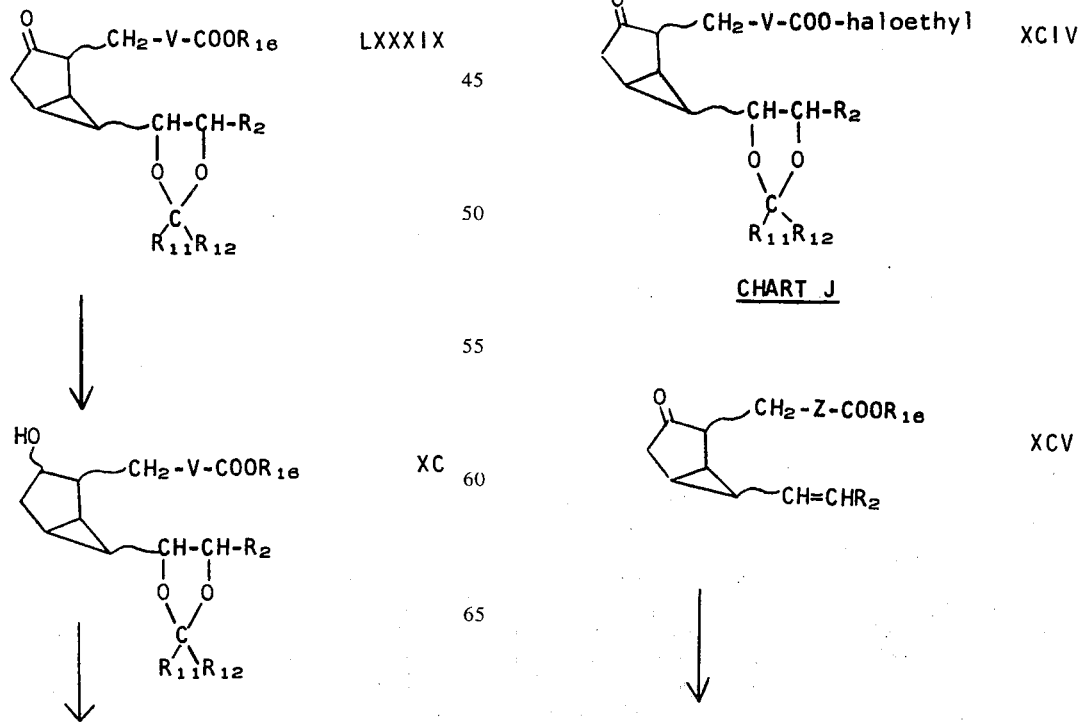

CHART J

CHART J continued

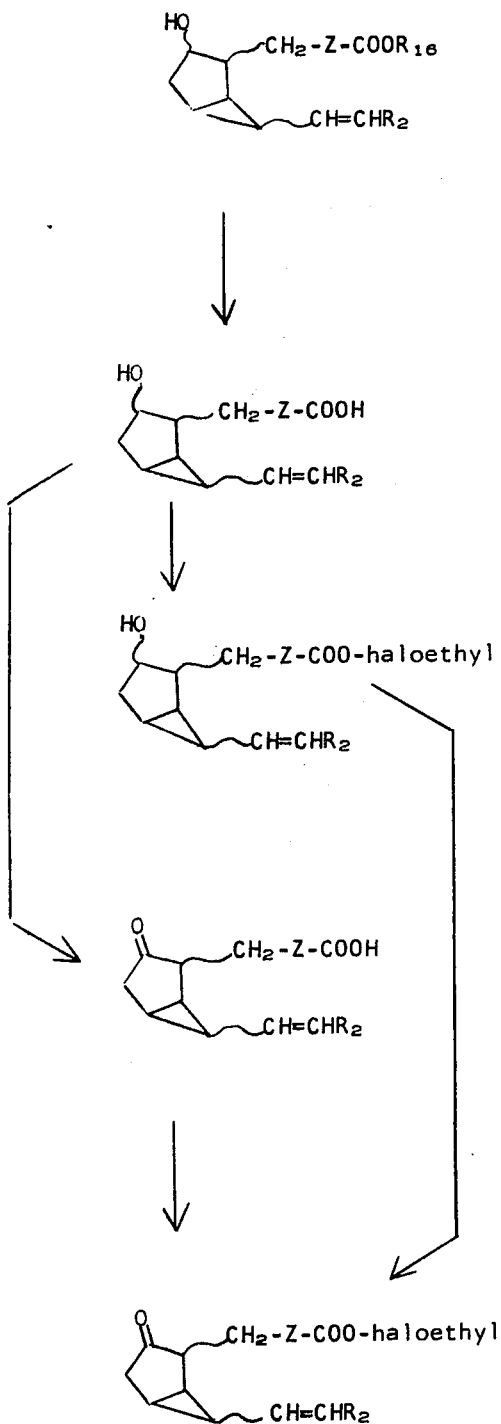

Hydroxy acids XCI and XCVII are oxidized to keto acids XCIII and XCIX, respectively, and hydroxy haloesters XCII and XCVIII are oxidized to keto haloesters XCIV and C, respectively, by reaction with an oxidizing agent which does not attack other parts of these molecules, especially the cyclic ketal group of compounds XCI and XCII or the ethylenic linkage of compounds XCVII and XCVIII. An especially useful reagent for this purpose is the Jones reagent. Acetone is a suitable diluent for this purpose, and a slight excess of oxidant and temperatures at least as low as about 0° C., preferably about −10° to about −20° C. Should be used. The oxidation proceeds rapidly and is usually complete in about 5 to about 30 minutes. Excess oxidant is destroyed, for example, by addition of a lower alkanol, advantageously isopropyl alcohol, and the aldehyde is isolated by conventional methods, for example, by extraction with a suitable solvent, e.g., diethyl ether. Other oxidizing agents can also be used. Examples are mixtures of chromium trioxide and pyridine or mixtures of dicyclohexylcarbodiimide and dimethyl sulfoxide. See, for example, J. Am. Chem. Soc. 87, 5661 (1965).

Haloethyl esters XCII, XCIV, XCVIII, and C are prepared by reacting acids XCI, XCIII, XCVII, and XCIX, respectively, with the appropriate haaloethanol, e.g., $\beta,\beta,\beta$-trichloroethanol, in the presence of a carbodiimide, e.g., dicyclohexylcarbodiimide, and a base, e.g., pyridine, preferably in the presence of an inert liquid diluent, e.g., dichloromethane, for several hours at about 25° C.

Still another method of obtaining the free acid form of these 3-oxa and 4-oxa PG type compounds, preferred for the PGE analogs, but useful for the PGF, PGA, and PGB analogs as well, is by enzymatic hydrolysis using an esterase enzyme composition obtained from the marine invertebrate Plexaura homomalla (Esper), 1792. Plexaura homomalla is a member of the subclass Octocorallia, order Gorgonacea, suborder Holaxonia, family Plexauridae, genus Plexaura. See, for example, Bayer, "The Shallow-Water Octocorallia of the West Indian Region", Martinus Nijhoff, The Hague (1961). Colonies of these Plexaura homomalla are abundant on the ocean reefs in the zone from the low-tide line to about 25 fathoms in the tropical and subtropical regions of the western part of the Atlantic Ocean, from Bermuda to the reefs of Brazil, including the eastern shore reefs of Florida, the Caribbean island and mainland reefs, and the Gulf of Mexico island and mainland reefs. These colonies are bush-like or small tree-like in habit and are readily identified for collection as Plexaura homomalla (Esper), 1792, by those of ordinary skill in this art. Two forms exist, the "R" form and the "S" form. See W. P. Schneider et al., J. Am. Chem. Soc. 94, 2122 (1972).

The esterase enzyme composition is produced by the steps:
(1) extracting colonies or colony pieces of the marine invertebrate Plexaura homomalla (Esper), 1792, forma R or forma S, with liquid acetone for a sufficient time to remove substantially all soluble lipids, and
(2) recovering the acetone-insoluble matter as said composition.

The colonies of Plexaura homomalla are used either in their as-harvested form or in broken or chopped pieces. It is immaterial whether they are used fresh from their natural ennvironment, or after freezing and thawing, or even after drying under amient conditions.

The extraction with acetone may be done batch-wise, as by stirring in a container, or by percolation, or by continuous methods of extraction known in the art. If stirring is used, it is advantageous to first chop the Plexaura homomalla into small pieces, for exammple less than 3 mm. in greatest dimension. The product is accordingly then a powder consisting of pieces smaller than 3 mm. Contact with acetone is continued until substantially all of the soluble lipids are removed. normally one hour is sufficient, although a longer time is required for whole colonies and a shorter time is sufficient for chopped colonies with efficient extraction. The end-point can be determined simply by examination of the acetone, as by evaporation and by physical measurements on any residue thus obtained. The extraction temperature is kept below 50° C. to avoid denaturation of the enzyme, and is preferably in the range 20° to 30° C. Lower temperatures may be used but the extraction then proceeds more slowly. The extraction is generally done at atmospheric pressure, but it may be carried out at higher or lower pressures provided the acetone is in a liquid state when contacting the Plexaura homomalla.

The acetone-insoluble enzyme composition is recovered from the acetone by decantation, filtration, centrifugation, or other convenient method for separating solids and liquids. A small amount of adherent acetone, for example, 10% of the weight of the composition, may be left on the product but it is preferred that the amount be lowered to less than 1%, for example by drying under ambient conditions or under reduced pressure. The product can then be stored without deterioration, preferably at about −20° C.

In utilizing the above esterase enzyme composition for the purposes of this invention, the 3-oxa or 4-oxa PG-type ester is contacted with a mixture of the enzyme composition and water. The ester is conveniently added as a solution, for example in ethanol or benzene, to about 50–100 times its weight of water. The enzyme ccomposition is added in an amount about 1–15 times the weight of ester. The mixture is stirred until the ester is hydrolyzed, generally about 18–24 hours at 25° C. Temperatures of about 0°–0° C. may be employed, although about 25° C. is preferred. The progress of hydrolysis is readily followed by analysis, for example by thin-layer chromatography by methods known in the art. See, for example, Hamberg et al., J. Biol. Chem. 241, 257 (1966). Finally, several volumes of acetone are added and the soluble acid products are recovered by filtration concentration, and extraction using methods known in the art.

As described above, the alkylations of cyclic ketal LVIII to LIX (Chart E) and olefin LXV to LXVI (Chart F) usually produces a mixture of alpha and beta alkylation products with respect to the —CH$_2$—V—COOR$_{10}$ and —CH$_2$—Z—COOR$_{10}$ moieties. Also as described above, those two isomers lead to different final products, alpha leading to the PG type series, and beta leading to the 8-iso-PG type series. If a compound in one or the other of those two series is preferred, there are two methods for favoring production of the preferred final product.

One of those methods involves isomerization of the final product of formulas XVIII to XXVII. Either the alpha isomer of a formula XVIII-to-XXVII compound, ester or free acid, or the corresponding beta isomer is maintained in an inert liquid diluent in the range of 0° to 80° C. and in the presence of a base characterized by its water solution having a pH below about 10 until a substantial amount of the isomer has been isomerized to the other isomer, i.e., alpha to beta or beta to alpha. Preferred bases for this purpose are the alkali metal salts of carboxylic acids, especially alkanoic acids of 2 to 4 carbon atoms, e.g., sodium acetate. Examples of useful inert liquid diluents are alkanols of one to 4 carbon atoms, e.g., ethanol. This reaction at about 25° takes about one to about 20 days. Apparently an equilibrium is established. The mixtures of the two isomers, alpha and beta, are separated from the reaction mixture by known procedures, and then the two isomers are separated from each other by known procedures, for example, chromatography, recrystallization, or a combination of those. The less preferred isomer is then subjected to the same isomerization to produce more of the preferred isomer. In this manner, by repeated isomerizations and separation, substantially all of the less preferred isomer of the formula XVIII-to-XXVII compound is transformed to more preferred isomer.

The second method for favoring productin of a preferred formula XVIII-to-XXVII isomer involves any one of the keto intermediates of formulas LIX, LX, LXVI, or LXVII (Charts E and F). Either the alpha form or the beta form of one of those intermediates is transformed to a mixture of both isomers by maintaining one or the other isomer, alpha or beta, in an inert liquid diluent in the presence of a base and in range 0° to 100° C. until a substantial amount of the starting isomer has been isomerized to the other isomer. Preferred bases for this isomerization are alkali metal amides, alkali metal alkoxides, alkali metal hydrides, and triarylmethyl alkali metals. Especially preferred are alkali metal tert-alkoxides of 4 to 8 carbon atoms, e.g., potassium tert-butoxide. This reaction at about 25° C. proceeds rapidly (one minute to several hours). Apparently an equilibrium mixture of both isomers is formed, starting with either isomer. The isomer mixtures in the equilibrium mixture thus obtained are isolated by known procedures, and then the two isomers are separated from each other by known procedures, for example, chromataography. The less preferred isomer is then subjected to the same isomerization to produce more of the preferred isomer. In this manner, by repeated isomerizations and separations, substantially all of the less preferred isomer of any of these intermediates is transformed to the more preferred isomer. Cyclic acetalketone intermediates of formula LIX are preferred over the other intermediates for this isomerization procedure.

Certain 15-alkyl 3-oxa and 4-oxa PGE, PGF, PGA, and PGB type compounds of formula XVIII to LVII wherein R$_3$ is alkyl of one to 4 carbon atoms, inclusive, preferably methyl or ethyl, are preferred over the corresponding 3-oxa and 4-oxa PGE, PGF, PGA, and PGB type compounds in which R$_3$ is hydrogen for the above-described pharmacological purposes.

These 15-alkyl prostaglandin analogs are surprisingly and unexpectedly more useful than the corresponding 15-hydrogen compounds for the reason that they are substantially more specific with regard to potency in causing prostaglandin-like biological responses, and have a substantially longer duration of biological activity. For that reason, fewer and smaller doses of these 15-alkyl prostaglandin analogs are needed to attain the desired pharmacological results.

Although the above-mentioned 15-alkyl compounds are produced by the methods outlined above in Charts A-H, the preferred methods are set forth in Chart K as follows.

In Chart K, R$_{10}$ is alkyl of one to 4 carbon atoms, inclusive, and A, Hal, R$_1$, V, and ~ are as heretofore defined. Also in Chart K, r$_{17}$ is (1) r$_2$ as defined above or (2) 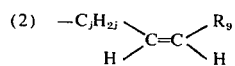

wherein $C_jH_{2j}$ and $R_a$ are as defined above; and $R_{18}$ is $R_1$ as defined above or silyl of the formula $-Si-(T)_3$ wherein T is alkyl of one to 4 carbon atoms, inclusive, aralkyl of 7 to 12 carbon atoms, inclusive, phenyl, or phenyl substituted with one to 2 fluoro, chloro, or alkyl of one to 4 carbon atoms, inclusive. The various T's of a $-Si(T)_3$ moiety are alike or different. For example, a $-Si(T)_3$ can be trimethylsilyl, dimethylphenylsilyl, or methylphenylbenzylsilyl. Examples of alkyl of one to 4 carbon atoms, inclusive, are methyl, ethyl, propyl, isopropyl, isobutyl, sec-butyl, and tertbutyl. Examples of aralkyl of 7 to 12 carbon atoms, inclusive, are benzyl, phenethyl, α-phenylethyl, 3-phenylpropyl, α-naphthylmethyl, and 2-(β-naphthyl)ethyl. Examples of phenyl substituted with one or 2 fluoro, chloro, or alkyl of one to 4 carbon atoms, inclusive, are p-chlorophenyl, m-fluorophenyl, o-tolyl, 2,4-dichlorophenyl, p-tert-butylphenyl, 4-chloro-2-methylphenyl, and 2,4-dichloro-3-methylphenyl.

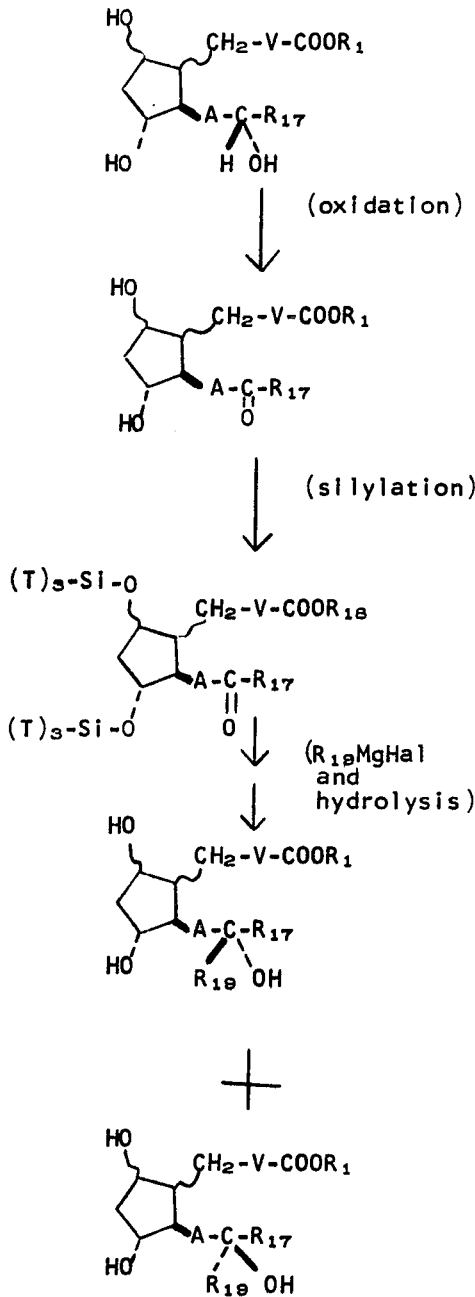

CHART K

In Chart K, the final 3-oxa and 4-oxa PGFα and PGFβ -type products are those encompassed by formulas CIV and CV which are within the scope of PGF-type compounds of formula XXVIII–XXXVII The initial optically active or racemic reactants of formula CI in Chart K, i.e., the 3oxa and 4-oxa PGF$_1$-, PGF$_2$-, PGF$_3$-, dehydro-PGF$_2$-, and dihydro-PGF$_1$- type compounds in their α and β forms, and their esters, are prepared by methods described herein. These acids and esters of formula CI are transformed to the corresponding intermediate 15-oxo acids and esters of formula CII by oxidation with reagents such as 2,3-dichloro-5,6-dicyano-1,4-benzoquinone, activated manganese dioxide, or nickel peroxide (see Fieser et al., "Reagents for Organic Syntheses," pp. 215, 637, and 731). Alternatively, and especially for the formula-CI reactants wherein A is $-CH_2CH_2-$, and V is Y as defined above, these oxidations are carried out by oxygenation in the presence of the 15-hydroxy-prostaglandin dehydrogenase of swine lung (see Arkiv för Kemi 25, 293 (1966)). These reagents are used according to procedures known in the art. See, for example, J. Biol. Chem. 239, 4097 (1964).

Referring again to Chart K, intermediate compounds CII are transformed to silyl derivatives CIII by procedures known in the art. See, for example, Pierce, "Silylation of Organic Compounds," Pierce Chemical Co., Rockford, Ill. (1968). Both hydroxy groups of the formula-CII reactants are thereby transformed to $-O-Si-(T)_3$ moieties wherein T is as defined above, and sufficient of the silylating agent is used for that purpose according to known procedures. When $R_1$ in intermediate CII is hydrogen, the $-COOH$ moiety thereby defined is simultaneously transformed to $-COO-Si-(T)_3$, additional silylating agent being used for this purpose. This latter transformation is aided by excess silylating agent and prolonged treatment. When $R_1$ in formula CII is alkyl, then $R_{18}$ in formula CIII will also be alkyl. The necessary silylating agents for these transformations are known in the art or are prepared by methods known in the art. See, for example, Post, "Silicones and Other Organic Silicon Compounds, "Reinhold Publishing Corp., New York, N.Y. (1949).

Referring again to Chart K, intermediate silyl compounds CIII are transformed to the final compounds of formulas CIV and CV by first reacting the silyl compound with a Grignard reagent of the formula $R_{19}MgHal$ wherein $R_{19}$ is as defined above, and Hal is chloro, bromo, or iodo. For this purpose, it is preferred that Hal be bromo. This reaction is carried out by the usual procedure for Grignard reactions, using diethyl ether as a reaction solvent and saturated aqueous ammonium chloride solution to hydrolyze the Grignard complex. The resulting disilyl or trisilyl tertiary alcohol is then hydrolyzed with water to remove the silyl groups. For this purpose, it is advantageous to use a mixture of water and sufficient of a water-miscible solvent, e.g., ethanol to give a homogenous reaction mixture. The hydrolysis is usually complete in 2 to 6 hours at 25° C., and is preferably carried out in an atmosphere of an inert gas, e.g., nitrogen or argon.

The mixture of 15-α and 15-β isomers obtained by this Grignard reaction and hydrolysis is separated by procedures known in the art for separating mixtures of prostanoic acid derivatives, for example, by chromatography on neutral silica gel. In some instances, the lower alkyl esters, expecially the methyl esters of a pair of 15-α and 15-β isomers are more readily separated by silica gel chromatography than are the corresponding acids. In those cases, it is advantageous to esterify the mixture of acids as described below, separate the two esters, annd then, if desired, saponify the esters by procedures known in the art for saponification of prostaglandins F.

Although formula-CIV and —CV compounds wherein A is —CH$_2$CH$_2$— V is Y as defined above may be produced according to the processes of Chart K, it is preferred to produce those novel dihydro-PGF$_1$ analogs by hydrogenation of one of the corresponding unsaturated compounds, i.e., a compound of formula CIV or CV wherein A is trans —CH=CH— and V is either saturated or unsaturated as defined above. This hydrogenation is advangateously carried out catalytically, for example, in the presence of a 5% palladiumon-charcoal catalyst in ethyl acetate solution at 25° C. and one atmosphere pressure of hydrogen.

The novel 15-alkyl 3-oxa or 4-oxa PGE-type acids and esters of formula XVIII to XXVII are prepared from the corresponding PGF compounds, heretofore described, by oxidation. For this purpose, an oxidizing agent is used which selectively oxidizes secondary hydroxy groups to carbonyl groups in the presence of carbon-carbon double bonds. The PGF$_\beta$ isomers are preferred starting materials when the carboxyl side chain is alpha, although the corresponding α-hydroxy isomers are also usefl for this purpose.

Oxidation reagents useful for this transformation are known to the art. An especially useful reagent for this purpose is the Jones reagent. Acetone is a suitable diluent for this purpose, and a slight excess beyond the amount necessary to oxidize one of the secondary hydroxy groups of the 15-alkyl PGF reactant is used. Reaction temperatures at least as low as about 0° C. should be used. Preferred reaction temperatures are in the range −10° to −50° C. The oxidation proceeds rapidly and is usually complete in about 5 to 20 minutes. The excess oxidant is destroyed, for example by addition of a lower alkanol, advantageously, isopropyl alcohol, and the PGE-type product is isolated by conventional methods.

Examples of other oxidation reagents useful for this purpose are silver carbonate on Celite (Chem. Commun. 1102 (1969)), mixtures of chromium trioxide and pyridine (Tetrahedron Letters 3363 (1968), J. Am. Chem. Soc. 75, 422 (1953), and Tetrahedron, 18, 1351 (1962)), mixtures of sulfur trioxide in pyridine and dimethyl sulfoxide (J. Am. Chem. Soc. 89, 5505 (1967)), and mixtures of dicyclohexylcarbodiimide and dimethyl sulfoxide (J. Am. Chem. Soc. 87, 5661 (1965)).

The novel 15-alkyl 3-oxa or 4-oxa PGA-type acids and esters of formulas XXXVIII to XLVII are prepared from the 15-alkyl 3-oxa or 4-oxa PGE compounds, heretofore described, by dehydration. For this purpose, a dehydrating agent is used which removes the hydroxy group from the alicyclic ring in the presence of a hydroxy group on a tertiary carbon atom.

Dehydration agents useful for this transformation are known in the art. Any of the known substantially neutral dehydrating agents is used for these reactions. See Fieser et al., "reagents for Organic Syntheses", John Wiley & Sons, Inc., New York, 1967. Preferred dehydrating agents are mixtures of at least an equivalent amount of a carbodiimide and a catalytic amount of a copper (11) salt. Especially preferred are mixtures of at least an equivalent amount of dicyclohexylcarbodiimide and a catalytic amount of copper (11) chloride. An equivalent amount of a carbodiimide means one mole of the carbodiimide for each mole of the PGE-type reactant. To ensure completeness of the reaction, it is advantageous to use an excess of the carbodiimide, i.e., 1.5 to 5 or even more equivalents of the carbodiimide.

The dehydration is advantageously carried out in the presence of an inert organic diluent which gives a homogeneous reaction mixture with respect to the PGE-type reactant and the carbodiimide. Diethyl ether is a suitable diluent. It is advantageous to carry out the dehydration in an atmosphere of an inert gas, e.g., nitrogen, helium, or argon. The time required for the dehydration will depend in part on the reaction temperature. With the reaction temperature in the range 20° to 30°C., the dehydration usually takes place in about 40 to 60 hours. The PGA-type product is isolated by methods known in the art, e.g., filtration of the reaction mixture and concentration of the filtrate. If desired, the product is purified by methods known in the art, advantageously by chromatography on silica gel.

The 3-oxa-PGE$_1$ compounds encompassed by formula XVIII and the 3-oxa-PGF$_{1\alpha}$ compounds encompassed by formula XXVIII are also prepared by the transformations shown in Charts L and M. Therein R$_1$, R$_2$, and ~ are as defined above and Q' is

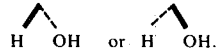

In Chart L, wherein are shown the steps leading to intermediate CXI of Chart M, R$_{20}$ is either

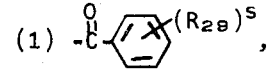

wherein R$_{2a}$ is alkyl of one to 4 carbon atoms, inclusive, phenylalkyl of 7 to 10 carbon atoms, inclusive, or nitro, and s is zero to 5, inclusive, provided that not more than two R$_{2a}$'s are other than alkyl, and that the total number of carbon atoms in the R$_{29}$'s does not exceed 10 carbon atoms;

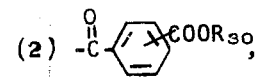

wherein R$_{30}$ is alkyl of one to 4 carbon atoms, inclusive;

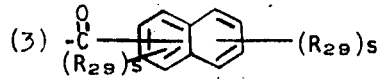

wherein R$_{2a}$ and s are as defined above; or (4) acetyl. Use of acetyl or p-phenylbenzoyl is known in the art (see Corey et al., J. Am. Chem. Soc. 93, 1491 (1971)).

In Chart L, R$_{21}$ is a "blocking group", which is defined as any group which replaces hydrogen of the hydroxyl groups, which is not attacked by nor is reactive to the reagents used in the respective transformations to the extent that the hydroxyl group is, and which is subsequently replaceable by hydrogen at a later stage in the preparation of the prostaglandin-like products. Several blocking groups are known in the art, e.g., tetrahydropyranyl and substituted tetrahydropyranyl (see Corey, Proceedings of the Robert A. Welch Foundation Conferences on Chemical Research. XII Organic Synthesis, pp. 51–79. (1969).
CHART L
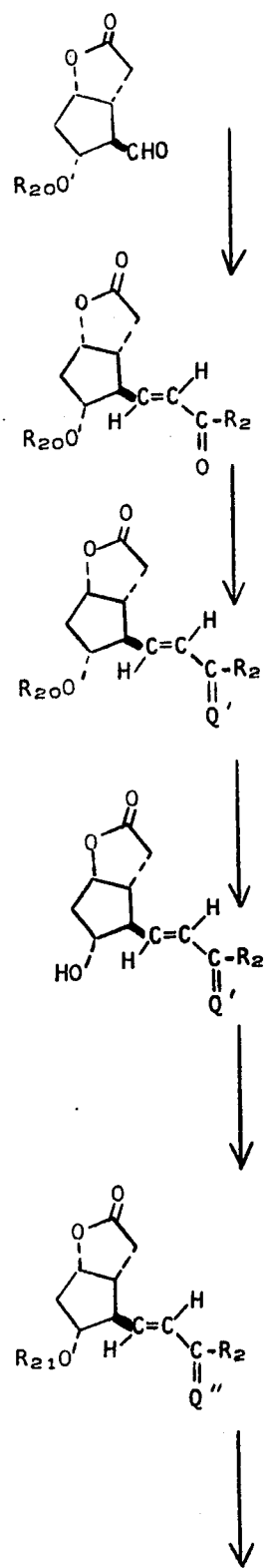
CHART M
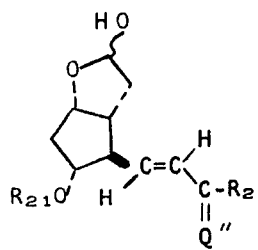
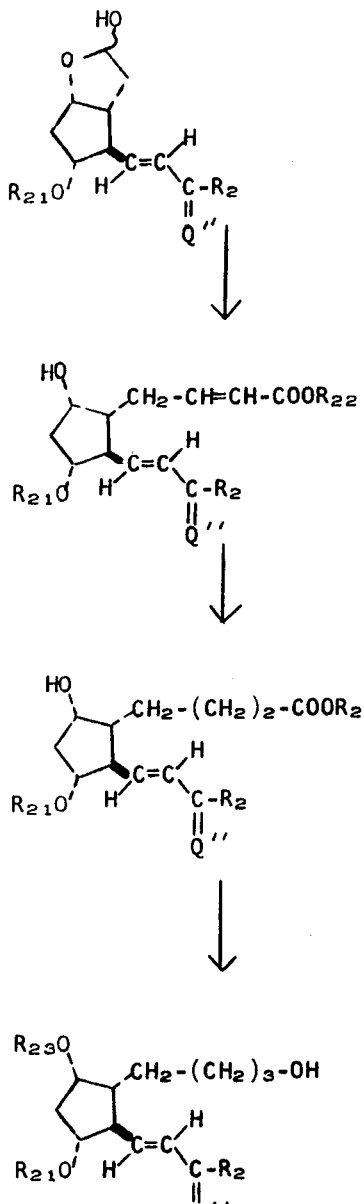

CHART M continued

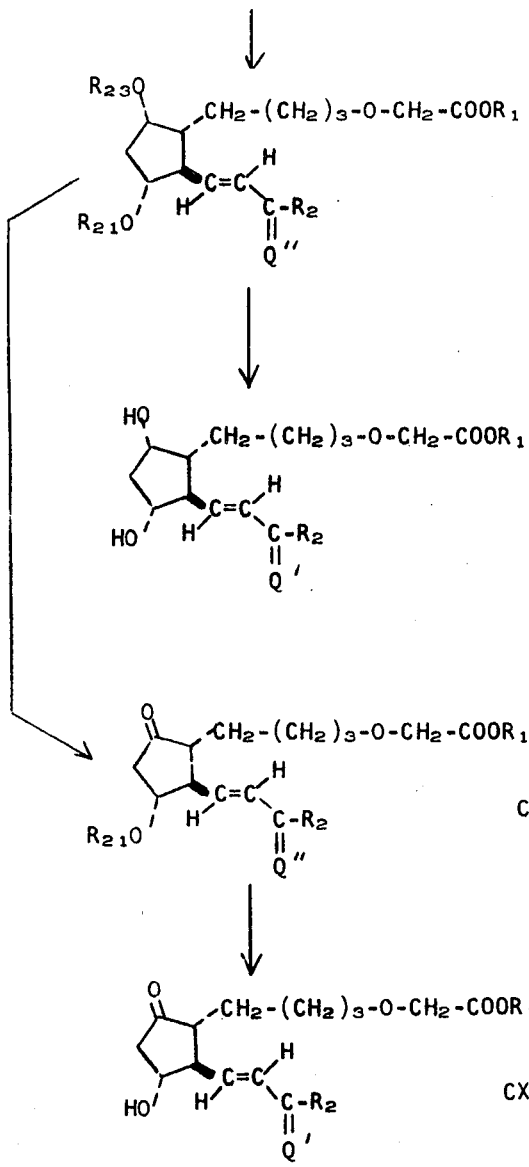

Those which have been found useful in this series of transformations include (a) tetrahydropyranyl; (b) tetrahydrofuranyl; and (c) a group of the formula

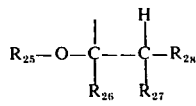

wherein $R_{25}$ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein $R_{26}$ and $R_{27}$ are the same or different, being hydrogen, alkyl of one to 4 carbon atoms, inclusive, phenyl or phenyl substituted with one, 2, or 3 alkyl of one to 4 carbon atoms, inclusive, or, when $R_{26}$ and $R_{27}$ are taken together, —(CH$_2$)a— or —(CH$_2$)b—O—(CH$_2$)c— wherein a is 3, 4, or 5, b is one, 2, or 3, and c is one, 2, or 3 with the proviso that b plus c is 2, 3, or 4, and wherein $R_{28}$ is hydrogen or phenyl.

Furthermore, in Chart L, Q'' is either

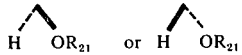

wherein $R_{21}$ is a blocking group as defined above.

The starting materials represented by formula CVI in Chart L are known in the art or are prepared by methods known in the art. See, for example, E.J. Corey et al., J. Am. Chem. Soc. 91, 5675 (1969) for the dl (racemic) form and 92, 397 (1970) for the optically active form. Likewise see Belgian Pat. No. 781,979, Oct. 12, 1972, or West German Offenlegunsschrift No. 2,217,044, Oct. 26, 1972. See Derwent Farmdoc 71483T-B, T48.

In that Belgian patent an iodolactone of the formula

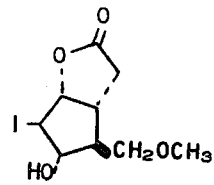

is subjected to an acylating agent, for example an acid, an anhydride, or an acyl halide, to replace the hydrogen of the hydroxyl group with $R_{20}$. The resulting compound is next deiodinated, for example with zinc dust or tributyltin hydride. That product is then demethylated, as with boron tribromide. Finally, the aldehyde is formed by oxidation, as with Collins reagent (pyridine-CrO$_3$).

Continuing with Chart L, the formula-CVII compound is obtained by Wittig alkylation of CVI, using the sodio derivative of an appropriate alkylphosphonate of the general formula $(R_{31}O)_2P(O)CH_2C(O)—R_2$ wherein $R_2$ is as defined above and $R_{31}$ is preferably alkyl of one to 8 carbon atoms, inclusive.

As examples of phosphonates useful for this purpose there are:

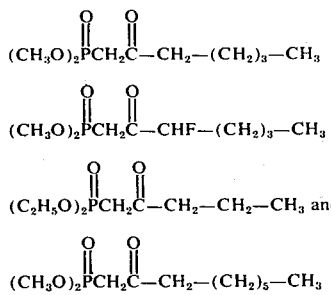

The phosphonates are prepared and used by methods known in the art. See D.H. Wadsworth et al., J. Org. Chem. 30, 680 (1965).

Conveniently, the appropriate aliphatic acid ester is condensed with dimethyl methylphosphonate in the presence of n-butyllithium. For this purpose, acids of the general formula

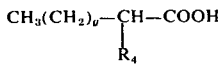

wherein g and $R_4$ are as defined above are used in the form of their lower alkyl esters, preferably methyl or ethyl. These aliphatic acids of various chain length, with or without fluoro substitution within the scope of

are known in the art. The fluoro-substituted acids are readily available, e.g. 2-fluorobutyric, 2-fluorovaleric, 2-fluorohexanoic, 2-fluoroheptanoic, and 2-fluorooctanoic acids.

Continuing with Chart L, the formula-CVIII compound is obtained as a mixture of alpha and beta isomers by reduction of CVII. For this reduction, use is made of any of the known ketonic carbonyl reducing agents which do not reduce ester or acid groups or carbon-carbon double bonds when the latter is undesirable. Examples of those are the metal borohydrides, especially sodium, potassium, and zinc borohydrides, lithium (tri-tert-butoxy)-aluminum hydride, metal trialkoxy borohydrides, e.g., sodium trimethoxyborohydried, lithium borohydride, diisobutyl aluminum hydride, and when carbon-carbon double bond reduction is not a problem, the boranes, e.g., disiamylborane.

For production of natural-configuration PG-type compounds, the desired 15-alpha form of the formula-CVIII compound is separated from the 15-beta isomer by silica gel chromatography.

The formula-CIX compound is then obtained by deacylation of CVIII with an alkali metal carbonate, for example potassium carbonate in methanol at about 25° C.

Previously, the preparation of a bicyclic lactone diol within the scope of formula CIX

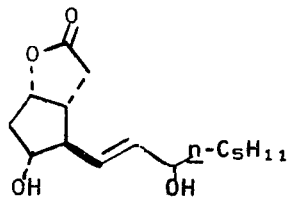

was reported by E. J. Corey et al., J. Am. Chem. Soc. 91, 5675 (1969), and later disclosed in an optically active form by E. J. Corey et al., J. Am. Chem. Soc. 92, 397 (1970). Conversion of this intermediate to $PGE_2$ and $PGF_2\alpha$, either in racemic or optically active form, was disclosed in those publications.

Continuing with Chart L, compound CX is obtained by introducing blocking groups $R_{21}$. When the blocking group is tetrahydropyranyl or tetrahydrofuranyl, the appropriate reagent, e.g., 2,3-dihydropyran or 2,3-dihydrofuran, is used in an inert solvent such as dichloromethane, in the presence of an acid condensing agent such as p-toluenesulfonic acid or pyridine hydrochloride. The reagent is used in slight excess, preferably 1.0 to 1.2 times theory. The reaction is carried out at about 20°-50° C.

When the blocking group is of the formula

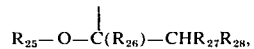

as defined above, the appropriate reagent is a vinyl ether, e.g. isobutyl vinyl ether or any vinyl ether of the formula $R_{25}$-O-C($R_{26}$)=$CR_{27}R_{28}$ wherein $R_{25}$, $R_{26}$, $R_{27}$, and $R_{28}$ are as defined above; or an unsaturated cyclic or heterocyclic compound, e.g. 1-cyclohex-1-yl methyl ether or 5,6-dihydro-4-methoxy-2H-pyran. See C. B. Reese et al., J. Am. Chem. Soc. 89, 3366 (1967). The reaction conditions for such vinyl ethers and unsaturates are similar to those for dihydropyran above.

The lactol CXI is obtained on reduction of the formula-CX lactone without reducing the 13,14-ethylenic group. For this purpose, diisobutylaluminum hydride is used. The reduction is preferably done at −60° to −70° C.

The stereochemistry of the side chain is preserved in transforming CVIII to CIX to CX to CXI. For example, a 3-alpha compound CVIII yields a 3-alpha compound CXI.

Referring to Chart M, the steps are shown whereby compound CXI is transformed to either 3-oxa-$PGF_{1\alpha}$ compounds (CXVI) or 3-oxa-$PGE_1$ compounds (CXVIII). Therein, Q', Q'', $R_1$, $R_2$, and $R_{21}$ are as defined above. $R_{22}$ is either methyl or ethyl, and $R_{23}$ is either hydrogen or a blocking group $R_{21}$.

The formula-CXII compound is obtained from the formula-CXI lactol by the Wittig reaction, with a (carbalkoxymethylene)triphenyl phosphorane, $R_{22}$OOC-CH=P($C_6H_5$)$_3$. The reaction is conveniently carried out at 25° C.

The formula-CXIII compound is then obtained by reduction of the ethylenic group in the carboxyl chain. For this purpose a reducing agent is used which does not reduce the —CH=C(Q'')—$R_2$ group, for example hydrogen in the presence of a catalyst such as palladium on carbon or rhodium on alumina. Mild conditions are sufficient such as low pressure and temperatures of 0° to 40° C.

The formula-CXIV alcohol is obtained from the formula-CXIII compound by reduction, for example with lithium aluminum hydride or lithium trimethoxy aluminum hydride. A solvent such as diethyl ether or tetrahydrofuran is conveniently used.

The formula-CXV compound is obtained by a Williamson synthesis, condensing the formula-CXIV alcohol with a haloacetate, Hal—$CH_2$—$COOR_1$ wherein Hal is chloro, bromo, or iodo and $R_1$ is as above defined, in the presence of a base. For the base, there is used for example, n-butyllithium, phenyllithium, triphenylmethyllithium, sodium hydride, or potassium t-butoxide. When $R_{23}$ is hydrogen it is preferred that only one molecular equivalent of the base be used; when $R_{23}$ is a blocking group excess of the base may be used. The acetate is employed in about 100% excess. Instead of a haloacetic acid ester, a salt, for example lithium chloroacetate is useful. After the condensation, the salt is transformed to the CXV compound by methods known in the art. The condensation is conveniently run in a solvent such as dimethyl formamide, tetrahydrofuran, dimethyl sulfoxide, or hexamethylphosphoramide.

The CXV intermediate is transformed to the formula-CXVI 3-oxa-$PGF_{1\alpha}$ -type product by hydrolysis of the blocking groups, for example in dilute acetic acid, aqueous citric acid, or aqueous phosphoric acid-tetrahydrofuran.

The formula-CXVII $PGE_1$-type compound is obtained by oxidation of the formula CXV-compound, for example by either the Jones or Collins reagents. Thereafter, the blocking groups are removed by hydrolysis to yield the formula-CXVIII 3-oxa-PGE₁-type products. The 3-oxa-PGE₂ compounds encompassed by formula XX and the 3-oxa-PGF₂α compounds encompassed by formula XXX are also prepared by the transformations shown in Chart N. Therein Q', Q'', R₁, R₂, R₂₁, and R₂₂, are as defined above for Charts L and M.

Starting material CXII is provided by the first step of Chart M as shown above. Next, the formula-CXIX alcohol is obtained by reduction, for example with lithium aluminum hydride or lithium trimethoxy aluminum hydride. A solvent such as diethyl ether or tetrahydrofuran is conveniently used. Thereafter, the steps by which the formula-CXXI PGF₂α-type compounds and the formula-CXXIII PGE₂-type compounds are formed are by using the same reagents and conditions employed for preparing the corresponding formula-CXVI PGF₁α-type and formula-CXVIII PGE₁-type compounds represented in Chart M and discussed above.

The 4-oxa-PGF₁α compounds encompassed by formula-XXIX are also prepared by the transformations shown in Chart O. Therein Q', Q'', R₁, R₂, and R₂₁ are as defined above for Charts L and M.

Starting material CXI is provided by the steps of Chart L above. Next, the formula-CXXIV allyl compound is obtained by reaction of the lactol with a Wittig reagent. For a discussion of the conditions of various Wittig reactions, see for example "Organic Reactions", Vol. 14, p. 270, R. Adams et al. edit., Wiley, 1965. The formula-CXXV compound is obtained by methods known in the art or discussed herein. Hydroboration then yields the formula-CXXVI alcohol. See, for example, "Hydroboration", H. C. Brown, W. A. Benjamin, Inc., New York, 1962.

CHART N

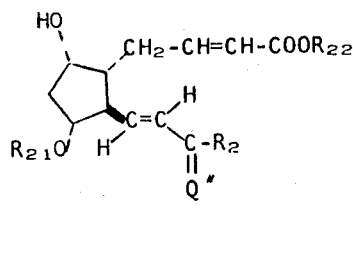

CXII

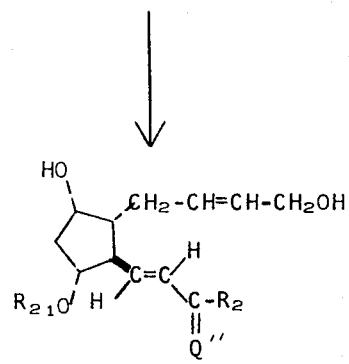

CXIX

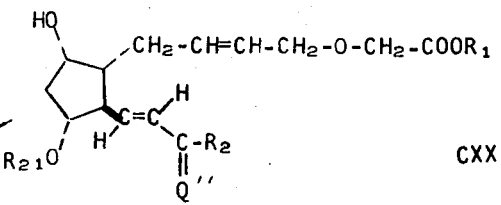

CXX

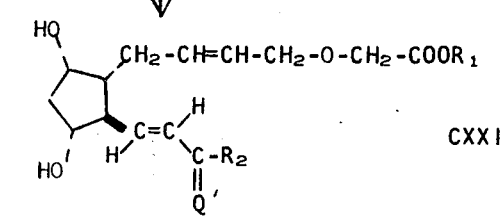

CXXI

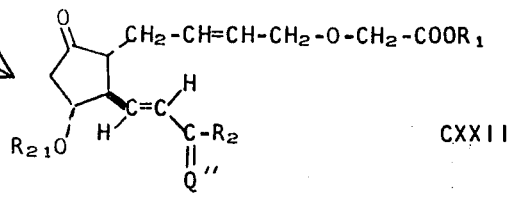

CXXII

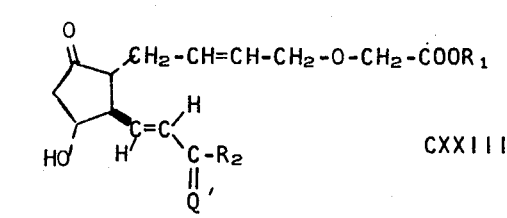

CXXIII

CHART O

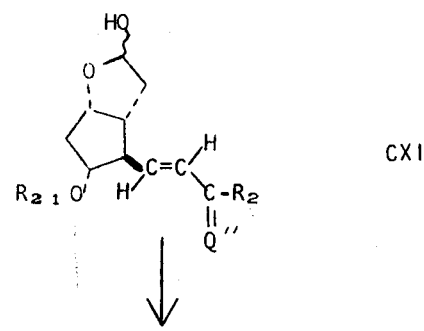

CXI

CHART O continued

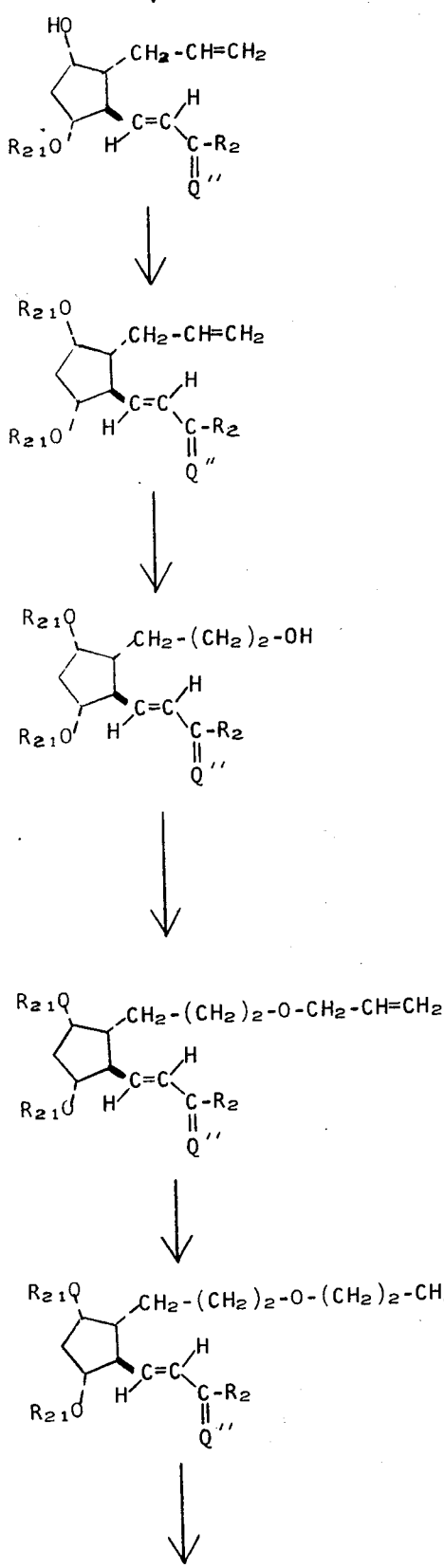

CXXIV

CXXV

CXXVI

CXXVII

CXXVIII

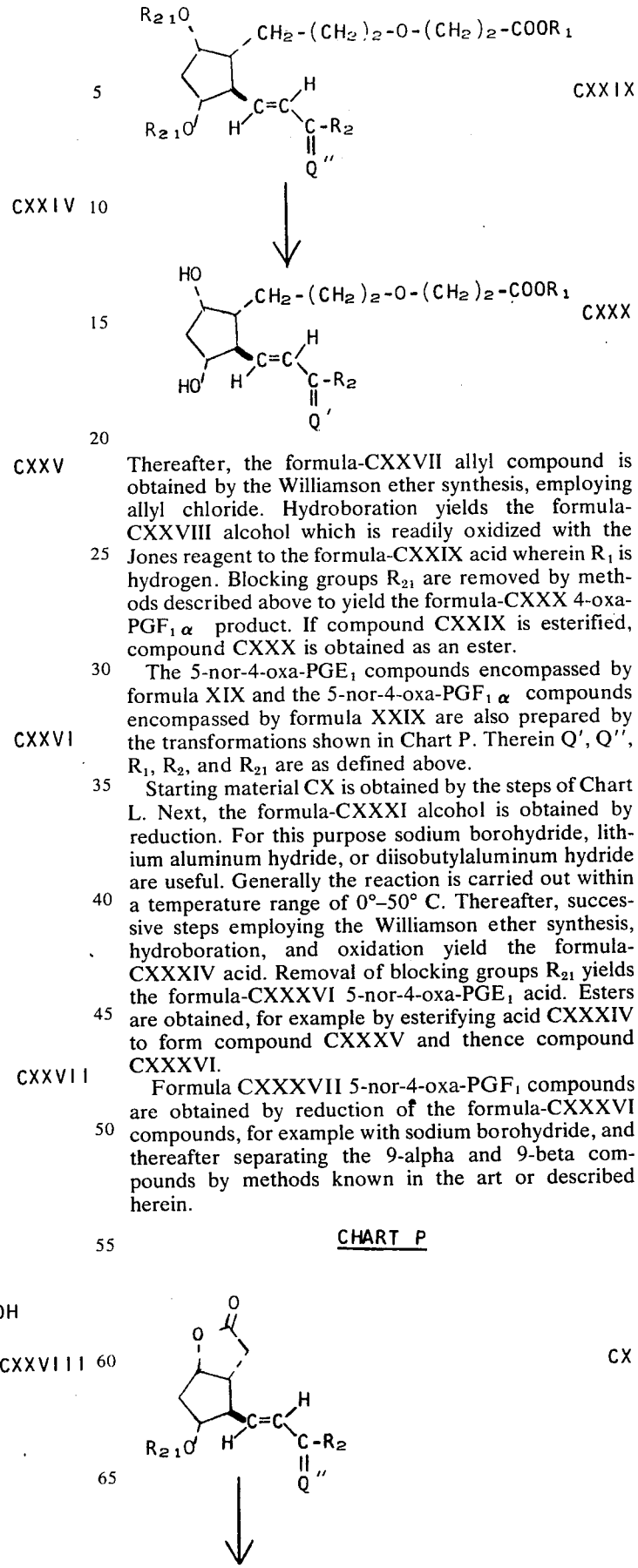

CXXIX

CXXX

CX

Thereafter, the formula-CXXVII allyl compound is obtained by the Williamson ether synthesis, employing allyl chloride. Hydroboration yields the formula-CXXVIII alcohol which is readily oxidized with the Jones reagent to the formula-CXXIX acid wherein $R_1$ is hydrogen. Blocking groups $R_{21}$ are removed by methods described above to yield the formula-CXXX 4-oxa-PGF$_{1\alpha}$ product. If compound CXXIX is esterified, compound CXXX is obtained as an ester.

The 5-nor-4-oxa-PGE$_1$ compounds encompassed by formula XIX and the 5-nor-4-oxa-PGF$_{1\alpha}$ compounds encompassed by formula XXIX are also prepared by the transformations shown in Chart P. Therein Q', Q'', $R_1$, $R_2$, and $R_{21}$ are as defined above.

Starting material CX is obtained by the steps of Chart L. Next, the formula-CXXXI alcohol is obtained by reduction. For this purpose sodium borohydride, lithium aluminum hydride, or diisobutylaluminum hydride are useful. Generally the reaction is carried out within a temperature range of 0°–50° C. Thereafter, successive steps employing the Williamson ether synthesis, hydroboration, and oxidation yield the formula-CXXXIV acid. Removal of blocking groups $R_{21}$ yields the formula-CXXXVI 5-nor-4-oxa-PGE$_1$ acid. Esters are obtained, for example by esterifying acid CXXXIV to form compound CXXXV and thence compound CXXXVI.

Formula CXXXVII 5-nor-4-oxa-PGF$_1$ compounds are obtained by reduction of the formula-CXXXVI compounds, for example with sodium borohydride, and thereafter separating the 9-alpha and 9-beta compounds by methods known in the art or described herein.

CHART P

CHART P continued

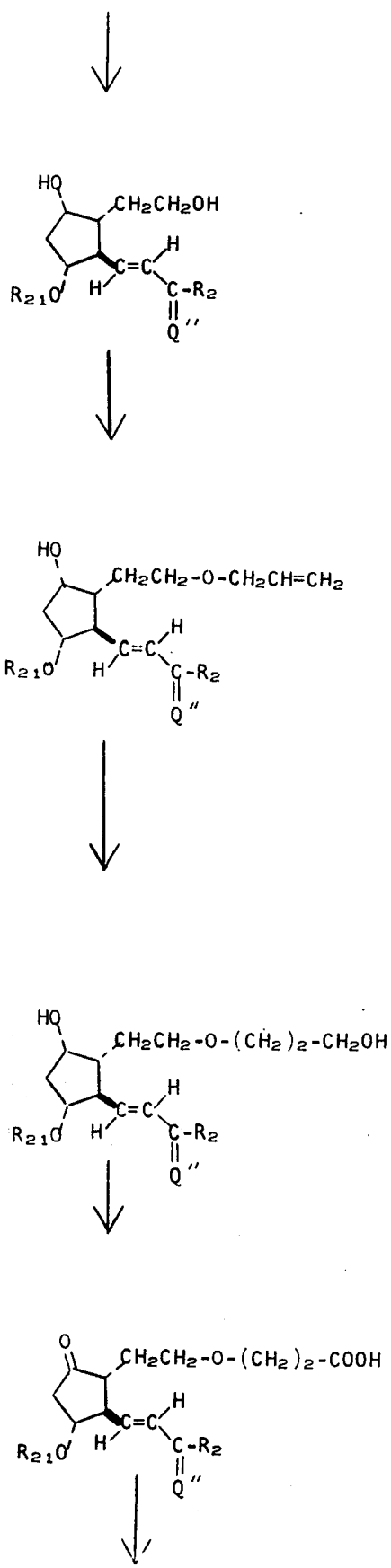

CXXXI

CXXXII

CXXXIII

CXXXIV

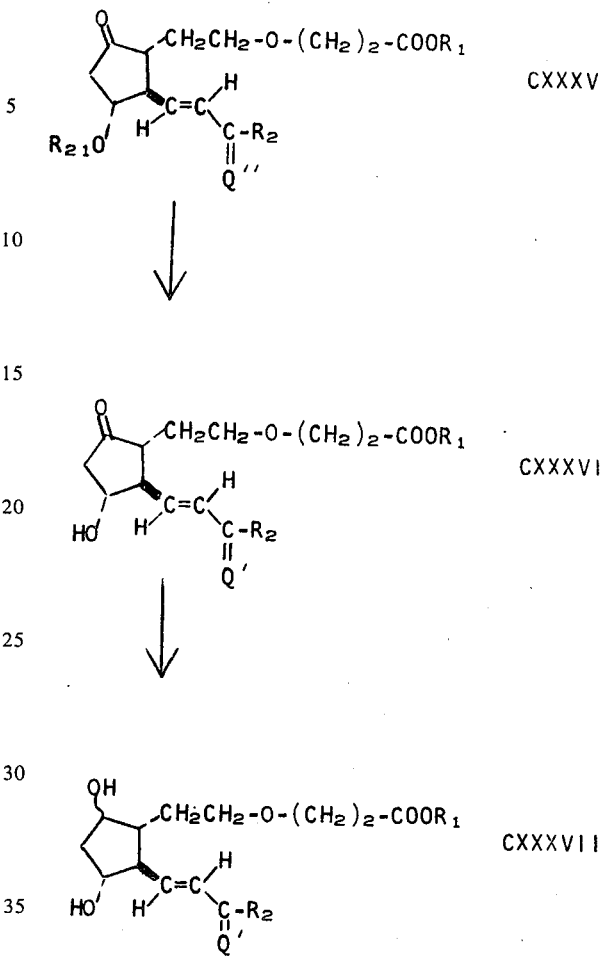

CXXXV

CXXXVI

CXXXVII

The final formula XVIII-to-LVII compounds or their corresponding racemates prepared by the processes of this invention, in free acid form, are transformed to pharmacologically acceptable salts by neutralization with appropriate amounts of the corresponding inorganic or organic base, examples of which correspond to the cations and amines listed above. These transformations are carried out by a variety of procedures known in the art to be generally useful for the preparation of inorganic, i.e., metal or ammonium, salts, amine acid addition salts, and quaternary ammonium salts. The choice of procedure depends in part upon the solubility characteristics of the particular salt to be prepared. In the case of the inorganic salts, it is usually suitable to dissolve the formula XVIII-to-LVII acid in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water or addition of a water-miscible solvent of moderate polarity, for example, a lower alkanol or a lower alkanone, gives the solid inorganic salt if that form is desired.

To produce an amine salt, the formula XVIII-to-LVII acid is dissolved in a suitable solvent of either moderate or low polarity. Examples of the former are ethanol, acetone, and ethyl acetate, Examples of the latter are diethyl ether and benzene. At least a stoichiometric amount of the amine corresponding to the desired cation is then added to that solution. If the resulting salt does not precipitate, it is usually obtained in solid form by addition of a miscible diluent of low polarity or by evaporation. If the amine if relatively volatile, any excess can easily be removed by evaporation. It is preferred to use stoichiometric amounts of the less volatile amines.

Salts wherein the cation is quaternary ammonium are produced by mixing the formula XVIII-to-LVII acid with the stoichiometric amount of the corresponding quaternary ammonium hydroxide in water solution, followed by evaporation of the water.

The final formula XVIII-to-LVII acids or esters or their corresponding racemates prepared by the processes of this invention are transformed to lower alkanoates by interaction of the formula XVIII-to-LVII hydroxy compound with a carboxyacylating agent, preferably the anhydride of a lower alkanoic acid, i.e., an alkanoic acid of one to 8 carbon atoms, inclusive. For example, use of acetic anhydride gives the corresponding diacetate. Similar use of propionic anhydride, isobutyric anhydride, and hexanoic acid anhydride gives the corresponding carboxyacylates.

The carboxyacylation is advantageously carried out by mixing the hydroxy compound and the acid anhydride, preferably in the presence of a tertiary amine such as pyridine or triethylamine. A substantial excess of the anhydride is used, preferably about 10 to about 10,000 moles of anhydride per mole of the hydroxy compound reactant. The excess anhydride serves as a reaction diluent and solvent. An inert organic diluent, for example, dioxane, can also be added. It is preferred to use enough of the tertiary amine to neutralized the carboxylic acid produced by the reaction, as well as any free carboxyl groups present in the hydroxy compound reactant. The carboxyacylation reaction is preferably carried out in the range about 0° to about 100° C. The necessary reaction time will depend on such factors as the reaction temperature, and the nature of the anhydride and tertiary amine reactants. With acetic anhydride, pyridine, and a 25° C. reaction temperature, a 12 to 24-hour reaction time is used.

The carboxyacylated product is isolated from the reaction mixture by conventional methods. For example, the excess anhydride is decomposed with water, and the resulting mixture acidified and then extracted with a solvent such as diethyl ether. The desired carboxyacylate is recovered from the diethyl ether extract by evaporation. The carboxyacylate is then purified by conventional methods, advantageously by chromatography.

By this procedure, the formula XVIII-to-XXVII PGE-type compounds are transformed to dialkanoates, the formula XXVIII-to-XXXVII PGF-type compounds are transformed to trialkanoates, and the formula XXXVIII-to-LVII PGA-type and PGB-type compounds are transformed to monoalkanoates.

When a PGE-type dialkanoate is transformed to a PGF-type compound by carbonyl reduction as shown in Chart A, a PGF-type dialkanoate is formed and is used for the above-described purposes as such or is transformed to a trialkanoate by the above-described procedure. In the latter case, the third alkanoyloxy group can be the same as or different than the two alkanolyoxy groups present before the carbonyl reduction.

The 3-oxa and 4-oxa prostaglandin compounds described herein, as well as most of the intermediates, except for LVIII and LXV, each has at least one center of asymmetry and each can exist in racemic ($dl$) form and in either enantiomeric optically active form i.e., $d$ and $l$. The formulas XVIII to LVII as drawn each represents the optically active form with the same configuration as the naturally-occurring prostaglandins. A formula defining the enantiomer is the mirro image of the formula as drawn. Both formulas are necessary to define accurately the corresponding racemic form. In the charts, only the formulas for one optically active form are shown, but the transformations therein depicted are intended to apply to either enantiomorphic form and also the racemic mixture.

When an optically active ($d$ or $l$) final compound is desired, it is made by resolution of the racemic compound or by use of a resolved asymmetric intermediate. These resolutions are carried out by procedures known in the art. For example, when final compound XVIII to LVII is a free acid, the $dl$ form thereof is resolved into the $d$ and $l$ forms by reacting said free acid by known general procedures with an optically active base, e.g., brucine or strychnine, to give a mixture of two diastereoisomers which are separated by known general procedures, e.g., fractional crystallization, to give the separate diastereoisomeric salts. The optically active acid of formula XVIII to LVII is then obtained by treatment of the salt with an acid by known general procedures.

Another procedure for obtaining optically active 3-oxa and 4-oxa PGF-type compounds is by stereoselective microbiological reduction of the racemic 3-oxa and 4-oxa PGE compounds. For this purpose actively fermenting baker's yeast is employed. The PGE compound is contacted with a yeast-sugar-water mixture at about 25° C. for 24–48 hours. There is produced by reduction a mixture of the $PGF_\alpha$ compound and the enantiomeric $PGF_\beta$ compound, which are separable by silica gel chromatography for example. Accompanying this transformation, carboxylic ester groups are removed by hydrolysis.

Still another method referring to the processes discussed above and especially to Charts E, F, and H, is by resolution of cyclic ketal LIX, olefin LXVI, or glycols LX, LXVII or LXXXV in their free acid form into separate $d$ and $l$ forms. They are then esterified and transformed further to the corresponding optically active form of the final products XVIII to LVII as described above.

Alternatively, bicyclo ketone reactants LX, LXVII, or LXXXV, in exo or endo form, are transformed to ketals with an optically active 1,2-glycol, e.g., D-(−)-2,3-butanediol, by reaction of said 1,2-glycol with the formula LX, LXVII, or LXXXV compound in the presence of a strong acid, e.g., p-toluenesulfonic acid. The resulting ketal is a mixture of diastereoisomers which is separated into the $d$ and $l$ diastereoisomers, each of which is then hydrolyzed with an acid, e.g., oxalic acid, to the original keto compound, now in optically active form. These reactions involving optically active glycols and ketals for resolution purposes are generally known in the art. See, for example, Chem. Ind. 1664 (1961) and J. Am. Chem. Soc. 84, 2938 (1962). Dithiols may be used instead of glycols.

With reference to the processes of charts L, M, N, O, and P, the final optically active 3-oxa and 4-oxa products corresponding to formulas XVIII to LVII are obtained by starting with the proper optically active aldehyde CVI as discussed above. Likewise the corresponding racemic products are obtained by starting with the racemic (*dl*) aldehyde CVI or subsequent racemic intermediate.

DESCRIPTION OF THE PREFERRED EMBODIMENTS

The invention can be more fully understood by the following examples and preparations:

All temperatures are in degrees centigrade.

Infrared absorption spectra are recorded on a Perkin-Elmer Model 421 infrared spectrophotometer. Except when specified otherwise, undiluted (neat) samples are used.

Ultraviolet spectra are recorded on a Cary Model 15 spectrophotometer.

NMR spectra are recorded on a Varian A-60 spectrophotometer on deuterochloroform solutions with tetramethylsilane as an internal standard (downfield).

Mass spectra are recorded on an Atlas CH-4 mass spectrometer with a TO-4 source (ionization voltage 70 ev).

The collection of chromatographic eluate fractions starts when the eluant front reaches the bottom of the column.

"Brine", herein, refers to an aqueous saturated sodium chloride solution.

The A-IX solvent system used in thin layer chromatography is made up from ethyl acetate-acetic acid-2,2,4-trimethylpentane-water (90:20:50:100) according to M. Hamberg and B. Samuelsson, J. Biol. Chem. 241, 257 (1966).

"Skellysolve-B" refers to mixed isomeric hexanes.

Silica gel chromatography, as used herein, is understood to include elution, collection of fractions, and combination of those fractions shown by TLC (thin layer chromatography) to contain the desired product free of starting material and impurities

PREPARATION 1

Endo-bicyclo[3.1.0]hexan-3ol-6-carboxylic acid methyl ester

A mixture of endo-bicyclo[3.1.0]hex-2-ene-6-carboxylic acid methyl ester (103 g.) and anhydrous diethyl ether (650 ml.) is stirred under nitrogen and cooled at −5° C. A one molar solution (284 ml.) of diborane in tetrahydrofuran is added dropwise during 30 minutes while keeping the temperature below 0° C. The resulting mixture is then stirred and allowed to warm to 25° C. during 3 hrs. Concentration under reduced pressure gives a residue which is dissolved in 650 ml. of anhydrous diethyl ether. The solution is cooled to 0° C., and 3 N. aqueous sodium hydroxide solution (172 ml.) is added dropwise under nitrogen and with vigorous stirring during 15 min., keeping the temperature at 0° to 5° C. Next, 30% aqueous hydrogen peroxide (94 ml.) is added dropwise with stirring during 30 min. at 0° to 5° C. The resulting mixture is stirred an hour while warming to 25° C. Then, 500 ml. of brine is added, and the diethyl ether layer is separated. The aqueous layer is washed with four 200 ml. portions of ethyl acetate, the washings being added to the diethyl ether layer, which is then washed with brine, dried, and concentrated to give 115 g. of residue. This residue is distilled under reduced pressure to give 69 g. of a mixture of the methyl esters of endo-bicyclo[3.1.0]hexan-3-ol-6-carboxylic acid and endo-bicyclo[3.1.0]hexan-2-ol-6-carboxylic acid; b.p. 86°–95° C. at 0.5 mm.

PREPARATION 2

Endo-bicyclo[3.1.0]hexan-3-ol-6-carboxylic acid methyl ester tetrahydropyranyl either The 2-ol and 3-ol mixture (66 g.) obtained according to Preparation 1 in 66 ml. of dihydropyran is stirred and cooled at 15°–20° C. during addition of 3 ml. of anhydrous diethyl ether saturated with hydrogen chloride. The temperature of the mixture is then kept in the range 20° to 30° C. for one hour with cooling, and is then kept at 25° for 15 hrs. Concentration gives a residue which is distilled under reduced pressure to give 66 g. of a mixture of the methyl esters-tetrahydropyranyl ethers of endo-bicyclo[3.1.0]hexan-3-ol-6-carboxylic acid and endo-bicyclo[3.1.0]hexan-2-ol-6-carboxylic acid; b.p. 96°–104° C. at 0.1 mm.

PREPARATION 3

Endo-6-hydroxymethylbicyclo[3.1.0]hexan-3-ol-3-tetrahydropyranyl ether

A solution of the mixture (69 g.) of products obtained according to Preparation 2 in 300 ml. of anhydrous diethyl ether is added dropwise during 45 min. to a stirred and cooled mixture of lithium aluminum hydride (21 g.) in 1300 ml. of anhydrous diethyl ether under nitrogen. The resulting mixture is stirred 2 hrs. at 25° C., and is then cooled to 0° C. Ethyl acetate (71 ml.) is added, and the mixture is stirred 15 min. Water (235 ml.) is then added, and the diethyl ether layer is separated. The water layer is washed twice with diethyl ether and twice with ethyl acetate. A solution of Rochelle salts is added to the aqueous layer, which is then saturated with sodium chloride and extracted twice with ethyl acetate. All diethyl ether and ethyl acetate solutions are combined, washed with brine, dried and concentrated to give 61 g. of a mixture of the 3-tetrahydropyranyl ethers of endo-6-hydroxymethylbicyclo[3.1.0]hexan 3-ol and endo-6-hydroxymethylbicyclo[3.1.0]hexan-2-ol.

PREPARATION 4:

Endo-bicyclo[3.1.0]hexan-3-ol-6-carboxaldehyde 3-tetrahydropyranyl ether

A solution of the mixture (34 g.) of products obtained according to Preparation 3 in 1000 ml. of acetone is cooled to −10° C. Jones reagent (75 ml. of a solution of 21 g. of chromic anhydride, 60 ml. of water, and 17 ml. of concentrated sulfuric acid), precooled to 0° C., is added dropwise with stirring during 10 min. at −10° C. After 10 min. of additional stirring at −10° C., isopropyl alcohol (35 ml.) is added during 5 min., and stirring is continued for 10 min. The reaction mixture is then poured into 8 l. of an ice and water mixture. The resulting mixture is extracted 6 times with dichloromethane. The combined extracts are washed with aqueous sodium bicarbonate solution, dried, and concentrated to give 27 g. of a mixture of the tetrahydropyranyl ethers of endo-bicyclo[3.1.0]hexane-3-ol-6-carboxaldehyde and endo-bicyclo[3.1.0]hexane-2-ol-6-carboxaldehyde.

PREPARATION 5:

Endo-6-(cis-and trans-1-heptenyl-bicyclo[3.1.0]hexan-3-ol tetrahydropyranyl ether Refer to Chart G. A mixture of hexyl bromide (100 g.). triphenylphosphine (160 g.), and toluene (300 ml.) is stirred and heated at reflux for 7 hrs. The mixture is then cooled to 10° C., and the crystals which separate are collected by filtration, washed with toluene, and dried to give 147 g. of hexyltriphenylphosphonium bromide; m.p. 197°–200° C.

A mixture of hexyltriphenylphosphonium bromide (102 g.) and benzene (1200 ml.) is stirred under nitrogen during addition of a solution of butyl lithium in hexane (146 ml. of a 15% solution-w/v). The resulting mixture is stirred 30 min. Then a solution of the mixture (27 g.) of products obtained according to Preparation 4 in 300 ml. of benzene is added dropwise with stirring during 30 min. The mixture is heated and stirred at 70° C. for 2.5 hrs., and then is cooled to 25° C. The resulting precipitate is collected by filtration and washed with benzene. The filtrate and benzene wash are combined, washed with water, and dried to give 58 g. of a mixture of the tetrahydropyranyl ethers of endo-6-(cis- and trans-1-heptenyl)bicyclo[3.1.0-]hexan-3-ol and endo-6-(cis- and trans-1-heptenyl)-bicyclo[3.1.0]hexan-2-ol.

PREPARATION 6:

Endo-6-(cis- and trans-1-heptenyl)-bicyclo[3.1.0]hexan-3-ol

Refer to Chart G. Oxalic acid (3 g.) is added to a solution of the mixture (58 g.) of products obtained according to Preparation 5 in 1500 ml. of methanol. The mixture is heated under reflux with stirring for 1.5 hrs. Concentration under reduced pressure gives an oil which is dissolved in dichloromethane. That solution is washed with aqueous sodium bicarbonate solution, dried, and concentrated under reduced pressure. The residue is dissolved in an isomeric hexane mixture (Skellysolve B), and chromatographed on 600 g. of wet-packed silica gel. The column is eluted with 2 l. of Skellysolve B, and then successively with 1 l. of 2.5%, 2 l. of 5%, 2 l. of 7.5%, 5 l. of 10%, and 3 l. of 15% ethyl acetate in Skellysolve B. Concentration of the combined fractions corresponding to the 10% and 15% ethyl acetate gives 16 g. of a mixture of endo-6-(cis- and trans-1-heptenyl)bicyclo[3.1.0]hexan-3-ol and endo-6-(cis- and trans-1-heptenyl)bicyclo[3.1.0]hexan-2-ol.

PREPARATION 7:

Endo-6-(cis- and trans-1-heptenyl)-bicyclo[3.1.0]hexan-3-one (Formula LXV: $R_2$ is pentyl, and ~ is endo)

Refer to Chart G. A solution of the mixture (15 g.) of products obtained according to Preparation 6 in 450 ml. of acetone is cooled to −10° C. and stirred while adding 30 ml. of Jones reagent (Preparation 4) dropwise during 10 min. The resulting mixture is stirred 10 min. at −10° C. Then, isopropyl alcohol (15 ml.) is added and stirring is continued for 10 min. The mixture is poured into 2400 ml. of water. The water is extracted 5 times with dichloromethane. The combined extracts are washed with aqueous sodium bicarbonate solution, dried, and concentrated to give an oil. The oil is chromatographed on 500 g. of silica gel wet-packed with isomeric hexanes (Skellysolve B), eluting successively with 2 l. of Skellysolve B, 2 l. of 2.5% ethyl acetate in Skellysolve B, and 10 l. of 5% ethyl acetate in Skellysolve B. The first 1.5 l. of the 5% ethyl acetate in Skellysolve B eluate is concentrated to give 5.9 g. of the title compound; $R_f$ 0.62 on thin layer chromatography with silica gel plates developed with 20% ethyl acetate in cyclohexane.

Following the procedures of Preparations 5, 6, and 7, but using in Preparation 5 butyl bromide, pentyl bromide, heptyl bromide, and octyl bromide in place of hexyl bromide, there are obtained the 1-pentenyl, 1-hexenyl, 1-octenyl, and 1-nonenyl compounds corresponding to the product of Preparation 7.

Also following the procedures of Preparations 5, 6, and 7, but using in Preparation 5, primary bromides of the formula X—$(CH_2)_d$—$CH_2Br$, wherein d is one, 2, 3, or 4, and X is isobutyl, tert-butyl, 3,3-difluorobutyl, 4,4-difluorobutyl, 4,4,4-trifluorobutyl, and 3,3,4,4,4-pentafluorobutyl, in place of hexyl bromide, there are obtained compounds corresponding to the product of Preparation 7 with X—$(CH_2)_d$—CH=CH—in place of the 1-heptenyl moiety.

Also following the procedures of Preparations 5, 6, and 7 but using in Preparation 5 the other bromides of the formula

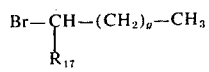

wherein g and $R_{17}$ are as defined above in place of hexyl bromide, there are obtained compounds corresponding to the products of Preparation 7 with

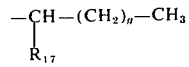

in place of the 1-heptenyl moiety.

Also following the procedures of Preparations 5, 6, and 7 but using in Preparation 5, exo-bicyclo[3.1.0-]hexane reactants in place of each of the endo reactants defined in Preparation 5 and after Preparation 7, the exo compounds corresponding to the endo product of Preparation 7 and each of the endo products defined after Preparation 7 are obtained. The necessary exo bicyclo[3.1.0]hexane reactants are prepared as described in Belgian Pat. No. 702,477.

By the above-described procedures, each of the reactants encompassed by formula LXV, above, is prepared.

PREPARATION 8:

Endo-6-(1-2-dihydroxyheptyl)-bicyclo[3.1.0]hexan-3-one (Formula LXXIII $R_2$ is pentyl, and ~ is endo)

Refer to Chart G. A solution of potassium chlorate (1.0 g.) and osmium tetroxide (0.065 g.) in 25 ml. of water is added with stirring to a solution of the product (1.0 g.) of Preparation 7. The mixture is stirred vigorously for 5 hrs. at 50° C. Then, the nearly colorless mixture is concentrated under reduced pressure. The residue is extracted repeatedly with dichloromethane, and the combined extracts are dried and concentrated to give 1.2 g. of a dark oil. This oil is chromatographed on 100 g. of silica gel, and eluted successively with 300 ml. of 10% ethyl acetate in a mixture of isomeric hexanes (Skellysolve B), with 500 ml. of 25% ethyl acetate in Skellysolve B, and then with 50% ethyl acetate in Skellysolve B, collecting 100 ml. eluate fractions. Fractions 13–19 (50% ethyl acetate) were combined and concentrated to give 867 mg. of the title compound.

Following the procedure for Preparation 8 but using as reactants the endo and the exo 1-pentenyl, 1-hexenyl, 1-octenyl, and 1-nonenyl compounds corresponding to the 1-heptenyl bicyclo[3.1.0]hexane reactant of Preparation 8, the corresponding endo and exo 1,2-dihydroxypentyl, 1,2-dihydroxyhexyl, 1,2-dihydroxyoctyl, and 1,2-dihydroxynonyl bicyclo[3.1.0]hexane products are obtained.

Also following the procedure of Preparation 8 but using as reactants the endo and the exo compounds with $X—(CH_2)_d—CH=CH—$ in place of the 1-heptenyl moiety of the reactant of Preparation 8, the corresponding $X—(CH_2)_d—CHOH—CHOH—$ bicyclo[3.1.0]hexane products are obtained.

Also following the procedure of Preparation 8 but using as reactants, endo and exo bicyclo[3.1.0]hexane compounds of the formula

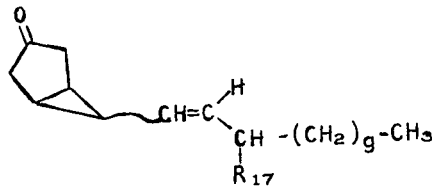

wherein $g$ and $R_{17}$ are as defined above, those compounds being prepared as described above, the corresponding

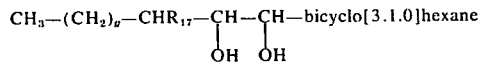

products are obtained.

PREPARATION 9:

Endo-6-(1,2-dihydroxyheptyl)-bicyclo[3.1.0]hexan-3-one acetonide (Formula LVIII: $R_2$ is pentyl, $R_{11}$ and $R_{12}$ are methyl, ~ is endo)

Refer to Chart G. A solution of the product (8.41 g.) of Preparation 8 and 700 mg. of potassium bisulfate in 140 ml. of acetone is stirred at 25° C. for 64 hrs. Then, sodium carbonate monohydrate (710 mg.) is added, and the mixture is stirred 10 min. The acetone is evaporated at reduced pressure, and water is added. The aqueous solution is extracted repeatedly with dichloromethane, and the extracts are combined, washed with water, dried, and concentrated to give 9.3 g. of an oil. The oil is chromatographed on 400 g. of silica gel, being eluted with 2 l. of 10% ethyl acetate in Skellysolve B, and then with 4 l. of 15% ethyl acetate in Skellysolve B. The 15% ethyl acetate eluates are concentrated to give 7.4 g. of the title compound; infrared absorption at 3000, 1745, 1370, and 1045 cm$^{-1}$; NMR peaks at 4.2–3.8 (multiplet), 3.5 (doublet), 2.9–2.0 (multiplet), 1.25 (singlet), and 0.91 (triplet) δ.

Following the procedure of Preparation 9 but using as reactants the exo 1,2-dihydroxyheptyl, the endo and the exo 1,2-dihydroxypentyl, 1,2-dihydroxyhexyl, 1,2-dihydroxyoctyl, and 1,2-dihydroxynonyl compounds corresponding to the 1,2-dihydroxyheptyl bicyclo[3.2.1]hexane reactant of Preparation 9, the corresponding acetonides are obtained.

Also following the procedure of Preparation 9 but using as reactants the endo and exo compounds with $X—(CH_2)_d—CHOH—CHOH—$ in place of the 1,2-dihydroxyheptyl moiety of the reactant of Preparation 9, the corresponding acetonides are obtained.

Also following the procedure of Preparation 9 but using as reactants the endo and exo compounds with

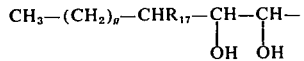

in place of the 1,2-dihydroxyheptyl of the reactant of Preparation 9, the corresponding acetonides are obtained.

EXAMPLE 1:

dl-Ethyl 3-oxa-7-[endo-6-(1-heptenyl)-3-oxobicyclo-[3.1.0]hex-2α-yl]heptanoate (Formula LXVI: $R_2$ is pentyl, $R_{10}$ is ethyl, Z is $—(CH_2)_3OCH_2—$, ~ is endo)

Refer to Chart F. A solution of potassium tertbutoxide (8.8 g.) in 500 ml. of nitrogen-purged tetrahydrofuran is added during 45 min. to a stirred solution of endo-6-(1-heptenyl)-bicyclo[3.1.0]hexan-3-one (10.0 g., the product of Preparation 7) and ethyl 7-iodo-3-oxaheptanoate (42.6 g.) in 250 ml. of tetrahydrofuran under nitrogen at 25° C. The resulting mixture is acidified at once with 120 ml. of 5% hydrochloric acid, and then is concentrated under reduced pressure below 40° C. to remove most of the tetrahydrofuran. Water (400 ml.) is added to the residue, and the mixture is extracted with three 400-ml. portions of ethyl acetate. The combined extracts are washed successively with aqueous sodium thiosulfate solution and brine, dried, and concentrated under reduced pressure. The residue (46.5 g.) is chromatographed over 4 kg. of silica gel wet-packed with 8 l. of 5% ethyl acetate in a mixture of isomeric hexanes (Skellysolve B), eluting with 8 l. each of 5–10%, 10–15%, 15–20%, and 20–25% ethyl acetate in Skellysolve B (gradients), then with 2 l. 30%, 2 l. 35%, and 2 l. 40% ethyl acetate in Skellysolve B, and finally with 4 l. of 50–100% ethyl acetate in Skellysolve B (gradient), collecting 400-ml. fractions. TLC with 20% ethyl acetate in Skellysolve B shows which fractions contain only the desired alkylation product. Those fractions are combined and concentrated to give 4.7 g. of the title compound; NMR peaks at 4.7–5.9 (multiplet), 4.21 (quartet), 4.05 (singlet), and 3.57 (triplet) δ. A small amount of the corresponding 2β-yl isomer is isolated in later chromatographic fractions.

EXAMPLE 2:

dl-Ethyl 2,2-dimethyl-3-oxa-7-[exo-6-(1-heptenyl)-3-oxobicyclo[3.1.0]hex-2-yl]heptanoate (Formula LXVI: $R_2$ is pentyl, $R_{10}$ is ethyl, Z is $—(CH_2)_3OC(CH_3)_2—$, ~ is endo)

Refer to Chart F. A solution of potassium tertbutoxide (3.8 g.) in 1000 ml. of nitrogen-purged tetrahydrofuran is added during 70 min. to a stirred solution of exo-6-(1-heptenyl)-bicyclo[3.1.0]hexan-3-one (5.0 g.) and ethyl 2,2-dimethyl-7-iodo-3-oxaheptanoate in 500 ml. of anhydrous tetrahydrofuran under nitrogen at 0° C. The resulting mixture is acidified with 50 ml. of 5% hydrochloric acid and then concentrated under reduced pressure below 40° C. to remove most of the tetrahydrofuran. Water (400 ml.) is added to the residue, and the mixture is extracted repeatedly with ethyl acetate. The combined extracts are washed successively with aqueous sodium thiosulfate solution and brine, dried, and concentrated under reduced pressure. The residue (25.5 g.) is chromatographed on a column prepared by wet-packing 2 kg. of silica gel with 4 l. of 5% ethyl acetate in Skellysolve B, eluting with 8 l. of a 5 to 22.5% ethyl acetate gradient in Skellysolve B. TLC with 10% ethyl acetate shows which fractions contain the desired alkylation products. Those fractions are combined and concentrated to give, separately, 1.1 g. of dl-ethyl 2,2-dimethyl-3-oxa-7-[exo-6-(1-heptenyl)-3-oxobicyclo[3.1.0]hex-2α-yl]heptanoate and 0.75 g. of the corresponding beta isomer, dl-ethyl 2,2-dimethyl-3-oxa-7-[exo-6-(1-heptenyl)-3-oxobicyclo[3.1.0]hex-2β-yl]heptanoate.

Following the procedures of Examples 1 or 2, but using in place of the bicyclo[3.1.0]hexane reactant, each of endo and exo forms of the various formula-LXV bicyclo[3.1.0]-hexane reactants whose preparation is described following Preparation 7, for example, formula-LXV bicyclo compounds wherein $R_2$ is propyl, butyl, hexyl, or heptyl, or wherein $R_2$ is $-(CH_2)_d-X$ wherein $d$ is 0, 1, 2, 3, or 4, and X is isobutyl, tert-butyl, 3,3-difluorobutyl, 4,4-difluorobutyl, 4,4,4-trifluorobutyl, or 3,3,4,4,4-pentafluorobutyl, or wherein $R_2$ is $-CHR_{17}-(CH_2)_g-CH_3$ wherein $g$ is one, 2, 3, 4, or 5, those being prepared as described above, there are obtained alpha and beta exo and endo compounds corresponding to the products of Examples 1 and 2 with one of these $R_2$ moieties in place of the pentyl moiety (the $R_2$ portion of 1-heptenyl) of those products. As for Example 1, with excess base and a longer reaction time, these alternative products contain substantial amounts of the corresponding beta isomer which is separated from the alpha isomer as described above.

Also following the procedure of Examples 1 and 2, but using in place of the iodo alkylating agents of those Examples, ethyl 7-iodo-4-oxaheptanoate, ethyl 7-iodo-3-oxa-5-heptynoate, and ethyl 8-iodo-4-oxa-6-octynoate, there are obtained alpha and beta exo and endo compounds corresponding to the products of Examples 1 and 2 with $-(CH_2)_3OCH_2CH_2COOEt$, $-CH_2C\equiv CCH_2OCH_2COOEt$, and $-CH_2C\equiv CCH_2OCH_2CH_2COOEt$, respectively, wherein Et is ethyl, in place of the $-(CH_2)_4OCH_2COOEt$ and $-(CH_2)_4OC(CH_3)_2COOEt$ moieties of the products of Examples 1 and 2. As described above, both alpha and beta products are so obtained. In the same manner but using, according to Examples 1 and 2, other esters of the Example 1 and 2 alkylating agents and of the other above-mentioned alkylating agents within the scope of $R_{10}$ as above-defined, e.g., the methyl, isopropyl, tert-butyl, octyl, cyclohexyl, benzyl, and phenyl esters, there are obtained the corresponding esters of the alpha and beta bicyclo[3.1.0]hexane alkylation products.

Also following the procedure of Examples 1 and 2 but using in combination each of the above-described alternative formula-LXV bicyclo[3.1.0]hexane reactants and each of the above-described alternative omega-halo alkylation reactants, there are obtained formula-LXVI compounds corresponding to the products of Examples 1 and 2 but different therefrom with respect to both the carboxylate-terminated side chain and the side chain attached to the cyclopropane ring of the product.

Also following the procedure of Examples 1 and 2, but using in place of the iodo alkylating agents of those Examples, each of the other alkylating agents within the scope of $Hal-CH_2-Z-COOR_{10}$ as above defined, i.e., alkylating agents of formulas LXXV, LXXVI, LXXVII, and LXXVIII as above-described, there are obtained alpha and beta exo and endo compounds corresponding to the products of Examples 1 and 2 with each of the other $-CH_2-Z-COOR_{10}$ side chains in place of the $-(CH_2)_4OCH_2COOEt$ and $-(CH_2)_4OC(CH_3)_2COOEt$ side chains of the Example 1 and 2 products. For example, using as alkylating agents in the Example 1 and 2 procedure, $I(CH_2)_4OCH(CH_3)COOEt$, $ICH(CH_3)-(CH_2)_3OCH_2COOEt$, $I(CH_2)_3OCH_2COOEt$, $I(CH_2)_5OCH_2COOEt$, $ICH_2CH(CH_3)CH_2CH_2OCH_2COOEt$, $ICH_2CH_2C(CH_2CH_3)_2CH_2OCH_2COOEt$, $I(CH_2)_3C(CH_3)_2OCH_2COOEt$, $I(CH_2)_3OCH_2CH_2COOEt$, $I(CH_2)_2OCH_2CH_2COOEt$, $I(CH_2)_4OCH_2CH_2COOEt$, $I(CH_2)_3OCH(CH_3)CH_2COOEt$, $I(CH_2)_3OC(CH_3)_2CH_2COOEt$, $I(CH_2)_3OCH_2C(CH_3)_2COOEt$, $ICH(CH_3)CH_2CH_2OCH_2CH_2COOEt$, $ICH_2CH(CH_3)CH_2OCH_2CH_2COOEt$, $ICH_2CH_2C(CH_3)_2OCH_2CH_2COOEt$, $ICH_2C(CH_2CH_3)_2CH_2OCH_2COOEt$, $ICH_2C\equiv CCH_2OCH_2COOEt$, $ICH(CH_3)C\equiv CCH_2OCH_2COOEt$, $ICH_2C\equiv CCH_2OCH_2COOEt$, $ICH_2C\equiv CCH_2OCH(CH_3)COOEt$, $ICH_2C\equiv CCH_2OC(CH_3)_2COOEt$, $ICH_2C\equiv CCH(CH_3)OCH_2COOEt$, $ICH_2C\equiv CC(CH_3)_2OCH_2COOEt$, $ICH_2C\equiv CCH_2OCH_2CH_2COOEt$, $ICH(CH_3)C\equiv CCH_2OCH_2CH_2COOEt$, $ICH_2C\equiv CCH_2CH_2OCH_2COOEt$, $ICH_2C\equiv CCH_2OCH(CH_3)CH_2COOEt$, $ICH_2C\equiv CCH_2OC(CH_3)_2CH_2COOEt$, $ICH_2C\equiv CCH(CH_3)OCH_2CH_2COOEt$, $ICH_2C\equiv CC(CH_3)_2OCH_2CH_2COOEt$, $ICH_2C\equiv CCH_2OCH_2C(CH_3)_2COOEt$ there are obtained exo and endo alpha and beta alkylated bicyclo[3.1.0]hexanes each having a carboxylate-terminated side chain corresponding to one of the above specific omegaiodo alkylating agents. For example, the side chain will be alpha or beta $-(CH_2)_4OCH(CH_3)COOEt$ when the alkylating agent is $I(CH_2)_4OCH(CH_3)COOEt$.

Also following the procedure for Examples 1 and 2, but using in combination each of the alternative alkylating agents within the scope of $Hal-CH_2-Z-COOR_{10}$, including the specific examples of those just mentioned, and each of the above-described formula-LXV alternative bicyclo[3.1.0]-hexane reactants, there are obtained formula-LXVI exo and endo alpha and beta compounds corresponding to the products of Examples 1 and 2 but different therefrom with respect to both the carboxylate-terminated side chain and the side chain attached to the cyclopropane ring of the product. In the same manner, alternative alkylating agents within the scope of $Hal-CH_2-Z-COOR_{10}$ wherein $R_{10}$ is other than ethyl, e.g., methyl, isopropyl, tert-butyl, octyl, cyclohexyl, benzyl, and phenyl, are used.

EXAMPLE 3 dl-Ethyl 3-oxa-7-[endo-6-(1,2-dihydroxyheptyl)-3-oxobicyclo[3.1.0]hex-2α-yl]heptanoate Acetonide (Formula LIX: $R_2$ is pentyl, $R_{11}$ and $R_{12}$ are methyl, V is —$(CH_2)_3OCH_2$—, ~ is endo).

Refer to Chart E. Following the procedure of Example 1, endo-6-(1,2-dihydroxyheptyl)-bicyclo[3.1.0]hexan-3-one acetonide (Preparation 9) is alkylated with ethyl 7-iodo-3-oxaheptanoate to give the title compound.

Following the procedure of Example 3 but using in place of the bicyclo[3.1.0]hexane acetonide reactant, each of the exo and endo forms of the various formula-LVIII bicyclo-[3.1.0]hexane cyclic ketals whose preparation is described following Preparation 9, for example, formula-LVIII bicyclo acetonides wherein $R_2$ is propyl, butyl, hexyl, or heptyl, or wherein $R_2$ is —$(CH_2)_d$—X wherein $d$ is zero, one, 2, 3, or 4, and X is isobutyl, tert-butyl, 3,3-difluorobutyl, 4,4-difluorobutyl, 4,4,4-trifluorobutyl, or 3,3,4,4,4-pentafluorobutyl, or wherein $R_2$ is —$CHR_{17}$—$(CH_2)_g$—$CH_3$ wherein $g$ and $R_{17}$ are as defined above, those being prepared as described above, there are obtained alpha and beta exo and endo compounds corresponding to the product of Example 3 with one of these $R_2$ moieties in place of the pentyl moiety of that product.

Also following the procedure of Example 3, but using in place of ethyl 7-iodo-3-oxaheptanoate, ethyl 7-iodo-4-oxaheptanoate, ethyl cis-7-iodo-3-oxa-5-heptenoate, ethyl trans-7-iodo-3-oxa-5-heptenoate, ethyl cis-8-iodo-4-oxa-6-octenoate, ethyl trans-8-iodo-4-oxa-6-octenoate, ethyl 7-iodo-3-oxa-5-heptynoate, and ethyl 8-iodo-4-oxa-6-octynoate, there are obtained alpha and beta exo and endo compounds corresponding to the product of Example 3 with —$(CH_2)_3OCH_2CH_2COOEt$, cis- and trans- —$CH_2CH=CHCH_2OCH_2COOEt$, cis- and trans- -$CH_2CH=CHCH_2OCH_2CH_2COOEt$, —$CH_2C \equiv CCH_2OCH_2COOEt$, and —$CH_2C \equiv CCH_2OCH_2CH_2COOEt$, respectively, wherein Et is ethyl, in place of the —$(CH_2)_4OCH_2COOEt$ moiety of the Example 3 product. As described above, both alpha and beta products are so obtained. In the same manner but using, according to Example 3, other esters of the Example 3 alkylating agent and of the other above-mentioned alkylating agents within the scope of $R_{10}$ as above-defined, e.g., the methyl, isopropyl, tert-butyl, octyl, cyclohexyl, benzyl, and phenyl esters, there are obtained the corresponding esters of these alpha and beta exo and endo bicyclo[3.1.0]hexane cyclic ketal alkylation products.

Also following the procedure of Example 3 but using in combination each of the above-described alternative formula XLV bicyclo[3.1.0]hexane cyclic ketal reactants and each of the above-described omega-halo alkylation reactants, there are obtained formula-LIX compounds corresponding to the product of Example 3 but different therefrom with respect to both the carboxylate-terminated side chain and the side chain attached to the cyclopropane ring of the product.

Also following the procedure of Example 3, but using in place of the ethyl 7-iodo-3-oxaheptanoate, each of the other alkylating agents within the scope of Hal—$CH_2$—V—$COOR_{10}$, as above defined, i.e., alkylating agents of formulas LXXV to LXXXII, inclusive, as above-described, there are obtained formula-LIX alpha and beta products corresponding to the product of Example 3 with each of the other —$CH_2$—V—$COOR_{10}$ side chains in place of the —$(CH_2)_4OCH_2COOEt$ side chain of the Example 3 product. For example, using as alkylating agents in the Example 3 procedure, the cis and the trans isomer of the following: $ICH_2CH=CHCH_2OCH_2COOEt$, $ICH(CH_3)CH=CHCH_2OCH_2COOEt$, $ICH_2CH=CHCH_2CH_2OCH_2COOEt$, $ICH_2CH=CHCH_2OCH(CH_3)COOEt$, $ICH_2CH=CHCH_2OC(CH_3)_2COOEt$, $ICH_2CH=CHCH(CH_3)OCH_2COOEt$, $ICH_2CH=CHC(CH_3)_2OCH_2COOEt$, $ICH_2CH=CHCH_2OCH_2CH_2COOEt$, $ICH(CH_3)CH=CHCH_2OCH_2CH_2COOEt$, $ICH_2CH=CHCH_2CH_2OCH_2CH_2COOEt$, $ICH_2CH=CHCH_2OCH(CH_3)CH_2COOEt$, $ICH_2CH=CHCH_2OC(CH_3)_2CH_2COOEt$, $ICH_2CH=CHCH(CH_3)OCH_2CH_2COOEt$, $ICH_2CH=CHC(CH_3)_2OCH_2CH_2COOEt$, $ICH_2CH=CHCH_2OCH_2C(CH_3)_2COOEt$ and also the list of specific saturated and acetylenic 3-oxa and 4-oxa omega-iodo ethyl esters given above, there are obtained formula-LIX alpha and beta alkylated bicyclo[3.1.0]hexane cyclic ketals each having a carboxylate-terminated side chain corresponding to one of these specific omega-iodo alkylating agents. For example, the side chain will be alpha or beta —$(CH_2)_4OCH(CH_3)COOEt$ when the alkylating agent is $I(CH_2)_4OCH(CH_3)COOEt$.

Also following the procedure of Example 3, but using in combination each of the alternative alkylating agents within the scope of Hal—$CH_2$—Z—$COOR_{10}$, including the specific examples of those just mentioned, and each of the above-described alternative formula-LVIII bicyclo[3.1.0]hexane cyclic ketal reactants, there are obtained formula-LIX exo and endo alpha and beta compounds corresponding to the product of Example 3 but different therefrom with respect to both the carboxylate-terminated side chain and the side chain attached to the cyclopropane ring of the product. In the same manner, alternative alkylating agents within the scope of Hal—$CH_2$—V—$COOR_{10}$ wherein $R_{10}$ is other than ethyl, e.g., methyl, isopropyl, tert-butyl, octyl, cyclohexyl, benzyl, and phenyl, are used.

EXAMPLE 4 dl-3-Oxa-7-[endo-6-(1-heptenyl)-3-oxobicyclo-[3.1.0]hex-2α-yl]heptanoic acid (Formula LXVI: $R_2$ is pentyl, $R_{10}$ is hydrogen, Z is —$(CH_2)_3OCH_2$—, ~ is endo)

Refer to Chart F. A solution of sodium borohydride (1.5 g.) in 10 ml. of water is added with stirring to a solution of ethyl 3-oxa-7-[endo-6-(1-heptenyl)-3-oxobicyclo-[3.1.0]hex-2α-yl]heptanoate (5.0 g.) in 110 ml. of absolute ethanol at 0° C. The mixture is stirred for 2.5 hours at 0° to 5° C. Then, 40 ml. of acetone is added, and, after 5 min., the mixture is concentrated under reduced pressure. The residue is extracted with dichloromethane, and the extract is washed successively with dilute hydrochloric acid and brine, dried, and concentrated to give dl-ethyl 3-oxa-7-[endo-6-(1-heptenyl)-3-hydroxybicyclo[3.1.0]hex-2α-yl]-heptanoate; NMR peaks at 5.2-5.87 (multiplet), 4.0-4.38 (quartet), 4.01 (singlet), 3.5 (triplet) δ.

This hydroxy ester is dissolved in a mixture of methanol (100 ml.) and 45% aqueous potassium hydroxide solution (30 ml.), and the solution is stirred under nitrogen at 25° C. for 15 hrs. Two volumes of water is then added, and the mixture is acidified with cold hydrochloric acid and then extracted with a mixture of dichloromethane and diethyl ether (1:3). The extract is washed with brine, dried, and concentrated to give dl-3-oxa-7-[endo-6-(1-heptenyl)-3-hydroxybicyclo[3.1.0]hex-2α-yl]heptanoic acid.

Jones reagent (7 ml.; Preparation 4) is added to a solution of this hydroxy acid in 120 ml. of acetone at 0° C. The mixture is stirred 5 min. at 0° C. Then, 5 volumes of water is added, and the mixture is extracted with a mixture of dichloromethane and diethyl ether (1:3). The extract is washed successively with dilute hydrochloric acid and brine, dried, and concentrated to give 4.5 g. of the title compound; NMR peaks at 10.4 (singlet), 4.7–5.9 (multiplet), 4.06 (singlet), 3.54 (triplet) δ.

Following the procedure of Example 4, but using in place of the formula-LXVI 3-oxobicyclo[3.1.0]hexane ester, each of the specific endo and exo, alpha and beta, saturated and acetylenic esters described in and after Example 2 is reduced with sodium borohydride to give the corresponding 3-hydroxybicyclo[3.1.0]hexane ester. That hydroxy ester is then saponified as described in Example 4 to the corresponding 3-hydroxybicyclo[3.1.0]hexane acid. That hydroxy acid is then oxidized as described in Example 4 to the corresponding 3-oxobicyclo[3.1.0]hexane acid.

EXAMPLE 5 dl-3-Oxa-7-[endo-6-(1,2-dihydroxyheptyl)-3-oxobicyclo[3.1.0]hex-2α-yl]heptanoic acid Acetonide (Formula LIX: $R_2$ is pentyl, $R_{10}$ is hydrogen, $R_{11}$ and $R_{12}$ are methyl, V is —(CH$_2$)$_3$OCH$_2$—, ~ is endo)

Refer to Chart E. Following the procedure of Example 4, dl-ethyl 3-oxa-7-[endo-6-(1,2-dihydroxyheptyl)-3-oxobicyclo[3.1.0]hex-2α-yl]heptanoate acetonide is reduced with sodium borohydride to dl-ethyl 3-oxa-7-[endo-6-(1,2-dihydroxyheptyl)-3-hydroxybicyclo[3.1.0]hex-2α-yl]heptanoate acetonide. That hydroxy ester is then saponified as described in Example 4 to dl-3-oxa-7-[endo-6-(1,2-dihydroxy-heptyl)-3-hydroxybicyclo[3.1.0]hex-2α-yl]heptanoic acid acetonide. That hydroxy acid is then oxidized as described in Example 4 to the title compound.

Following the procedure of Example 5 but using in place of the formula-LIX 3-oxobicyclo[3.1.0]hexane ester acetonide, each of the specific endo and exo, alpha and beta, saturated, cis and trans ethylenic, and acetylenic ester cyclic ketals described after Example 3 is reduced with sodium borohydride to give the corresponding 3-hydroxy-bicyclo[3.1.0]hexane ester cyclic ketal. That hydroxy ester is then saponified as in Example 5 to the corresponding 3-hydroxybicyclo[3,1.0-]hexane acid cyclic ketal. That hydroxy acid is then oxidized as in Example 5 to the corresponding 3-oxobicyclo[3.1.0]hexane acid cyclic ketal.

EXAMPLE 6 dl-β,β,β-Trichloroethyl 3-Oxa-7-[endo-6-(1-heptenyl)-3-oxobicyclo[3.1.0-]hex-2α-yl]-heptanoate (Formula LXVI: $R_2$ is pentyl, $R_{10}$ is β,β,β-trichloroethyl, Z is —(CH$_2$)$_3$OCH$_2$—, ~ is endo)

Refer to Chart F. Successively, β,β,β-trichloroethanol (25 ml.), pyridine (15 ml.), and dicyclohexylcarbodiimide (4.0 g.) are added to a solution of dl-3-oxa-7-[endo-6-(1-heptenyl)-3-oxobicyclo[3.1.0]hex-2α-yl]heptanoic acid, (Example 4, 2.0 g.) in 100 ml of dichloromethane. This mixture is stirred 3 hrs. under nitrogen at 25° C. Water (50 ml.) is then added, and the mixture is stirred 10 min. The dichloromethane is evaporated under reduced pressure and the residue is extracted repeatedly with ethyl acetate. The combined extracts are washed with ice-cold 3N hydrochloric acid. Then, the extracts are washed successively with aqueous sodium bicarbonate solution and brine, dried, and concentrated under reduced pressure. The residue is chromatographed on 600 g. of silica gel, eluting with 10 l. of a 20–100% ethyl acetate-Skellysolve B gradient, collecting 250-ml. fractions. The middle fractions which show the presence of a product on TLC with the A-IX system are combined and concentrated under reduced pressure. The residue is chromatographed on 200 g. of silica gel impregnated with silver nitrate, eluting with 4 l. of a 20–100% ethyl acetate-Skellysolve B gradient, collecting 50-ml. fractions. The middle fractions which show a product free of starting materials on TLC with the A-IX system are combined and concentrated under reduced pressure to give the title compound.

Following the procedure of Example 6, but using in place of the formula-LII 3-oxobicyclo[3.1.0]hexane acid, each of the specific endo and exo, alpha and beta, saturated and acetylenic acids defined after Example 4, there are obtained the corresponding β,β,β-trichloroethyl esters of those 3-oxobicyclo[3.1.0]hexane acids.

EXAMPLE 7 dl-β,β,β-Trichloro 3-Oxa-7-[endo-6-(1,2-dihydroxyheptyl)-3-oxobicyclo[3.1.0]hex-2α-yl]heptanoate Acetonite (Formula LIX: $R_2$ is pentyl, $R_{10}$ is β,β,β-trichloroethyl, $R_{11}$ and $R_{12}$ are methyl, V is —(CH$_2$)$_3$OCH$_2$—, ~ is endo).

Refer to Chart E. Following the procedure of Example 6, dl-3-oxa-7-[endo-6-(1,2-dihydroxyheptyl)-3-oxobicyclo-[3.1.0]heptanoic acid acetonide (Example 5) is esterified to the corresponding β,β,β-trichloroethyl ester.

Following the procedure of Example 7, each of the specific formula-LIX exo and endo, alpha and beta, saturated, cis and trans ethylenic, and acetylenic 3-oxobicyclo[3.1.0]hexane acids defined after Example 5 is transformed to the corresponding β,β,β-trichloroethyl ester.

EXAMPLE 8 dl-Ethyl 3-Oxa-7-[endo-6-(1,2-dihydroxyheptyl)-3-oxobicyclo[3.1.0]hex-2α-yl]heptanoate (Formula LXVII: $R_2$ is pentyl, $R_{10}$ is ethyl, Z is —(CH$_2$)$_3$OCH$_2$—, ~ is endo).

Refer to Chart F. Osmium tetroxide (0.15 g.) and a solution of potassium chlorate (2.0 g.) in 24 ml. of water at 50° C. are added to a solution of dl-ethyl 3-oxa-7-[ endo-6-(1-heptenyl)-3-oxobicyclo[3.1.0]hex-2α-yl]heptanoate (Example 1, 2.5 g.) in 50 ml. of tetrahydrofuran at 50° C. The mixture is stirred vigorously at 50° C. for 3 hrs. The resulting mixture is evaporated under reduced pressure and the residue is extracted with dichloromethane. The extract is dried and concentrated to give a residue which is chromatographed on 450 g. of silica gel wet-packed with 950 ml. of 50% ethyl acetate-Skellysolve B (v/v), eluting with 3 l. 50%, 1 l. 60%, 1 l. 70%, 1 l. 80%, and 1 l. 100% ethyl acetate in Skellysolve B, collecting 120-ml. fractions. Fractions 30–36 and 38–47 are separately combined and concentrated to give, respectively, 0.75 g. of a less polar glycol and 1.05 g. of a more polar glycol, both being isomeric forms of dl-ethyl 3-oxa-7-[endo-6-(1,2-dihydroxyheptyl)-3-oxobicyclo[3.1.0]hex-2α-yl]heptanoate; NMR peaks for both glycols at 4.22 (quartet), 4.02 (singlet), and 3.54 (triplet) δ.

EXAMPLE 9 dl-Ethyl 3-Oxa-7-[endo-6-(1,2-dihydroxyheptyl)-3-oxobicyclo[3.1.0]hex-2α-yl]heptanoate. (Formula LXVII: $R_2$ is pentyl, $R_{10}$ is ethyl, Z is —$(CH_2)_3OCH_2$—, ~ is endo)

Osmium tetroxide (0.50 g.) and a solution of potassium chlorate (7.2 g.) in 80 ml. of water at 50° C. are added to a solution of dl-ethyl 3-oxa-7-[endo-6-(1-heptenyl)-3-oxo-bicyclo[3.1.0]hex-2α-yl]heptanoate (Example 1, 9.0 g.) in 175 ml. of tetrahydrofuran at 50° C. The mixture is stirred vigorously at 50° C. for 3.5 hrs. The resulting mixture is concentrated under reduced pressure, and the residue is extracted with dichloromethane. The extract is dried and concentrated to give a residue which is chromatographed on 2 kg. silica gel wet-packed with 4 l. of 50% ethyl acetate-Skellysolve B (v/v) containing 20 ml. of ethanol, eluting with two gradients, the first combining 4 l. 50% ethyl acetate in Skellysolve B with 4 l. of 75% ethyl acetate in Skellysolve B, and the second combining 4 l. 75% ethyl acetate in Skellysolve B with 4 l. ethyl acetate, stripping with ethyl acetate, collecting 400-ml. fractions. Fractions 19 to 35 are combined and concentrated under reduced pressure to give 7.18 g. of mixture of isomeric forms of dl-ethyl 3-oxa-7-[endo-6-(1,2-dihydroxyheptyl)-3-oxobicyclo[3.1.0]hex-2α-yl]heptanoate corresponding to both the less polar and the more polar glycols of Example 8.

EXAMPLE 10 dlEthyl 3-Oxa-7-[endo-6-(1,2-dihydroxyheptyl)-3-oxobicyclo[3.1.0]hex-2α-yl]-heptanoate (Formula LXVII: $R_2$ is pentyl, $R_{10}$ is ethyl, Z is —$(CH_2)_3OCH_2$ —, ~ is endo)

A solution of osmium tetroxide (2.54 g.) in 20 ml. of pyridine at 50° is added to a solution of dl-ethyl 3-oxa-7-[endo-6-(1-heptenyl)-3-oxobicyclo[3.1.0]hex-2α-yl]-heptanoate (Example 1, 3.50 g.) in 25 ml. of pyridine at 5° C. The resulting mixture gradually turns black, and is stirred at 25° C. for 24 hrs. Then 400 ml. of petroleum ether is added, and the precipitate which forms is separated by filtration, washed with petroleum ether, and dissolved in 250 ml. of dioxane. This solution is cooled to 0° C., and is then saturated with hydrogen sulfide gas. The precipitated osmium dioxide is removed by filtration, and the dioxane is removed under reduced pressure to give a glycol mixture substantially the same as that obtained in Example 8.

EXAMPLE 11:

dl-Ethyl 3-Oxa-7-[endo-6-(1,2-dihydroxyheptyl)-3-oxobicyclo[3.1.0]hex-2α-yl]-heptanoate (Formula LXVII: $R_2$ is pentyl, $R_{10}$ is ethyl, Z is —$(CH_2)_3OCH_2$—, ~ endo)

Hydrogen peroxide (0.9 ml. of 30% aqueous solution) is added with stirring to a solution of dl-ethyl 3-oxa-7-[endo6-(1-heptenyl)-3-oxobicyclo[3.1.0]hex-2α-yl]heptanoate (Example 1, 3.5 g.) and sodium carbonate (5.3 g.) in 100 ml. formic acid (98%) at 0° C. under nitrogen. The resulting mixture is allowed to warm to 25° C., and is stirred under nitrogen at 25° C. for one hour. Concentration under reduced pressure gives a residue which is dissolved in 100 ml. of methanol. A solution of sodium carbonate (30 g.) in 100 ml. of water is added to the methanol solution, and the mixture is stirred 4 hrs. at 25° C. The mixture is then acidified and extracted with dichloromethane. The extract is dried and concentrated to give a mixture of isomeric forms of dl-ethyl 3-oxa-7-[endo-6-(1,2-dihydroxyheptyl)-3-oxobicyclo[3.1.0]hex-2α-yl]heptanoate. The individual glycols in this mixture are separated as described in Example 8, or the mixture of glycols is used as a further reactant without separation, as in Example 9.

Following the procedure of Examples 8, 9, 10, or 11 but using the hex-2β-yl isomer in place of the hex-2α-yl isomer of bicyclo reactant, dl-ethyl 3-oxa-7-[endo-6-(1,2-dihydroxyheptyl)-3-oxobicyclo[3.1.0]hex-2β-yl]heptanoate is obtained.

Also following the procedures of Examples 8, 9, 10, or 11, each of the specific formula-LXVI exo and endo, alpha and beta, saturated and acetylenic bicyclo[3.1.0-]hexane olefinic esters defined above after Examples 1 and 2 is oxidized to mixtures of the corresponding isomeric dihydroxy compounds.

Also following the procedures of Examples 8, 9, 10, or 11, each of the specific formula-LXVI exo and endo, alpha and beta, saturated and acetylenic bicyclo[3.1.0-]hexane olefinic β,β,β-trichloroethyl esters defined above in and after Example 6 is oxidized to mixtures of the corresponding isomeric dihydroxy compounds.

EXAMPLE 12:

dl-Ethyl 3-Oxa-7-[endo-6-(1,2-dihydroxyheptyl)-3-oxobicyclo[3.1.0]hex-2α-yl]-heptanoate (Formula LX: $R_2$ is pentyl, $R_{10}$ is ethyl, V is —$(CH_2)_3OCH_2$—, ~ is endo)

Refer to Chart E. Concentrated hydrochloric acid (2.5 ml.) is added to a solution of dl-ethyl 3-oxa-7-[endo-6-(1,2-dihydroxyheptyl)-3-oxobicyclo[3.1.0]hex-2α-yl]-heptanoate acetonide (Example 3, 2.0 g.) in a mixture of 50 ml. of tetrahydrofuran and 2.5 ml. of water. The mixture is stirred at 25° C. under nitrogen for 6 hrs. The resulting mixture is then concentrated under reduced pressure, and the residue is extracted with ethyl acetate. The extract is washed with brine, dried, and concentrated to give essentially the same dl-ethyl 3-oxa-7-[endo-6-(1,2-dihydroxyheptyl)-3-oxobicyclo[3.1.0]hex-2α-yl]heptanoate mixture obtained in Examples 8 and 9.

Following the procedure of Example 12 but using in place of the acetonide, each of the specific formula-LIX exo and endo, alpha and beta, saturated, cis and trans ethylenic, and acetylenic bicyclo[3.1.0]hexane acetonide esters defined above after Example 3, there are obtained the corresponding formula-LX dihydroxy compounds.

Also following the procedure of Example 12 each of the specific formula-LIX exo and endo, alpha and beta, saturated, cis and trans ethylenic, and acetylenic bicyclo-[3.1.0]hexane acetonide β,β,β-trichloroethyl esters defined in and after Example 7 is hydrolyzed to the corresponding dihydroxy β,β,β-trichloroethyl ester.

EXAMPLE 13:

*dl*-Ethyl
3-oxa-7-[endo-6-)1,2-dihydroxyheptyl)-3-oxobicyclo3-oxobicyclo[3.1.0]hex-2α-yl]-cis-5-heptenoate Acetonide (Formula LIX: $R_2$ is pentyl, $R_{10}$ is ethyl, $R_{11}$ and $R_{12}$ are methyl, V is cis—CH=CHCH$_2$OCH$_2$—, ~ is endo)

Refer to Chart E. A solution of dl-ethyl 3-oxa-7-[endo-6-(1,2-dihydroxyheptyl)-3-oxobicyclo[3.1.0]hex-2α-yl]-5-heptynoate acetonide (0.5 g.) in 10 ml. of pyridine is hydrogenated in the presence of a 5% palladium on barium sulfate catalyst (150 mg.) at 25° C. and one atmosphere. During 300 min., 90 ml. of hydrogen is absorbed. The resulting mixture is filtered and concentrated to about one-third the original volume. Four volumes of ethyl acetate is added, and the remaining pyridine is removed by addition of ice and one N hydrochloric acid. The ethyl acetate layer is separated, washed successively with one N hydrochloric acid and brine, dried, and concentrated. The residue is chromatographed on 250 g. of silica gel which has previously been acid-washed to pH 4 (Silicar CC4, 100–200 mesh, Mallincrodt Co.), eluting with 3 l. of a 25–5% ethyl acetate-Skellysolve B gradient, collecting 100-ml. fractions. The fractions shown to have the desired product free of starting material by TLC with the A-IX system are combined and concentrated under reduced pressure to give the title compound.

Following the procedure of Example 13, each of the specific formula-LIX exo and endo, alpha and beta, acetylenic bicyclo[3.1.0]hexane ester cyclic ketals defined above after Example 3, and also each of the corresponding specific acetylenic $\beta,\beta,\beta$-trichloroethyl ester cyclic ketals defined above in Example 7 and thereafter is hydrogenated to the corresponding cis-ethylenic cyclic ketal. Following the procedure of Example 12, each of those specific formula-LIX exo and endo, alpha and beta, cis-ethylenic bicyclo[3.1.0]-hexane cyclic ketals is then hydrolyzed with hydrochloric acid to the corresponding formula-LX cis-ethylenic dihydroxy ester, including the $\beta,\beta,\beta$-trichloroethyl ester.

Also following the procedure of Example 13, but using in place of the acetonide, each of the specific formula-LX and each of the specific formula-LXVII exo and endo, alpha and beta, acetylenic bicyclo[3.1.0-]hexane dihydroxy esters, including $\beta,\beta,\beta$-trichloroethyl esters, defined above after Examples 11 and 12 is hydrogenated to the corresponding cis-ethylenic dihydroxy ester, including the $\beta,\beta,\beta$-trichloroethyl ester.

EXAMPLE 14:

*dl*-Ethyl
3-oxa-6-[endo-6-(1,2-dihydroxyheptyl)-3-oxobicyclo[3.1.0]hex-2α-yl]-trans-5-heptenoate Acetonide (Formula LIX: $R_2$ is pentyl, $R_{10}$ is ethyl, $R_{11}$ and $R_{12}$ are methyl, V is trans—CH=CHCH$_2$OCH$_2$—, ~ is endo)

Refer to Chart E. A solution of dl-ethyl 3-oxa-7[endo-6-(1,2-dihydroxyheptyl)-3-oxobicyclo[3.1.0]hex-2α-yl]-5-heptynoate acetonide (1.0 g.) in 20 ml. of tetrahydrofuran is cooled to −10° C. This solution is added to a fresh solution of lithium metal (0.1 g.) in 30 ml. of liquid ammonia in a glass-lined autoclave. The autoclave is sealed, and the reaction mixture is stirred for 16 hrs. at 25° C. ambient temperature. Then the autoclave is opened, and the ammonia allowed to evaporate. Water (20 ml.) is added, and the resulting solution is acidified with one N hydrochloric acid, and then extracted with ethyl acetate. The extract is washed successively with aqueous sodium bicarbonate solution and brine, dried, and concentrated under reduced pressure. The residue is chromatographed as described for the corresponding cis compound in Example 12 to give the title compound.

Following the procedure of Example 14, each of the specific formula-LIX exo and endo, alpha and beta acetylenic bicyclo[3.1.0]hexane ester cyclic ketals defined above after Example 3, and also each of the corresponding specific acetylenic $\beta,\beta,\beta$-trichloroethyl ester cyclic ketals defined above in Example 7 and thereafter is reduced to the corresponding trans-ethylenic cyclic ketal. Following the procedure of Example 12, each of those specific formula-LIX exo and endo, alpha and beta, trans-ethylenic bicyclo[3.1.0]-hexane cyclic ketals is then hydrolyzed to the corresponding formula-LX trans-ethylenic dihydroxy ester, including the $\beta,\beta,\beta$-trichloroethyl ester.

Also following the procedure of Example 14, but using in place of the acetonide, each of the specific formula-LX and each of the specific formula-LXVII exo and endo, alpha and beta, acetylenic bicyclo[3.1.0-]hexane dihydroxy esters, including $\beta,\beta,\beta$-trichloroethyl ester, defined above after Examples 11 and 12 is reduced to the corresponding transethylenic dihydroxy ester, including the $\beta,\beta,\beta$-trichloroethyl ester.

EXAMPLE 15:

*dl*-Ethyl
3-Oxa-7-[endo-6-(1,2-dimesyloxy-heptyl)-3-oxobicyclo[3.1.0]hex-2α-yl]-heptanoate (Formula LXVIII: $R_2$ is pentyl, $R_{10}$ is ethyl, $R_{11}$ and $R_{12}$ are methyl, Z is —(CH$_2$)$_3$OCH$_2$—, ~ is endo)

Refer to Chart F. Methanesulfonyl cohloride (2.0 ml.) is added dropwise with stirring to a solution of the less polar form of dl-ethyl 3-oxa-7-[endo-6-(1,2-dihydroxyheptyl)-3-oxobicyclo[3.1.0]hex-2α-yl]heptanoate (745 mg.; Example 8) in 20 ml. of pyridine at 0° C. under nitrogen. The mixture is stirred at 0° C. for 2.5 hrs. under nitrogen. Then, ice chips (30 g.) are added, and the resulting mixture is stirred 10 min. This mixture is mixed with 250 ml. of a mixture of dichloromethane and diethyl ether (1:2, v/v). That mixture is washed successively with cold one N hydrochloric acid, water, aqueous sodium bicarbonate solution, and brine. The organic layer is separated, dried, and concentrated under reduced pressure to give 830 mg. of the title compound; nMR singlet peaks at 3.05 and 3.08 δ.

The above procedure is repeated with the more polar form of ethyl 3-oxa-7-[endo-6-(1,2-dihydroxyheptyl)-3-oxobicyclo-[3.1.0]hex-2α-yl]heptanoate (1045 mg.; Example 8) to give an isomeric dimesylate of the same formula and with the same NMR peaks.

EXAMPLE 16:

*dl*-Ethyl
3-Oxa-7-[endo-6-(1,2-dimesyloxyheptyl)-3-oxobicyclo[3.1.0]hex-2α-yl]-heptanoate (Formula LXVIII: $R_2$ is pentyl, $R_{10}$ is ethyl, $R_{11}$ and $R_{12}$ are methyl, Z is —(CH$_2$)$_3$OCH$_2$—, ~ is endo)

Refer to Chart F. Methanesulfonyl chloride (20 ml.) is added dropwise with stirring during 2 minutes to a solution of the mixture (7.18 g.) of ethyl 3-oxa-7-[endo-6-(1,2-dihydroxyheptyl)-3-oxobicyclo[3.1.0]hex- 2α-yl]-heptanoate isomers obtained in Example 9 in 150 ml. of pyridine at −15° C. The mixture is stirred 2.5 hrs. at 0° C. under nitrogen. A mixture of isomeric forms of dl-ethyl 3-oxa-7-[endo-6-(1,2-dimesyloxyheptyl)-3-oxobicyclo[3.1.0]-hex-2α-yl]heptanoate is then obtained from the resulting mixture as described in Example 15.

Following the procedures of Examples 15 and 16, the racemic forms of ethyl 3-oxo-7-[endo-6-(1,2-dihydroxyheptyl)-3-oxobicyclo[3.1.0]hex-2β-yl]heptanoate, β,β,β-trichloroethyl 3-oxa-7-[endo-6-(1,2-dihydroxyheptyl)-3-oxobicyclo[3.1.0]-hex-2α-yl]heptanoate, β,β,β-trichloroethyl 3oxa-7-[endo-6-(1,2-dihydroxyheptyl)-3-oxobicyclo(3.1.0]hex-2β-yl]-heptanoate, ethyl 3-oxa-7-[endo-6-(1,2-dihydroxyheptyl)-3-oxobicyclo[3.1.0]hex-2α-yl]-cis-5-heptenoate, ethyl 3-oxa-7-[endo-6-(1,2-dihydroxyheptyl-3 1oxobicyclo[3.1.0]hex-2β-yl]-cis-5-heptenoate, β,β,β-trichloroethyl 3-oxa-7-[endo-6-(1,2-dihydroxyheptyl)-3-oxobicyclo[3.1.0]hex-2α-yl]-cis-5-heptenoate, β,β,β-trichloroethyl 3-oxa-7-[endo-6-(1,2-dihydroxyheptyl)-3-oxobicyclo[3.1.0]hex-2β-yl]-cis-5-heptenoate, ethyl 3-oxa-7-[endo-6-(1,2-dihydroxyheptyl)-3-oxobicyclo[3.1.0]hex-2α -yl]-trans-5-heptenoate, ethyl 3-oxa-7-[endo-6-(1,2-dihydroxyheptyl)-3-oxobicyclo[3,1.0]-hex-2β-yl]-trans-5-heptenoate, β, β,β-trichloroethyl 3-oxa-7-[endo-6-(1,2-dihydroxyheptyl)-3-oxobicyclo[3.1.0]hex-2α-yl]-trans-5-heptenoate, β,β,β-trichloroethyl 3-oxa-7-[endo-6-(1,2-dihydroxyheptyl)-3-oxobicyclo[3.1.0]hex-2β-yl]-trans-5-heptenoate, ethyl 3-oxa-7-[endo-6-(1,2-dihydroxyheptyl)-3-oxobicyclo[3.1.0]hex-2α-yl]-5-heptynoate, ethyl 3-oxa-7-[endo-6-(1,2-dihydroxyheptyl)-3-oxobicyclo[3.1.0]hex-2βyl]-5-heptynoate, β,β,β-trichloroethyl 3-oxa-7-[endo-6-(1,2-dihydroxyheptyl)-3-oxobicyclo[3.1.0]hex-2α-yl]-5-heptynoate, and β,β,β-trichloroethyl 3-oxa-7-[endo-6-(1,2-dihydroxyheptyl)-3-oxobicyclo[3.1.0-]hex-2β-yl]-5-heptynoate are each transformed to the corresponding 1,2-dimesyloxyheptyl compound.

Also following the procedure of Examples 15 and 16, each of the endo-4-oxa-1,2-dihydroxyheptyl esters corresponding to the endo-3-oxa-1,2-dihydroxyheptyl ester of Examples 15 and 16 and to each of the 15 other above-listed endo-3-oxa-1,2-dihydroxyheptyl esters is transformed to the corresponding endo-4-oxa-1,2-dimesyloxyheptyl ester.

Also following the procedures of Examples 15 and 16, each of the 16 exo-3-oxa-1,2-dihydroxyheptyl ester and each of the 16 exo-4-oxa-1,2-dihydroxy esters corresponding to the above-defined 16 endo-3-oxa, 1,2-dihydroxyheptyl esters and the above-defined 16 endo-4-oxa-1,2-dihydroxyheptyl esters, respectively, is transformed to the corresponding exo-3-oxa-1,2-dimesyloxyheptyl ester and the corresponding exo-4-oxa-1,2-dimesyloxyheptyl ester.

Also following the procedures Examples 15 and 16, each of the other specific exo and endo, alpha and beta, saturated, cis and trans ethylenic, and acetylenic, 3-oxa and 4-oxa glycols defined above after Examples 11, 12, 13, and 4 is transformed to the corresponding dimesyloxy compound.

EXAMPLE 17:

dl-3-Oxa-PGE₁ Ethyl Ester (Formula LXII: Q is

$R_2$ is pentyl, $R_{10}$ is ethyl, V is $-(CH_2)_3OCH_2-$)

Refer to Chart E. A solution of dl-ethyl 3-oxa-7-[endo-6-(1,2-dimesyloxyheptyl)-3-oxobicyclo[3.1.0]hex-2α-yl]hex-2α-yl]heptanoate (830 mg., Example 15; obtained from the less polar glycol of Example 8) in a mixture of acetone (25 ml.) and water (12.5 ml.) is maintained at 25° C. for 16 hrs. Additional water (25 ml.) is then added, and the acetone is removed under reduced pressure. The remaining water solution is extracted with a mixture of deithyl ether and dichloromethane (2:1), and the extract is washed successively with 10% aqueous sodium bicarbonate solution and brine, dried, and concentrated to give 0.40 g. of residue.

The above procedure is repeated with the dimesylate obtained in Example 15 from more polar glycol (1.045 g.) of Example 8. TLC behavior shows that the residue (0.80 g.) from this procedure is similar in composition to the residue from the above procedure.

The two residues are combined (1.20 g.) and chromatographed on a column prepared by wet-packing 500 g. of silica gel with one l. of 50% ethyl acetate in Skellysolve B, eluting with a gradient of 3 l. of 50% ethyl acetate in Skellysolve B with 3 l. of ethyl acetate, and then with 1.5 l. of 10% ethanol in ethyl acetate, collecting 110-ml. fractions. Fractions 7–17 are combined and concentrated to give 520 mg. of a mixture of isomeric forms of 3-oxa-7-[endo-6-(1-hydroxy-2-mesyloxyheptyl)-3-oxobicyclo[3.1.0]-hex-2α-yl]heptanoate. Fractions 46–54 are combined to give 225 mg. dl-15-epi-3-oxa-PGE₁ ethyl ester; NMR peaks at 5.64–5.74 (multiplet), 4.0–4.39 (quartet), 4.01 (singlet), 3.5 (triplet) δ. Fraction 60 (ethanol-ethyl acetate) is evaporated to give 235 mg. of dl-3-oxa-PGE₁ ethyl ester; NMR peaks at 5.5–5.7 (multiplet), 4.0–4.39 (quartet), 4.01 (singlet), 3.5 (triplet) δ.

Following the procedure of Example 17, the mixture of dimesylates of Example 16 is transformed to 0.99 g. of dl-15-epi-3-oxa-PGE₁ ethyl ester and 0.99 of dl-3-oxa-PFE₁ ethyl ester.

Following the procedure of Example 17, each of the specific dimesylates defined in the first paragraph after Example 16 is transformed to the racemic forms of 8-iso-3-oxa-PGE₁ ethyl ester, 8-iso-15-epi-3-oxa-PGE₁ ethyl ester, 3-oxa-PGE₁ β,β,β-trichloroethyl ester, 15-epi-3-oxa-PGE₁, β,β,β-trichloroethyl ester, 8-iso-3-oxa-PGE₁, β,β,β-trichloroethyl ester, 8-iso-15-epi-3-oxa-PGE₁ β,β,β,-trichloroethyl ester, 3-oxa-PGE₂ ethyl ester, 15-epi-3-oxa-PGE₂ ethyl ester, 8-iso-3-oxa-PGE₂ ethyl ester, 8-iso-15-epi-3-oxa-PGE₂ ethyl ester, 3-oxa-PGE₂ β,β,β-trichloroethyl ester, 15-epi-3-oxa-PGE₂ β,β,β-trichloroethyl ester, 8-iso-3-oxa-PGE₂ β,β,β-trichloroethyl ester, 8-iso-15-epi-3-oxa-PGE₂ β,β,β-trichloroethyl ester, trans-5,6-dehydro-3-oxa-PGE₁ ethyl ester, trans-5,6-dehydro-15-epi-3 -oxa-PGE₁ ethyl ester, trans-5,6-dehydro-8-iso-3-oxa-PGE₁ ethyl ester, trans-5,6-dehydro-8-iso-15-epi-3-oxa-PGE₁ ethyl ester, trans-5,6-dehydro-3-oxa-pGE₁ β,β,β-trichloroethyl ester, trans-5,6-dehydro-15-epi-3-oxa-PGE₁ β,β,β-trichloroethyl ester, trans-5,6-dehydro-8-iso-3-oxa-PGE₁ β,β,β-trichloroethyl ester, trans-5,6-dehydro-8-iso-15-epi-3-oxa-PGE₁ β,β,β-trichloroethyl ester, 5,6-dehydro-3-oxa-PGE₂ ethyl ester, 5,6-dehydro-15-epi-3-oxa-PGE₂ ethyl ester, 5,6-dehydro-8-iso-3-oxa-PGE₂ ethyl ester, 5,6-dehydro-8-iso-15-epi-3-oxa-PGE₂ ethyl ester, 5,6-dehydro-3-oxa-PGE₂ β,β,β-trichloroethyl ester, 5,6-dehydro-15-epi-3-oxa-PGE₂ β,β,β-trichloroethyl ester, 5,6-dehydro-8-iso-3-oxa-PGE₂, β,β,β-trichloroethyl ester, and 5,6-dehydro-8-iso-15-epi-3-oxa-PGE₂ β,β,β-trichloroethyl ester, respectively.

Also following the procedure of Example 17, each of the 16 endo-4-oxa-1,2-dimesyloxyheptyl esters corresponding to the endo-3-oxa-1,2-dimesyloxyheptyl esters used as reactant in Example 17 or in the paragraph above is transformed to the corresponding 4-oxa-prostaglandin E ester.

Also following the procedure of Example 17, each of the specific 16 exo-3-oxa-1,2-dimesyloxyheptyl esters defined above and each of the specific 16 exo-4-oxa-1,2-dimesyloxy esters defined above is transformed to the same corresponding 3-oxa-prostaglandin E ester and 4-oxa-prostaglandin E ester and 4-oxa-prostaglandin E ester, respectively.

Also following the procedure of Example 17, each of the other specific exo and endo, alpha and beta, saturated, cis and trans ethylenic, and acetylenic 3-oxa and 4-oxa dialkanesulfonic acid esters defined above after Example 16, including the β,β,β-trichloroethyl esters, is transformed to the corresponding 3-oxa- and 4-oxa-prostaglandin-like E ester.

In each of the transformations described above after Example 17, the monomesylate corresponding to the monomesylate product of Example 17 is also obtained.

EXAMPLE 18:

dl-Ethyl 3-Oxa-7-[endo-6-(1,2-dimesyloxyheptyl)-3-oxobicyclo[(3.1.0]hex-2α-yl]heptanoate Following the procedure of Example 15, the 520 mg. of dl-ethyl 3-oxa-7-[endo-6-(1-hydroxy-2-mesyloxyheptyl)-3-oxobicyclo[3.1.0]hex-2α-yl]heptanoate obtained as a byproduct in Example 17 is reacted with methanesulfonyl chloride to give the corresponding 1,2-dimesyloxyheptyl compound, used as reactant in Example 17.

Following the procedure of Example 18, each of the monomesylates obtained as a byproduct during production of each of the 3-oxa and 4-oxa prostaglandin-like esters defined after Example 17 is transformed to the corresponding dimesylate.

EXAMPLE 19:

dl-3-Oxa-PGE₁ (Formula XVIII: Q is

$C_nH_{2n}$ is —(CH₂)₃—, R₂ is pentyl, R₁, R₅, and R₆ are hydrogen)

Zinc dust (400 mg.) is added to a solution containing dl-3-oxa-PGE₁ β,β,β-trichloroethyl ester (100 mg.) in 5 ml. of a mixture of acetic acid and water (9:1 v/v). This mixture is stirred under nitrogen 2 hrs. at 25° C. Ethyl acetate (4 volumes) is then added, followed by additin of one N. hydrochloric acid (one vol.). The ethyl acetate layer is separated, washed with water and then with brine, dried, and concentrated. The residue is chromatographed on 15 g. of acid-washed silica gel (Silicar CC4), being eluted with 100 ml. of 50%, 100 ml. of 80%, and 200 ml. of 100% ethyl acetate in Skellysolve B, collecting 20-ml. fractions. The fractions containing dl-3-oxa-PGE₁ and no starting material or dehydration products as shown by TLC are combined and evaporated to give dl-3-oxa-PGE₁.

Following the procedure of Example 19, dl-15-epi-3-oxa-pGE₁ β,β,β-trichloroethyl ester is transformed to dl-15-epi-3-oxa-PGE₁.

Also following the procedure of Example 19, each of the specific β,β,β-trichloroethyl esters defined in the second paragraph after Example 17 is transformed to the racemic forms of 8-iso-3-oxa-PGE₁, 8-iso-15-epi-3-oxa-PGE₁, 3-oxa-PGE₂, 15-epi-3-oxa-PGE₂, -iso-3-oxa-PGE₂, 8-iso-15-epi-3-oxa-PGE₂, trans-5,6-dehydro-3-oxa-PGE₁, trans-5,6-dehydro-15-epi-3-oxa-PGE₁, trans-5,6-dehydro-8-iso-3-oxa-PGE₁, trans-5,6-dehydro-8-iso-15-epi-3-oxa-PGE₁, 5,6-dehydro-3-oxa-PGE₂, 5,6-dehydro-15-epi-3-oxa-PGE₂, 5,6-dehydro-8-iso-3-oxa-PGE₂, and 5,6-dehydro-8-iso-15-epi-3-oxa-PGE₂, respectively.

Also following the procedure of Example 19, the β,β,β-trichloroethyl esters of each of 4-oxa-prostaglandin E compounds corresponding to the β,β,β-trichloroethyl esters of each of the above 3-oxa-prostaglandin E compounds is transformed to the corresponding dl-4-oxa-prostaglandin E free acid.

Also following the procedure of Example 19, each of the other β,β,β-trichloroethyl esters of 3-oxa- and 4-oxaporstaglandin-like E compounds defined above after Example 17 is transformed to the corresponding dl-3-oxa- and 4-oxaprostaglandin-like E free acid.

EXAMPLE 20

Enzymatic Hydrolysis of dl-3-Oxa-PGE₁ Ethyl Ester

A. Enzyme preparation

A medium is prepared consisting 2% corn steep liquor (a mixture of equal parts of cerelose and glucose) in tap water. This is brought to pH 4.5 by adding hydrochloric acid, and 1% of methyl oleate is added. Four 500 ml. flasks each containing 100 ml. of the above medium are inoculated with Cladosporum resinae (Cl-11, ATCC 11,274) and are placed on a shaker at room temperature (about 28° C.) for 4 days. The culture is then placed in 40 ml. centrifuge tubes and centrifuged at about 2000 rmp. in a clinical centrifuge. The liquid is decanted from the centrifuge tubes and the collected cells are washed with cold water. The washed cells from 2 centrifuge tubes are suspended in 50 ml. of ice cold 0.05 M ph 7.0 phosphate buffer and placed in small Waring blender cup chilled with ice. Glass beads are added and the suspended cells are churned in the blender for 15 minutes. The resulting suspension of broken cells is centrifuged in a clinical centrifuge at about 2000 r.p.m. for 15 min. at room temperature, then the supernatant liquid is collected. This supernatant liquid contains Cladosporium resinae acylase and is used directly for the hydrolysis of alkyl esters or is stored, preferably frozen, until needed.

B. Esterase hydrolysis

Ten milliliters of the supernatant liquid containing Cladosporium resinae acylase, prepared as described in part A of this example and 50 mg. of dl-3-oxa-PGE₁ ethyl ester (Example 17) are shaken at room temperature under nitrogen for about 19 hrs., then 70 ml. of acetone is added and the mixture is filtered giving a filtrate and an insoluble residue. The filtrate is concentrated under reduced pressure and gives 40–50 mg. of a slightly yellow oil comprising 3-oxa-PGE₁. Both this oil and the insoluble residue are combined and chromatographed over 10 g. of acid-washed silica gel (Silicar CC-4, Mallinckrodt). Elution is with mixed hexanes (Skellysolve B) containing increasing amounts of ethyl acetate, collecting 50 ml. fractions as follows:

| Fraction | Solvent | | | |
|---|---|---|---|---|
| 1 | Skellysolve B | | | |
| 2 | 40 ml. | Skellysolve B - | 10 ml. | ethyl acetate |
| 3 | 30 | " | 20 | " |
| 4 | 25 | " | 25 | " |
| 5 | 20 | " | 30 | " |
| 6 | 10 | " | 40 | " |
| 7 | 5 | " | 45 | " |
| 8 | ethyl acetate | | | |
| 9 | ethyl acetate | | | |
| 10 | ethyl acetate | | | |
| 11 | ethyl acetate | | | |
| 12 | 100 ml. of ethyl acetate | | | |

Fractions 6 to 12 are combined and concentrated to give 3-oxa-PGE$_1$ with substantially the same properties as that obtained according to Example 19.

Following the procedure of Example 20, each of the specific methyl, ethyl, and other alkyl ester defined above after Example 17 is hydrolyzed enzymatically to the corresponding $dl$-3-oxa- or 4-oxa prostaglandin-like E free acid.

EXAMPLE 21

$dl$-3-Oxa-PGF$_{1\alpha}$ Ethyl Ester and $dl$-3-Oxa-PGF$_1$ Ethyl Ester (Formula XXVIII: Q is

$C_nH_{2n}$ is —(CH$_2$)$_3$—, R$_1$ is ethyl, R$_2$ is pentyl, R$_5$ and R$_6$ are hydrogen, ~ is alpha or beta)

Refer to Chart A. A solution of sodium borohydride (0.30 g.) in 1 ml. of water is added with stirring to a solution of $dl$-3-oxa-PGE$_1$ ethyl ester (Example 17, 600 mg.) in 25 ml. of absolute ethanol at 0° C. The mixture is stirred 2.5 hrs. at 0° C. Then, 15 ml. of acetone is added and, 10 min. later, 3 volumes of water is added. The mixture is acidified with dilute hydrochloric acid and then extracted with dichloromethane. The extract is washed with brine, dried, and concentrated. The residue is chromatographed on 400 g. of silica gel wet-packed with 800 ml. of chloroform containing 60 ml. of absolute ethanol, eluting with 2 l. of 12.5% and 2 l. of 15% absolute ethanol in chloroform, collecting 100-ml. fractions. Fractions 1–5 are combined and concentrated to give 122 mg. of $dl$-3-oxa-PGF$_{1\alpha}$ ethyl ester, m.p. 44°–5° C. after recrystallization from a mixture of diethyl ether and Skellysolve B. Fractions 9–7 are combined and evaporated to give 238 mg. of $dl$-3-oxa-PGF$_{1\beta}$ ethyl ester; m.p. 77°–78° C. after recrystallization from diethyl ether.

Following the procedure of Example 21, $dl$-3-oxa-PGE$_1$ is transformed to $dl$-3-oxa-PGF$_{1\alpha}$ and $dl$-3-oxa-PGF$_{1\beta}$.

Also following the procedure of Example 21, the ethyl ester and free acid forms of the racemic forms of 15-epi-3-oxa-PGF$_{1\alpha}$, 15-epi-3-oxa-PGF$_{1\beta}$, 8-iso-3-oxa-PGF$_{1\alpha}$, 8-iso-3-oxa-PGF$_{1\beta}$, 8-iso-15-epi-3-oxa-PGF$_{1\alpha}$, 8-iso-15-epi-3-oxa-PGF$_{1\beta}$, 3-oxa-PGF$_{2\alpha}$, 3-oxa-PGF$_{2\beta}$, 15-epi-3-oxa-pGF$_{2\alpha}$, 15-epi-3-oxa-PGF$_{2\beta}$, 8-iso-3-oxa-PGF$_{2\alpha}$, 8-iso-3-oxa-PGF$_{2\beta}$, 8-iso-15-epi-3-oxa-PGF$_{2\alpha}$, 8-iso-15-epi-3-oxa-PGF$_{2\beta}$, trans-5,6-dehydro-3-oxa-PGF$_{1\alpha}$, trans-5,6-dehydro-3-oxa-PGF$_{1\beta}$, trans-5,6-dehydro-15-epi-3-oxa-PGF$_{1\alpha}$, trans-5,6-dehydro-15-epi-3-oxa-PGF$_{1\beta}$, trans-5,6-dehydro-8-iso-3-oxa-PGF$_{1\alpha}$, trans-5,6-dehydro-8-iso-3-oxa-PGF$_{1\beta}$, trans-5,6-dehydro-8-iso-15-epi-3-oxa-PGF$_{1\alpha}$, trans-5,6-dehydro-8-iso-15-epi-3-oxa-PGF$_{1\beta}$, 5,6-dehydro-3-oxa-PGF$_{2\alpha}$, 5,6-dehydro-3-oxa-PGF$_{2\beta}$, 5,6-dehydro-15-epi-3-oxa-PGF$_{2\alpha}$, 5,6-dehydro-15-epi-3-oxa-PGF$_{2\beta}$, 5,6-dehydro-8-iso-3-oxa-PGF$_{2\alpha}$, 5,6-dehydro-8-iso-3-oxa-PGF$_{2\beta}$, 5,6-dehydro-8-iso-15-epi-3-oxa-PGF$_{2\alpha}$, 5,6-dehydro-8-iso-15-epi-3-oxa-PGF$_{2\beta}$, 4-oxa-PGF$_{1\alpha}$, 4-oxa-PGF$_{1\beta}$, 15-epi-4-oxa-PGF$_{1\alpha}$, 15-epi-4-oxa-PGF$_{1\beta}$, 8-iso-4-oxa-PGF$_{1\alpha}$, 8-iso-4-oxa-PGF$_{1\beta}$, 8-iso-15-epi-4-oxa-PGF$_{1\alpha}$, 8-iso-15-epi-4-oxa-PGF$_{1\beta}$, 4-oxa-PGF$_{2\alpha}$, 4-oxa-PGF$_{2\beta}$, 15-epi-4-oxa-PGF$_{2\alpha}$, 15-epi-4-oxa-pGF$_{2\beta}$, 8-iso-4-oxa-PGF$_{2\alpha}$, 8-iso-4-oxa-PGF$_{2\beta}$, 8-iso-15-epi-4-oxa-PGF$_{2\alpha}$, 8-iso-15-epi-4-oxa-PGF$_{2\beta}$, trans-5,6-dehydro-4-oxa-PGF$_{1\alpha}$, trans-5,6-dehydro-4-oxa-PGF$_{1\beta}$, trans-5,6-dehydro-15-epi-4-oxa-PGF$_{1\alpha}$, trans-5,6-dehydro-15-epi-4-oxa-PGF$_{1\beta}$, trans, 5,6-dehydro-8-iso-4-oxa-PGF$_{1\alpha}$, trans-5,6-dehydro-8-iso-4-oxa-PGF$_{1\beta}$, trans-5,6-dehydro-8-iso-15-epi-4-oxa-PGF$_{1\alpha}$, trans-5,6-dehydro-8-iso-15-epi-4-oxa-PGF$_{1\beta}$, 5,6-dehydro-4-oxa-PGF$_{2\alpha}$, 5,6-dehydro-4-oxa-PGF$_{2\beta}$, 5,6-dehydro-15-epi-4-oxa-PGF$_{2\alpha}$, 5,6-dehydro-15-epi-4-oxa-PGF$_{2\beta}$, 5,6-dehydro-8-iso-4-oxa-PGF$_{2\alpha}$, 5,6-dehydro-8-iso-4-oxa-PGF$_{2\beta}$, 5,6-dehydro-8-iso-15-epi-4-oxa-PGF$_{2\alpha}$, and 5,6-dehydro-8-iso-15-epi-4-oxa-PGF$_{2\beta}$ are prepared by reduction of the corresponding $dl$-3-oxa-or 4-oxa-PGE type ethyl ester or free acid.

Also following the procedure of Example 21, each of the other 3-oxa- and 4-oxa-PGE-type-esters and free acids defined above after Examples 17 and 19 is transformed to the corresponding 3-oxa- and 4-oxa-PGF$_\alpha$-type and PGF$_\beta$-type ester and free acid.

EXAMPLE 22

$dl$-3-Oxa-PGA$_1$ Ethyl Ester and Free Acid (Formula XXXVIII: Q is

$C_nH_{2n}$ is —(CH$_1$)$_3$—, R$_1$ is ethyl or hydrogen, R$_2$ is pentyl, R$_5$ and R$_6$ are hydrogen)

Refer to Chart A. A solution of 3-oxa-PGE$_1$ ethyl ester (Example 17, 400 mg.) in a mixture of tetrahydrofuran (5 ml.) and 0.5 N hydrochloric acid (5 ml.) is maintained under nitrogen at 25° C. for 5 days. The resulting mixture is diluted with one volume of brine and extracted with a mixture of diethyl ether and dichloromethane (3:1). The extract is washed with brine, dried, and concentrated. The residue (380 mg.) is dissolved in diethyl ether, and the solution is extracted with cold 5% aqueous sodium bicarbonate solution to give an aqueous layer A and a diethyl ether layer B. Aqueous layer A is acidified with dilute hydrochloric acid and then extracted with dichloromethane. This extract is washed with brine, dried, and concentrated to give 300 mg. of $dl$-3-oxa-PGA$_1$ free acid; NMR peaks at 7.38–7.63 (multiplet), 6.1–6.3 (multiplet), 7.0 (singlet), 5.57–5.7 (multiplet), 4.05 (singlet), and 3.53 (triplet) δ. Diethyl ether layer B is evaporated to give 62 mg. of $dl$-3-oxa-PGA$_1$ ethyl ester; NMR peaks at 7.35–7.6 (multiplet), 6.1–6.25 (multiplet), 5.6–5.75

(multiplet), 4.23 (quartet), 4.02 (singlet), and 3.52 (triplet) δ.

EXAMPLE 23

*dl*-3-Oxa-PGA₁ Ethyl Ester

Refer to Chart A. A solution of 3-oxa-PGE₁ ethyl ester in a mixture of glacial acetic acid (9 ml.) and water (1 ml.) is heated under nitrogen at 60° C. for 18 hrs. Then, the acetic acid and water are evaporated under reduced pressure, and the residue is chromatographed on 50 g. of acid-washed silica gel, eluting with a 25–100% gradient of ethyl acetate in Skellysolve B. The fractions containing the desired product free of starting material as shown by TLC are combined and concentrated to give *dl*-3-oxa-PGA₁ ethyl ester with substantially the same physical properties as when prepared by the procedure of Example 22.

Following the procedure of Example 22 or of Example 23, *dl*-3-oxa-PGE₁ free acid is transformed to *dl*-3-oxa-PGA₁ free acid.

Also following the procedure of Example 22 or Example 23, the ethyl ester and free acid forms of the racemic forms of 15-epi--oxa-PGA₁, 8-iso-s-oxa-PGA₁, 8-iso-15-epi-3-oxa-PGA₁, 3-oxa-PGA₂, 14-epi-3-oxa-PGA₂, 8-iso-3-oxa-PGA₂, 8-iso-15-epi-3-oxa-PGA₂, trans-5,6-dehydro-3-oxa-PGA₁, trans-5,6-dehydro-15-epi-3-oxa-PGA₁, trans-5,6-dehydro-8-iso-3-oxa-PGA₁, trans-5,6-dehydro-8-iso-15-epi-3-oxa-PGA₁, 5,6-dehydro-3-oxa-PGA₂, 5,6-dehydro-15-epi-3-oxa-PGA₂, 5,6-dehydro-8-iso-3-oxa-PGA₂, 5,6-dehydro-8-iso-15-epi-3-oxa-PGA₂, 4-oxa-PGA₁, 15-epi-4-oxa-PGA₁, 8-iso-4-oxa-PGA₁, 8-iso-15-epi-4-oxa-PGA₁, 4-oxa-PGA₂, 15-epi-4-oxa-PGA₂, 8-iso-4-oxa-PGA₂, 8-iso-15-epi-4-oxa-PGA₂, trans-5,6-dehydro-4-oxa-PGA₁, trans-5,6-dehydro-15-epi-4-oxa-PGA₁, trans-5,6-dehydro-8-iso-4-oxa-PGA₁, trans-5,6-dehydro-8-iso-15-epi-4-oxa-PGA₁, 5,6-dehydro-4-oxa-PGA₂, 5,6-dehydro-15-epi-4-oxa-PGA₂, 5,6-dehydro-8-iso-4-oxa-PGA₂, and 5,6-dehydro-8-iso-15-epi-4-oxa-PGA₂ are prepared by dehydration of the corresponding *dl*-3-oxa- or 4-oxa-PGE-type ethyl ester or free acid.

Also following the procedure of Example 22 or of Example 23, each of the other 3-oxa- and 4-oxa-PGE type esters and free acids defined above after Examples 17 and 19, including the β,β,β-trichloroethyl esters, is transformed to the corresponding 3-oxa- and 4-oxa-PGA type ester and free acid.

EXAMPLE 24: dl-3-oxa-PGA₁ Ethyl Ester.

Refer to Chart E. A solution of dl-ethyl 3-oxa-7[endo-6-(1,2-dimesyloxyheptyl)-3-oxobicyclo[3.1.0]hex-2α-yl]-heptanoate (from 800 ml. of less polar glycol; Example 15) in 75 ml. of acetone is mixed with 10 ml. of water and 20 ml. of saturated aqueous sodium bicarbonate solution. The mixture is refluxed under nitrogen for 4 hrs. Then, the mixture is cooled, acidified with 5% hydrochloric acid, and extracted with ethyl acetate. The extract is washed with brine, dried, and evaporated to give *dl*-3-oxa-PGA₁ ethyl ester with substantially the same physical properties as when prepared by the procedures of Examples 22 and 23.

Following the procedure of Example 24, each of the dimesylates defined after Example 17 is transformed to the corresponding 3-oxa- or 4-oxa-PGA-type ester, including the β,β,β-trichloroethyl esters, each of those esters corresponding to the 3-oxa- or 4-oxa-PGE type esters prepared as described in and after Example 17.

EXAMPLE 25:

*dl*-3-Oxa-PGA₁ Free Acid

Following the procedure of Example 19, dl-3-oxa-PGA₁, β,β,β-trichloroethyl ester is transformed to dl-3-oxa-PGA₁ free acid, with substantially the same physical properties as when prepared according to Example 22.

EXAMPLE 26:

*dl*-3-Oxa-PGB₁ (Formula XLVIII: Q is

$C_nH_{2n}$ is —$(CH_2)_3$—, $R_1$, $R_5$, and $R_6$ are hydrogen, $R_2$ is pentyl)

Refer to Chart A. A solution of *dl*-3-oxa-PGE₁ (200 mg.) in 100 ml. of 50% aqueous ethanol containing 10 grams of potassium hydroxide is kept at 25° C. for 10 hrs. under nitrogen. Then, the solution is cooled at 10° C. and neutralized by addition of 3 normal hydrochloric acid at 10° C. The resulting solution is extracted repeatedly with ethyl acetate, and the combined ethyl acetate extracts are washed with water and then with brine, dried, and concentrated to give the title compound.

Following the procedure of Example 26, *dl*-3-oxa-PGA₁ is transformed to dl-3-oxa-PGB₁ with substantially the same physical properties as when prepared from *dl*-3-oxa-PGE₁.

Also following the procedure of Example 26, the racemic forms of 15-epi-3-oxa-PGB₁, 3-oxa-PGB₂, 15-epi-3-oxa-PGB₂, trans-5,6-dehydro-3-oxa-PGB₁, trans-5,6-dehydro-15epi-3-oxa-PGB₁, 5,6-dehydro-3-oxa-PGB₂, 5,6-dehydro-15-epi-3-oxa-PGB₂, 4-oxa-PGB₁, 15-epi-4-oxa-PGB₁, 4-oxa-PGB₂, 15-epi-4-oxa-PGB₂, trans-5,6-dehydro-4-oxa-PGB₁, trans-5,6-dehydro-15-epi-4-oxa-PGB₁, 5,6-dehydro-4-oxa-PGB₂, and 5,6-dehydro-15-epi-4-oxa-PGB₂ are prepared from the corresponding 3-oxa- and 4-oxa-PGE type acids and also from the corresponding 3-oxa- and 4-oxa-PGA type compounds defined above after Examples 19, 20, 22, and 25.

EXAMPLE 27:

*dl*-13,14-Dihydro-3-oxa-PGE₁ (Formula XXIV: Q is

$C_nH_{2n}$ is —$(CH_2)_3$—, $R_5$ and $R_6$ are hydrogen, $R_2$ is pentyl)

Refer to Chart B. A solution of *dl*-3-oxa-PGE₁ (Example 19, 100 mg.) in 10 ml. of ethyl acetate is shaken with hydrogen at about one atmosphere pressure at 25° C. in the presence of 5% palladium on charcoal (15 mg.). One equivalent of hydrogen is absorbed in about 90 min. The hydrogenation is then stopped, and the catalyst is removed by filtration. The filtrate is concentrated, and the residue is chromatographed on 25 g. of silica gel, eluting with a 50–100% ethyl acetate gradient in Skellysolve B. Those fractions shown by TLC to contain the desired product free of the starting product and dehydration products are combined and concentrated to give the title compound.

Following the procedure of Example 27, dl-3-oxa-PGE$_1$ ethyl ester is reduced to dl-13,14-dihydro-3-oxa-PGE$_1$ ethyl ester.

Also following the procedure of Example 27, dl-3-oxa-PGE$_2$, trans-5,6-dehydro-3-oxa-PGE$_1$, and dl-5,6-dehydro-3-oxa-PGE$_2$ are each reduced to dl-13,14-dihydro-3-oxo-PGE$_1$ using two equivalents of hydrogen for the first two reactants, and three equivalents of hydrogen for the third reactant.

Also following the procedure of Example 27, the ethyl ester and the free acid form of the racemic forms of 13,14-dihydro-15-epi-3-oxa-PGE$_1$, 13,14-dihydro-8-iso-3-oxa-PGE$_1$, 13,14-dihydro-8iso-15-epi-3-oxa-PGE$_1$, 13,14-dihydro-4-oxa-PGE$_1$, 13,14-dihydro-15-epi-4-oxa-PGE$_1$, 13,14-dihydro-8-iso-4-oxa-PGE$_1$, and 13,14-dihydro-8-iso-15-epi-4-oxa-PGE$_1$ are prepared by catalytic hydrogenation of the ethyl ester and free acid form of the corresponding 3-oxa and 4-oxo-PGE-type compound, using equivalents of hydrogen appropriate to the degree of unsaturation of the reactant, i.e., one equivalent for the PGE$_1$ type, two equivalents for the PGE$_2$ type and trans-5,6-dehydro-PGE$_1$ type, and three equivalents for the 5,6-dehydro-PGF$_2$ type.

Also following the procedure of Example 27, dl-3-oxa-PGF$_{1\alpha}$ and its ethyl ester are reduced to dl-13,14-dihydro-3-oxa-PGF$_{1\alpha}$ and the ethyl ester of that, respectively.

Also following the procedure of Example 27, the ethyl ester and the free acid form of the racemic forms of 13,14-dihydro-3-oxa-PGF$_{1\beta}$, 13,14-dihydro-15-epi-3-oxa-PGF$_{1\alpha}$, 13,14-dihydro-15-epi-3-oxa-PGF$_{1\beta}$, 13,14-dihydro-8-iso-3-oxa-PGF$_{1\alpha}$, 13,14-dihydro-8-iso-3-oxa-PGF$_{1\beta}$, 13,14-dihydro-8-iso-15-epi-3-oxa-pGF$_{1\alpha}$, 13,14-dihydro-8-iso-15-epi-3-oxa-PGF$_{1\beta}$, 13,14-dihydro-4-oxa-PGF$_{1\alpha}$, 13,14-dihydro-4-oxa-PGF$_{1\beta}$, 13,14-dihydro-15-epi-4-oxa-PGF$_{1\alpha}$, 13,14-dihydro-15-epi-4-oxa-PGF$_{1\beta}$, 13,14-dihydro-8-iso-4-oxa-PGF$_{1\alpha}$, 13,14-dihydro-8-iso-4-oxa-PGF$_{1\beta}$, 13,14-dihydro-8-iso-15-epi-4-oxa-PGF$_{1\alpha}$, and 13,14-dihydro-8-iso-15-epi-4-oxa-PGF$_{1\beta}$ are prepared by catalytic hydrogenation of the ethyl ester and free acid form of the corresponding 3-oxa and 4oxa-PGF type compound, using equivalents of hydrogen appropriate to the degree of unsaturation of the reactant.

Also following the procedure of Example 27, each of the esters and free acid forms of the other 3-oxa- and 4-oxa-PGE type and PGF type compounds defined above after Examples 17, 19, and 21 is catalytically hydrogenated to the corresponding dihydro compound.

EXAMPLE 28:

dl-13,14-Dihydro-3-oxa-PGA$_1$ (Formula XLIV: Q is

C$_n$H$_{2n}$ is —(CH$_2$)$_3$—, R$_1$, R$_5$, and R$_6$ are hydrogen, R$_2$ is pentyl)

Refer to Chart B. A suspension of disodium azodiformate (50 mg.) is 5 ml. of absolute ethanol is added to a stirred solution of dl-3-oxa-PGA$_1$ (50 mg.) in 10 ml. of absolute ethanol under nitrogen at 25° C. The mixture is made acid with glacial acetic acid, and then is stirred under nitrogen at 25° C. for 8 hrs. The resulting mixture is concentrated under reduced pressure, and the residue is mixed with a mixture of diethyl ether and water (1:1). The diethyl ether layer is separated, dried, and concentrated to give the title compound.

Following the procedure of Example 28, dl-3-oxa-PGA$_1$ ethyl ester is reduced to dl-13,14-dihydro-3-oxa-PGA$_1$ ethyl ester.

Also following the procedure of Example 28, the racemic forms of 3-oxa-PGA$_2$, trans-5,6-dehydro-3-oxa-PGA$_1$, and 5,6-dehydro-3-oxa-PGA$_2$ are each reduced to 13,14-dihydro-3-oxa-PGA$_1$, using amounts of the disodium azodiformate reactant appropriate to the degree of unsaturation of the reactant.

Also following the procedure of Example 28, the ethyl ester and the free acid form of the racemic forms of 13,14-dihydro-15-epi-3-oxa-PGA$_1$, 13,14-dihydro-8-iso-3-oxa-PGA$_1$, 13,14-dihydro-8-iso-15-epi-PGA$_1$, 13,14-dihydro-4-oxa-PGA$_1$, 13,14-dihydro-15-epi-4-oxa-PGA$_1$, 13,14-dihydro-8-iso-4-oxa-PGA$_1$, and 13,14-dihydro-8-iso-15-epi-4-oxa-PGA$_1$ are prepared by diimide reduction of the corresponding 3-oxa- and 4-oxa-PGA type compound, using amounts of diimide appropriate to the degree of unsaturation of the PGA type reactant.

Also following the procedure of Example 28, the ethyl ester and the free acid form of the racemic forms of 13,14-dihydro-3-oxa-PGB$_1$, 13,14-dihydro-15-epi-3-oxa-PGB$_1$, 13,14-dihydro-4-oxa-PGB$_1$, and 13,14-dihydro-15-epi-4-oxa-PGB$_1$ are prepared by diimide reduction of the corresponding 3-oxa-and 4-oxa-PGB type compound, using amounts of diimide appropriate to the degree of unsaturation of the PGB type reactant.

Also following the procedure of Example 28, each of the esters and free acid forms of the other 3-oxa- and 4-oxa-PGA type and PGB type compounds defined above in and after Examples 22, 23, 24, 25, and 26 is reduced with diimide to the corresponding dihydro compound.

EXAMPLE 29:

dl3-Oxa-PGB$_1$ Methyl Ester

A solution of diazomethane (about 0.5 g.) in diehtyl ether (25 ml.) is added to a solution of dl-3-oxa-PGB$_1$ (Example 26, 50 mg.) 25 ml. of a mixture of methanol and diethyl ether (1:1). The mixture is allowed to stand at 25° C. for 5 min. Then, the mixture is concentrated to give the title compound.

Following the procedure of Example 29, each of the other specific 3-oxa and 4-oxa PGB type, PGA type, PGE type, and PGF type free acids defined above is converted to the corresponding methyl ester.

Also following the procedure of Example 29, but using in place of the diazomethane, diazoethane, diazobutane, 1-diazo-2-ethylhexane, and diazocyclohexane, there are obtained the corresponding ethyl, butyl, 2-ethylhexyl, and cyclohexyl esters of 3-oxa-PGB$_1$. In the same manner, each of the other specific 3-oxa and 4-oxa PGB type, PGA type, PGE type, and PGF type free acids defined above is converted to the corresponding ethyl, butyl, 2-ethylhexyl, and cyclohexyl esters.

EXAMPLE 30:

dl-3-Oxa-PGE$_1$ Methyl Ester Diacetate

Acetic anhydride (5 ml.) and pyridine (5 ml.) are mixed with dl-3-oxa-PGE$_1$ methyl ester (20 mg.), and the mixture is allowed to stand at 25° C. for 18 hrs. The mixture is then cooled to 0° C., diluted with 50 ml. of water, and acidified with 5% hydrochloric acid to pH 1.

That mixture is extracted with ethyl acetate. The extract is washed successively with 5% aqueous sodium bicarbonate solution, water, and brine, dried, and concentrated to give the title compound.

Following the procedure of Example 30 but replacing the acetic anhydride with propionic anhydride, isobutyric anhydride, and hexanoic acid anhydride, there are obtained the corresponding dipropionate, diisobutyrate and dihexanoate derivatives of dl-3-oxa-PGE$_1$ methyl ester.

Also following the procedure of Example 30, each of the 3-oxa and 4-oxa PGE type, PGF type, PGA type, and PGB type esters and free acids defined above is transformed to the corresponding acetate, propionates, isobutyrates, and hexanoates, the PGE derivatives being dicarboxyacylates, the PGF type derivatives being tricarboxyacylates, and the PGA type and PGB type derivatives being monocarboxyacylates.

EXAMPLE 31:

dl-3-Oxa-PGE$_1$ Sodium Salt

A solution of dl-3-oxa-PGE$_1$ (Example 19, 100 mg.) in 50 ml. of a water-ethanol mixture (1:1) is cooled to 5° C. and neutralized with an equivalent amount of 0.1 N aqueous sodium hydroxide solution. The neutral solution is concentrated to give the title compound.

Following the procedure of Example 31 but using potassium hydroxide, calcium hydroxide, tetramethylammonium hydroxide, and benzyltrimethylammonium hydroxide in place of sodium hydroxide, there are obtained the corresponding salts of dl-3-oxa-PGE$_1$.

Also following the procedure of Example 31 each of the 3-oxa and 4-oxa PGE type, PGF type, PGA type, and PGB type acids defined above is transformed to the sodium, potassium, calcium, tetramethylammonium, and benzyltrimethylammonium salts.

EXAMPLE 32:

dl-3-Oxa-PGE$_3$ Methyl Ester (Formula XXVI: Q is

(C$_j$ H$_{2j}$ and C$_p$H$_{2p}$ are —CH$_2$—, R$_1$ is methyl, R$_4$ is ethyl, and R$_5$ and R$_6$ are hydrogen) and its 15$\beta$ epimer 1. Refer to chart H. Following the procedure of Preparations 5, 6, and 7, but replacing hexyltriphenyl-phosphonium bromide with (hex-3-ynyl) triphenylphosphonium bromide (Axen et al., CHem. Comm. 1970, 602) there are obtained successively endo-6-(cis- and trans-1-hepten-4-ynyl)-bicyclo[3.1.0]hexan-3-ol tetrahydropyranyl ether; endo-6-(cis- and trans-1-hepten-4ynyl) bicyclo[3.1.0]hexan-3-ol; and the formula-LXXIII endo-6-(cis and trans-1-hepten-4-ynyl) bicyclo [3.1.0]hexan-3-one. The desired formula-LXXIII intermediate is isolated after silica gel chromatography.

2. There is next prepared the compound corresponding to formula-LXXXIV by alkylation. Following the procedures of Example 2, the product of step 1 above is reacted with methyl 7chloro-3-oxa-hept-5ynoate to yield dl-methyl 7-[endo-6-(cis- and trans-1-hepten-4-ynyl)-3-oxobicyclo-[3.1.0]hex-2α-yl]-3-oxa-hept-5-ynoate.

3. Glycol LXXXV is next prepared, following the procedure of Example 8 and reacting the product of step 2 with osmium tetroxide. Without separating the isomeric glycols, the bismesylate corresponding to formula LXXXVI is then prepared following the procedures of Example 15. Thereafter, following hydrolysis of the bismesylate by the procedures of Example 17, the bisdehydro-PGE$_3$-type compound corresponding to formula LXXXVII is recovered. Silica gel chromatography is used to separate the respective C-15 epimers.

4. Thereafter, each of the C-15 epimers of step 3 above is hydrogenated in pyridine using 5% palladium on barium sulfate catalyst at 25° C. and one atmosphere and the products subjected to silica gel chromatography to yield the title compounds.

The various Preparations and Examples given above describe the preparation of racemic intermediates and final products. Each of intermediates and final products named and defined above is also obtained in each of the enantiomeric forms, d and l, by resolution of that compound or by resolution of an intermediate used to prepare that compound. For example, d-3-oxa-PGA$_1$ free acid is prepared by resolution of dl-3oxa-PGA$_1$ free acid (Example 22) or by dehydration as in Example 22 of optically active 3-oxa-PGE$_1$ free acid with the same absolute configuration. These resolutions are carried out by procedures known in the art, for example, those described hereinabove.

EXAMPLE 33:

2,3,4-Trinor-PGF$_{2\alpha}$, Ethyl Ester, Bis(tetrahydropyranyl ether) (Formula CXII: —CH=CH— is in cis configuration, Q" is

R$_2$ is n-pentyl, R$_{21}$ is THP, i.e., tetrahydro-pyranyl, and R$_{22}$ is ethyl); and its 5,6-trans isomer Refer to Chart M. The starting material is the formula-CXI compound, 3α, 5α-dihydroxy-2β-(3α-hydroxy-trans-1-octenyl)-1αcyclopentaneacetaldehyde γ-lactol bis (tetrahydropyranyl ether). See E. J. Corey et al., J. Am. Chem. Soc. 92, 397 (1970). The optically active isomer is used which will lead to a prostaglandin-type compound of the natural configuration. The formula-CXI compound (10.0 g.) is dissolved in 150 ml. of obsolute ethanol containing 3 drops of acetic acid. To the solution is added (carbethoxymethylene)triphenyl phosphorane (10 g.) and the mixture is stirred at about 25° C. for 72 hrs. The mixture is concentrated under reduced pressure to a volume of about 35 ml., mixed with ice and dilute sodium bicarbonate solution, and shaken with ethyl acetate. The organic phase is washed with brine, dried over magnesium sulfate, and concentrated to a residue. The residue is slurried in 100 ml. of diethyl ether and filtered. The filtrate is concentrated to a residue which is subjected to silica gel chromatography, eluting with 20–40% ethyl acetate in Skellysolve B (mixed isomeric hexanes). Besides unreacted starting material there are recovered the title compound, 1.1g., its 5,6-trans isomer, 1.63 g., and a mixture of the two isomers, 3.89 g. The NMR spectrum of the title compound has peaks at 6.52–5.74, 5.70–5.39, 4.72, 4.37–4.00 (quartet), 1.38–1.15 (triplet), and 0.87 δ. The NMR spectrum of the 5,6-trans isomer has peaks at 7.30–5.75, 5.66–5.38, 4.70, 4.37–4.00 (quartet), 1.38–1.15 (triplet), and 0.87 δ:

EXAMPLE 34:

2,3,4-Trinor-PGF$_{1\alpha}$, Ethyl Ester, Bis(tetrahydropyranyl ether) (Formula CXIII : Q'' is

R$_2$ is n-pentyl, R$_{21}$ is THP, and R$_{22}$ is ethyl)

Refer to Chart M. The formula-CXII PGF$_{2\alpha}$ compound (Example 33, 1.10 g.) is mixed with a 5%-palladium-on-carbon catalyst (0.3 g.) in 30 ml. of ethyl acetate and hydrogenated at slightly above atmospheric pressure. When about 41 ml. of hydrogen is consumed, the catalyst is filtered off and the filtrate concentrated under reduced pressue to yield the title compound, 1.10 g. The NMR spectrum has peaks at 5.70–5.39, 4.72, 4.37–4.00 (quartet), 1.38–1.15 (triplet), and 0.87 δ.

EXAMPLE 35:

4α-(4-Hydroxybutyl)-5β-(3'α-hydroxy-1'-trans-octenyl)cyclopentane-1α, 3α-diol, 1,3'-Bis(tetrahydropyranyl ether) (Formula CXIV: Q'' is

R$_2$ is n-pentyl, R$_{21}$ is THP, and R$_{23}$ is hydrogen)

Refer to Chart M. The formula-CXIII PGF$_{1\alpha}$ compound (Example 34, 1.1 g.) in 30 ml. of diethyl ether added with added with stirring to a mixture of lithium aluminum hydride (0.3 g.) in 60 ml. of diethyl ether over a 10 minute period. The mixture is heated under reflux for 2 hrs., cooled, and treated with 0.35 ml. of water added cautiously dropwise followed by 0.35 ml. of 15% aqueous sodium hydroxide solution and then 1.0 ml. of water. The solids are removed by filtration and filtrate is concentrated under reduced pressure to give the title compound.

EXAMPLE 36:

3-Oxa-PGF$_{1\alpha}$, 11,15-Bis(tetrahydropyranyl ether), Ethyl Ester (Formula CXV: Q'' is

R$_1$ is ethyl, R$_2$ is n-pentyl, R$_1$ is THP, and R$_{23}$ is hydrogen)

Refer to Chart M. The formula-CXIV 4-hydroxybutyl compound (Example 35, 1.7 g.) together with 15 ml. of dimethylsulfoxide and 5 ml. of tetrahydrofuran, is treated with 2.28 ml. of 1.6 M n-butyllithium in hexane, with stirring and cooling. After 5 min., there is added 5 ml. of dimethyformamide. The solution is stirred and cooled to 0° C. and lithium chloroacetate (0.70 g.) is added. The mixture is stirred at 0° C. for 2 hrs. and at about 25° C. for 22 hrs., then diluted with 200 ml. of ice water, acidified with a cold solution of 3 ml. of concentrated hydrochloric acid in 50 ml. of water, and immediately extracted with dichloromethane. The organic phase is washed with cold water and brine, and dried over magnesium sulfate. At this stage the solution contains 3-oxa-PGF$_{1\alpha}$, 11,15-bis(tetrahydropyranyl ether).

To the above solution is added excess ethereal diazoethane and after a few minutes the excess reagent is destroyed with acetic acid. The mixture is washed with a mixture of sodium bicarbonate solution and brine, and then brine, dried and concentrated under reduced pressure. The residue is subjected to silica gel chromatography, eluting with 60–100% ethyl acetate in Skellysolve B to yield the title compound, 0.71 g. The NMR spectrum has peaks at 5.2–5.58, 4.6, 3.99–4.29, 3.95 (singlet), and 3.35–3.55 δ.

EXAMPLE 37:

3-Oxa-PGF$_{1\alpha}$, Ethyl Ester (Formula CXVI: Q' is

R$_1$ is ethyl arid R$_2$ is n-pentyl)

Refer to Chart M. The formula-CXV bis(tetrahydropyranyl ether) (Example 36, 0.7 g.) is mixed with 15 ml. of acetic acid and 7.5 ml. of water and heated at about 38° C. for 2.5 hrs. The mixture is diluted with ice and water and shaken with ether-dichloromethane (3:1). The organic phase is washed with cold dilute sodium bicarbonate, water, and brine, and dried and concentrated. The residue is subjected to silica gel chromatography, eluting with 12.5–15% ethanol in chloroform, to yield the title compound.

EXAMPLE 38:

3-Oxa-PGE$_1$, Ethyl Ester (Formula CXVIII: Q' is

R$_1$ is ethyl, and R$_2$ is n-pentyl)

Refer to Chart M. The formula-CXV 3-oxa-PGF$_{1\alpha}$, 11,15tetrahydropyranyl ether), ethyl ester (Example 36, 0.7 g.) in 25 ml. of acetone at −20° C. is treated with 0.67 ml. of Jones reagent (J. Chem. Soc. 39 (1946) ). The mixture is stirred at −20° C. for 15 min., diluted with ice and water, and immediately extracted with ether-dichloromethane (3:1). The organic phase is washed with ice cold dilute hydrochloric acid and brine, dried and concentrated to give the formula-CXVII 3-oxa-PGE$_1$, 11,15-bis(tetrahydropyranyl ether), ethyl ester, 0.66 g. The NMR spectrum has peaks at 5.35–5.7, 4.64, 3.98–4.3, 3.95 (singlet) and 3.36–3.53 δ: infrared spectral absorption at 1740 cm$^{-1}$.

The formula-CXVII intermediate above is hydrolyzed to remove tetrahydropyranyl groups following the procedure of Example 37. Thereafter, using silica gel chromatography, and eluting with 1–5% ethanol in ethyl acetate, there is obtained the title compound, 0.28 g., having the same NMR spectrum as the product of Example 17 above.

EXAMPLE 39:

3α-Allyl-2-[(3'S)-3'-hydroxy-1'-trans-octenyl]cyclopentane-1α, 4α-diol, 1,3'-Bis-(tetrahydropyranyl ether) (Formula CXXIV: Q'' is

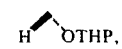

R$_2$ is n-pentyl, and R$_{21}$ is THP)

Refer to Chart O. Methyltriphenylphosphonium bromide (17.5 g.) is added to a solution of sodio dimethylsulfinylcarbanide prepared from sodium hydride (57%, 2.02 g.) and 75 ml. of dimethyl sulfoxide at 65°–70° C. and cooled to 15° C. The mixture is stirred at 15°–25° C. for 20 min., cooled to 15° C., and to it is added a solution of the formula-CXI 3α,5α-dihydroxy-2β-(3α-hydroxy-trans-1-octenyl)-1α-cyclopentaneacetaldehyde γ-lactol bis(tetrahydropyranyl ether) (10 g.) in 20 ml. of dimethyl sulfoxide. See E. J. Corey et al., J. Am. Chem. Soc. 92, 397 (1970). That optically active isomer is used which will lead to a prostaglandin-type compound of the natural configuration. The resulting mixture above is stirred at about 25° C. for 2.5 hrs., then shaken with water and 500 ml. of diethyl ether. The organic phase is washed with water and brine, dried, and concentrated under reduced pressure. The residue is triturated with diethyl ether and, then, Skellysolve B, to yield triphenylphosphine oxide (3.5 g.) and a residue which is chromatographed on a silica gel column to yield the title compound, 5.6 g., having $R_f$ 0.8 (TLC on silica gel plates in ethyl acetate-Skellysolve B (1:1)) and NMR spectal peaks at 4.9–6.2 and 4.7 δ.

EXAMPLE 40:

2α, 4α-Dihydroxy-5[(3'S)-3'-hydroxy-1'-transoctenyl]cyclopentane-1α-propanol,2,3', 4-Tris-(tetrahydropyranyl ether) (Formula CXXVI: Q'' is

$R_2$ is n-pentyl, and $R_{21}$ is THP)

Refer to Chart O. There is first prepared the formula-CXXV tris(tetrahydropyranyl) ether. A mixture of the formula-CXXIV 3-allyl-2-[(3'S)-3'-hydroxy-1'-trans-octenyl]-cyclopentane-1α, 4α-diol, 1,3-bis(tetrahydropyranyl ether) (Example 39, g.), 15 ml. of freshly distilled dihydropyran, and 0.3 g. of pyridine hydrochloride in 100 ml. of dichloromethane is stirred under nitrogen at about 25° C. for 18 hrs. The mixture is diluted with 500 ml. of cold diethyl ether, washed with ice-cold 0.1 N hydrochloric acid, water, 5% aqueous sodium bicarbonate, and brine, dried, and concentrated under reduced pressure. The product is subjected to silica gel chromatography, eluting with 5–25% ethyl acetate in Skellysolve B, to yield the tris(tetrahydropyranyl ether).

To a solution of the above compound (5.2 g.) in 50 ml. of dry tetrahydrofuran at 0° C. under nitrogen is added with stirring 10 ml. of disiamylborane (bis(1,2-dimethylpropyl)borane) (1M. in tetrahydrofuran). After one hr. at 0° C. there is added one ml. of water and (cautiously) a solution of one ml. of 50% aqueous sodium hydroxide in 20 ml. of methanol. To this mixture is added 15 ml. of 15% hydrogen peroxide, maintaining the temperature below 40° C. After stirring one hr. at about 25° C., the mixture is shaken with brine and ethyl acetate. The organic phase is washed with brine, dried, and concentrated. The residue is taken up in xylene and again concentrated under reduced pressure. The product is subjected to silica gel chromatography eluting with 30–50% ethyl acetate in Skellysolve B to yield the title compound.

EXAMPLE 41:

3α-Allyloxypropyl-2-[(3'S)-3'-hydroxy-1'-trans-octenyl]cyclopentane-1α, 4α-diol, 1,3', 4-Tris(tetrahydropyranyl ether) (Formula CXXVII: Q'' is

$R_2$ is n-pentyl, and $R_{21}$ is THP)

Refer to Chart O. N-Butyllithium (6.25 ml. of 1.6 M. solution in hexane) is added dropwise to a stirred solution of the formula-CXXVI 2α,4α-dihydroxy-5-[(3'S)-3'-hydroxy-1'-trans-octenyl]cyclopentane-1α-propanol,2,3',4-tris(tetrahydropyranyl ether) (Example 40, 5.4 g.) in 40 ml. of tetrahydrofuran. There is then added 10 ml. of freshly distilled allyl chloride and 40 ml. of dimethylformamide. After stirring about 0.5 hr., the mixture is shaken with water and diethyl ether. The organic phase is washed with water and brine, dried, and concentrated. The product is subjected to silica gel chromatography, eluting with 5–20% ethyl acetate in Skellysolve B.

EXAMPLE 42:

2-Decarboxy-2-hydroxymethyl-4-oxa-PGF$_1\alpha$, 9,11,15-Tris(tetrahydropyranyl ether) Formula CXXVIII: Q'' is

$R_2$ is n-pentyl, and $R_{21}$ is THP)

Refer to Chart O. Following the procedure of Example 40, the formula-CXXVII 3α-allyloxypropyl-2[(3'S)-3'-hydroxy-1'-trans-octenyl]cyclopentane-1α,4α-diol, 1,3',4-tris(tetrahydropyranyl ether) (Example 41, 5.8 g.) is reacted with disiamylborane and hydrogen peroxide to yield the title compound.

EXAMPLE 43

4-Oxa-PGF$_1\alpha$, Tris(tetrahydropyranyl ether). (Formula CXXIX: Q'' is

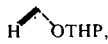

$R_2$ is n-pentyl, $R_{21}$ is THP, and $R_1$ is hydrogen

Refer to Chart O. The formula-CXXVIII 2-decarboxy-2-hydroxymethyl-4-oxa-PGF$_1\alpha$, 9,11,15-tris(-tetrahydropyranyl ether) (Example 42, 3.0 g.) in 50 ml. of acetone is treated at −20° C. with 3 ml. of Jones reagent over a period of about one min. Thereafter the mixture is stirred for 30 min, and shaken with ethyl acetate (300 ml.) and brine (200 ml.). The organic phase is washed with water and brine, dried, and concentrated. The product is subjected to silica gel chromatography to yield the title compound.

EXAMPLE 44:

4-Oxa-PGF$_1\alpha$ (Formula CXXX: Q' is

$R_2$ is n-pentyl, and $R_1$ is hydrogen)

Refer to Chart O. The formula-CXXIX 4-oxa-PGF$_{1\alpha}$, tris(tetrahydropyranyl ether) (Example 43, 1.0 g.) is stirred with 25 ml. of glacial acetic acid, 12.5 ml. of water, and 3 ml. of tetrahydrofuran at 40° C. for 4 hrs. Thereafter the mixture is freeze-dried and the residue is subjected to silica gel chromatography, eluting with 60% ethyl acetate in Skellysolve B to 100% ethyl acetate to yield the title compound.

EXAMPLE 45:

4-Oxa-PGF$_{1\alpha}$, Methyl Ester, Tris(tetrahydropyranyl ether) Formula CXXIX: Q″ is

R$_2$ is n-pentyl, R$_{21}$ is THP, and R$_1$ is methyl)

Refer to Chart O. There is first prepared the formula-CXXIX 4-oxa-PGF$_{1\alpha}$, tris(tetrahydropyranyl ether) following the procedure of Example 43. The acid (3.0 g.) is then treated with excess ethereal diazomethane for a few minutes. The excess diazomethane is destroyed by addition of acetic acid and the mixture is washed with dilute sodium bicarbonate and brine, dried, and concentrated. The product is subjected to silica gel chromatography to yield the title compound.

EXAMPLE 46:

4-Oxa-PGF$_{1\alpha}$, Methyl Ester (Formula CXXX: Q' is

R$_2$ is n-pentyl, and R$_1$ is methyl)

Refer to Chart O. The formula-CXXIX 4-oxa-PGF$_{1\alpha}$, methyl ester, tris(tetrahydropyranyl ether) (Example 45, 1.0 g.) is stirred with 25 ml. of glacial acetic acid, 12.5 ml. of water, and 3 ml. of tetrahydrofuran at 40° C. for 4 hrs. The mixture is then diluted with 150 ml. of ethyl acetate and shaken with cold dilute sodium hydroxide solution. The organic phase is washed with brine, dried, and concentrated. The product is subjected to silica gel chromatography, eluting with 8–16% ethanol in chloroform to yield the title compound.

EXAMPLE 47:

2α,4α-Dihydroxy-5-[(3′S)-3′-hydroxy-1′-trans-octenyl]cyclopentane-1α-ethanol, 3′, 4-Bis-(tetrahydropyranyl ether) (Formula CXXXI: Q″ is

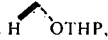

R$_2$ is n-pentyl, and R$_{21}$ is THP)

Refer to Chart P. The formula-CX 3α,5α-dihydroxy-2β-(3α-hydroxy-trans-1-octenyl)-1α-cyclopentaneacetaldehyde γ-lactol bis(tetrahydropyranyl ether) (6.3 g.) in 50 ml. of ethanol at 0° C. is treated, while stirring, with a solution of sodium borohydride (0.6 g.) in 10 ml. water. After 10 min. the mixture is shaken with 20 ml. of water, 250 ml. of ethyl acetate, and 150 ml. of brine. The organic phase is washed with brine, dried, and concentrated under reduced pressure to yield the title compound, 6.3 g., having R$_f$ 0.2 (TLC on silica gel in 50% ethyl acetate in Skellysolve B).

EXAMPLE 48:

3 -Allyloxyethyl-2-[(3′S)-3′-hydroxy-1′-trans-octenyl]cyclopentane-1α,4α-diol, 1,3′-Bis-(tetrahydropyranyl ether) (Formula CXXXII: Q″ is

R$_2$ is n-pentyl, and R$_{21}$ is THP)

Refer to Chart P. The formula-CXXXI 2α,4α-dihydroxy-5-[(3′S)-3′-hydroxy-1′-trans-octenyl]cyclopentane-1α-ethanol, 3′,4-bis(tetrahydropyranyl ether) (Example 47, 8.1 g.) in 40 ml. of tetrahydrofuran at −15° C. under nitrogen is treated, while stirring, with 11.5 ml. of 1.6 M. n-butyllithium in hexane added dropwise over a 5-min. period. To the clear solution is added 15 ml. of freshly distilled allyl chloride and 40 ml. of dimethyl formamide. The mixture is stirred at about 25° C. for 24 hrs. and is then shaken with 400 ml. of water and 500 ml. of ether. The organic phase is washed with water and brine, dried, and concentrated under reduced pressure. The residue is subjected to silica gel chromatography, eluting with 50% ethyl acetate in Skellysolve B, to obtain the title compound, 2.0 g., having NMR spectral peaks at 5.0–6.2, 4.7, and 3.87–4.0 δ.

EXAMPLE 49:

2-Decarboxy-2-hydroxymethyl-5-nor-4-oxa-PGF$_{1\alpha}$, 9,11,15-Tris(tetrahydropyranyl ether) (Formula CXXXIII: Q″ is

R$_2$ is n-pentyl, and R$_{21}$ is THP)

Refer to Chart P. The formula-CXXXII 3α-allyloxyethyl-2-[(3′S)-3′-hydroxy-1′-trans-octenyl]cyclopentane-1α,4α-diol, 1,3′-bis(tetrahydropyranyl ether) (Example 48, 2.0 g.) in 20 ml. of tetrahydrofuran at 0° C. under nitrogen is treated, while stirring, with 10 ml. of 1M. disiamylborane in tetrahydrofuran added dropwise. The mixture is stirred at 0° C. for an additional hour, then treated with 2 ml. of water added cautiously. Then a solution of 1 ml. of 50% aqueous sodium hydroxide in 25 ml. of methanol is added followed by 15 ml. of 15% hydrogen peroxide solution added dropwise while stirring, maintaining the temperature below 40° C. The mixture is stirred an additional hour at about 25° C., then shaken with 100 ml. of brine and ethyl acetate. The organic phase is washed with brine, dried, and concentrated under reduced pressure. Xylene is added and the mixture concentrated under vacuum at about 40° C./0.5 mm to yield the title compound, having R$_f$ 0.3 (TLC on silica gel in ethyl acetate) and NMR spectral peaks at 5.3–5.6 and 4.7 δ.

EXAMPLE 50

5-Nor-4-oxa-PGE$_1$, Bis(tetrahydropyranyl ether) (Formula CXXXIV: Q″ is

R$_2$ is n-pentyl, and R$_{21}$ is THP); and Methyl Ester (Formula CXXXV: R$_1$ is methyl)

Refer to Chart P. The formula-CXXXIII 2-decarboxy-2-hydroxymethyl-5-nor-4-oxa-PGF$_{1\alpha}$, 9,11,15- tris(tetrahydropyranyl ether) (Example 49, 1.9 g.) in 40 ml. of acetone at −20° C. under nitrogen is treated, while stirring, with 4 ml.of Jones reagent over a one-min. period. The mixture is stirred at −20° C. for an additional 35 min., then shaken with 300 ml. of ethyl acetate and 200 ml. of brine. The organic phase is washed with water and brine, dried, and concentrated under reduced pressure. The residue is subjected to silica gel chromatography, eluting with 50–70% ethyl acetate in Skellysolve B to yield 5-nor-4-oxa-PGE₁, bis-(tetrahydropyranyl ether), 1.3 g.

The above acid is treated in diethyl ether solution with an excess of ethereal diazomethane. After one min., acetic acid is added to destroy excess diazomethane. The mixture is washed with dilute aqueous sodium bicarbonate and brine, dried, and concentrated under reduced pressure. The residue is subjected to silica gel chromatography, eluting with 40–50% ethyl acetate in Skellysolve B to yield the title compound methyl ester, 0.85 g., having NMR spectral peaks at 5.5–5.7, 4.7, 3.7 (singlet), and 2.4–2.62 (triplet) δ.

EXAMPLE 51:

5-Nor-4-oxa-PGE₁, Methyl Ester (Formula CXXXVI: Q'. is

$R_1$ is methyl, and $R_2$ is n-pentyl)

Refer to Chart P. The formula-CXXXV 5-nor-4-oxa-PGE₁, bis(tetrahydropyranyl ether), methyl ester, (Example 50, 0.85 g.) is stirred with 20 ml. of acetic acid, 10 ml. of water, and 2 ml. of tetrahydrofuran at 40° C. for 4 hrs. The mixture is diluted with 150 ml. of cold ethyl acetate and washed with ice-cold dilute sodium hydroxide (15 ml. of 50% aqueous sodium hydroxide and 85 ml. of water). The organic phase is washed with aqueous sodium bicarbonate and brine, dried, and concentrated. The residue is subjected to silica gel chromatography, eluting with 0–4% methanol in ethyl acetate, to yield the title compound, 0.41 g., an oil, having NMR spectral peaks at 5.58–5.70, 3.70 (singlet), and 2.44–2.65 (triplet) δ; and mass spectral peaks (TMS derivative) at 485, 469, 429, 410, 379, 370, 339, and 285.

EXAMPLE 52

5-Nor-4-oxa-PGF₁ₐ, Methyl Ester (Formula CXXXVII: Q' is

$R_1$ is methyl, $R_2$ is n-pentyl, and ~ is alpha); and 5-Nor-4-oxa-PGF₁β, Methyl Ester (Formula CXXXVII: ~ is beta)

Refer to Chart P. The formula-CXXXVI 5-nor-4-oxa-PGE₁, methyl ester (Example 51, 0.29 g.) in 10 ml of methanol at 0° C. is added to a stirred solution of sodium borohydride (0.075 g.) in 0.75 ml. of water. The mixture is stirred at 0° C. for 10 min. and diluted with 100 ml. of ethyl acetate. The mixture is washed with brine, dried, and concentrated, The residue is subjected to silica gel chromatography, eluting with 0–15% ethanol in chloroform, to yield the PGF₁α title compound, 60 mg., an oil, having NMR spectral peaks at 5.4–5.55, 3.70 (singlet), and 2.49–2.7 (triplet) δ; mass spectral peaks (TMS derivative) at 559, 543, 503, 484, 469. 413, 394, 323, and 173; and $R_f$ 0.45 (TLC on silica gel in 10% ethanol in chloroform).

There is likewise obtained in the later-eluting (more polar) fractions the corresponding PGF₁β title compound, 170 mg., m.p. 96°–97° C., having NMR spectral peaks at 5.4–5.55, 3.70 (singlet), and 2.49–2.7 (triplet) δ; mass spectral peaks as observed above the PGF₁α compound; and $R_f$ 0.35 (TLC on silica gel in 10% ethanol in chloroform).

I claim:

1. An optically active compound of the formula:

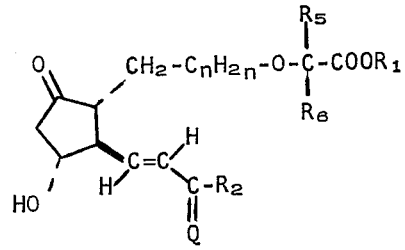

or a racemic compound of that formula and the mirror image thereof, wherein $C_nH_{2n}$ is alkylene of one to 10 carbon atoms, inclusive, with one to 5 carbon atoms, inclusive, between —CH₂— and —O—; wherein Q is

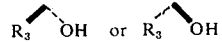

wherein $R_3$ is hydrogen or methyl; wherein $R_1$ is hydrogen, alkyl of one to 4 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro or alkyl of one to 4 carbon atoms, inclusive, or ethyl substituted in the β-position with 3 chloro; wherein $R_2$ is

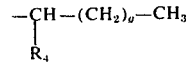

wherein $R_4$ is hydrogen or fluoro and g is one, 2, 3, 4, or 5; and wherein $R_5$, $R_6$, are hydrogen or alkyl of one to 4 carbon atoms, inclusive; including the lower akanoates thereof, and the pharmacologically acceptable salts thereof when $R_1$ is hydrogen.

2. A racemic compound according to claim 1.

3. An optically active compound according to claim 1.

4. A compound according to claim 3 wherein $C_nH_{2n}$ is straight chain alkylene of one to 5 carbon atoms, inclusive.

5. A compound according to claim 4 wherein $C_nH_{2n}$ is trimethylene.

6. A compound according to claim 5 wherein $R_5$ and $R_6$ are hydrogen or methyl, being the same or different.

7. A compound according to claim 6 wherein $R_5$ and $R_6$ are hydrogen.

8. A compound according to claim 7 wherein $R_2$ is pentyl.

9. A compound according to claim 8 wherein Q is

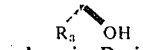

wherein $R_3$ is hydrogen or methyl.

10. A compound according to claim 8 wherein Q is

wherein $R_3$ is hydrogen or methyl.

11. A compound according to claim 10 wherein $R_1$ is hydrogen or alkyl of one to 4 carbon atoms, inclusive, including the pharmacologically acceptable salts thereof when $R_1$ is hydrogen.

12. A compound according to claim 11 wherein $R_1$ is hydrogen or alkyl of one to 4 carbon atoms, inclusive.

13. A compound according to claim 12 wherein $R_1$ is hydrogen, methyl, or ethyl.

14. 3-Oxa-$PGE_1$, a compound according to claim 13.

15. 3-Oxa-$PGE_1$, methyl ester, a compound according to claim 13.

16. 15-Methyl-3-oxa-$PGE_1$, a compound according to claim 13.

17. 15-Methyl-3-oxa-$PGE_1$, methyl ester, a compound according to claim 13.

18. An optically active compound of the formula:

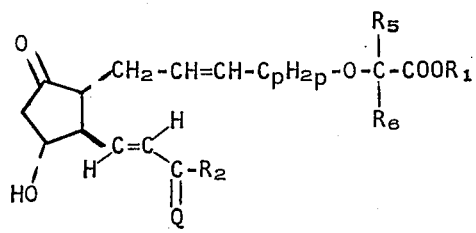

or a racemic compound of that formula and the mirror image thereof, wherein $C_pH_{2p}$ is alkylene of one to 8 carbon atoms, inclusive, with one, 2, or 3 carbon atoms, between —CH=CH— and —O—; wherein Q is

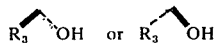

wherein $R_3$ is hydrogen or methyl; wherein $R_1$ is hydrogen, alkyl of one to 4 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro or alkyl of one to 4 carbon atoms, inclusive, or ethyl substituted in the β-position with 3 chloro; wherein $R_2$ is

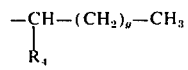

wherein $R_4$ is hydrogen or fluoro and g is one, 2, 3, 4, or 5; and wherein $R_5$ and $R_6$ are hydrogen or alkyl of one to 4 carbon atoms, inclusive; including the lower alkanoates thereof, and the pharmacologically acceptable salts thereof when $R_1$ is hydrogen.

19. A racemic compound according to claim 18.

20. An optically active compound according to claim 18.

21. A compound according to claim 20 wherein $C_nH_{2n}$ is straight chain alkylene of one to 5 carbon atoms, inclusive.

22. A compound according to claim 21 wherein $C_nH_{2n}$ is trimethylene.

23. A compound according to claim 22 wherein $R_5$ and $R_6$ are hydrogen or methyl, being the same or different.

24. A compound according to claim 23 wherein $R_5$ and $R_6$ are hydrogen.

25. A compound according to claim 24 wherein $R_2$ is pentyl.

26. A compound according to claim 25 wherein Q is

wherein $R_3$ is hydrogen or methyl.

27. A compound according to claim 25 wherein Q is

wherein $R_3$ is hydrogen or methyl.

28. A compound according to claim 27 wherein $R_1$ is hydrogen or alkyl of one to 4 carbon atoms, inclusive, including the pharmacologically acceptable salts thereof when $R_1$ is hydrogen.

29. A compound according to claim 28 wherein $R_1$ is hydrogen or alkyl of one to 4 carbon atoms, inclusive.

30. A compound according to claim 29 wherein $R_1$ is hydrogen methyl, or ethyl.

31. A compound according to claim 30 wherein the C-5 to C-6 double bond in the carboxyl-terminated side chain is in the cis configuration.

32. 3-oxa-$PGE_2$, -Oxa-PGE compound according to claim 31.

33. 3-Oxa-$PGE_2$, methyl ester, a compound according to claim 31.

34. 15-Methyl-3-oxa-$PGE_2$, a compound according to claim 31.

35. 15-Methyl-3-oxa-$PGE_2$, methyl ester, a compound according to claim 31.

36. An optically active compound of the formula:

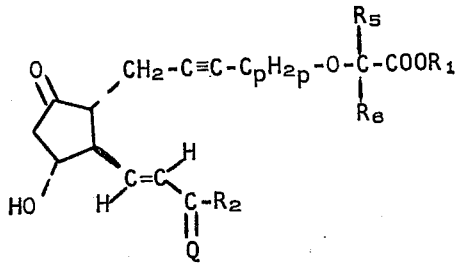

or a racemic compound of that formula and the mirror image thereof, wherein $C_pH_{2p}$ is alkylene of one to 8 carbon atoms, inclusive, with one, 2, or 3 carbon atoms, between —C≡C— and —O—; wherein Q is

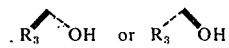

wherein $R_3$ is hydrogen or methyl; wherein $R_1$ is hydrogen, alkyl of one to 4 carbon atoms, inclusive, cycloalkyl of 3 to 10 carbon atoms, inclusive, phenyl, phenyl substituted with one, 2, or 3 chloro or alkyl of one to 4 carbon atoms, inclusive, or ethyl substituted in the β-position with 3 chloro; wherein R$_2$ is $$-\underset{R_4}{CH}-(CH_2)_g-CH_3$$

wherein R$_4$ is hydrogen or fluoro and g is one, 2, 3, 4, or 5; and wherein R$_5$ and R$_6$ are hydrogen or alkyl of one to 4 carbon atoms inclusive; including the lower alkanoates thereof, and the pharmacologically acceptable salts thereof when R$_1$ is hydrogen.

37. A racemic compound according to claim 36.
38. An optically active compound according to claim 36.
39. A compound according to claim 38 wherein C$_n$H$_{2n}$ is straight chain alkylene of one to 5 carbon atoms, inclusive.
40. A compound according to claim 39 wherein C$_n$H$_{2n}$ is trimethylene.
41. A compound according to claim 40 wherein R$_5$ and R$_6$ are hydrogen or methyl, being the same or different.
42. A compound according to claim 41 wherein R$_5$ and R$_6$ are hydrogen.
43. A compound according to claim 42 wherein R$_2$ is pentyl.
44. A compound according to claim 43 wherein Q is $$\underset{R_3}{\diagup}\overset{}{\diagdown}_{OH}$$

wherein R$_3$ is hydrogen or methyl.
45. A compound according to claim 43 wherein Q is $$\underset{R_3}{\diagup}\overset{}{\diagdown}_{OH}$$

wherein R$_3$ is hydrogen or methyl.
46. A compound according to claim 45 wherein R$_1$ is hydrogen or alkyl of one to 4 carbon atoms, inclusive, including the pharmacologically acceptable salts thereof when R$_1$ is hydrogen.
47. A compound according to claim 46 wherein R$_1$ is hydrogen or alkyl of one to 4 carbon atoms, inclusive.
48. A compound according to claim 47 wherein R$_1$ is hydrogen, methyl, or ethyl.
49. 3-Oxa-5,6-didehydro-PGE$_1$, a compound according to claim 48.
50. 3-Oxa-5,6-didehydro-PGE$_1$, methyl ester, a compound according to claim 48.
51. 15-Methyl-3-oxa-5,6-didehydro-PGE$_1$, a compound according to claim 48.
52. 15-Methyl-3-oxa-5,6-didehydro-PGE$_1$, methyl ester, a compound according to claim 48.
53. An optically active compound of the formula:

or a racemic compound of that formula and the mirror image thereof, wherein C$_n$H$_{2n}$ is alkylene of one to 10 carbon atoms, inclusive, with one to 5 carbon atoms, inclusive, between —CH$_2$— and —O—; wherein Q is $$\underset{R_3}{\diagup}\overset{}{\diagdown}_{OH} \quad or \quad \underset{R_3}{\diagup}\overset{}{\diagdown}_{OH}$$

wherein R$_3$ is hydrogen or methyl; wherein R$_1$ is hydrogen, alkyl of one to 4 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro or alkyl of one to 4 carbon atoms, inclusive, or ethyl substituted in the β-position with 3 chloro; wherein R$_2$ is $$-\underset{R_4}{CH}-(CH_2)_g-CH_3$$

wherein R$_4$ is hydrogen or fluoro and g is one, 2, 3, 4, or 5; and wherein R$_5$ and R$_6$ are hydrogen or alkyl of one to 4 carbon atoms, inclusive, including the lower alkanoates thereof, and the pharmacologically acceptable salts thereof when R$_1$ is hydrogen.

54. A racemic compound according to claim 53.
55. An optically active compound according to claim 53.
56. A compound according to claim 55 wherein C$_n$H$_{2n}$ is straight chain alkylene of one to 5 carbon atoms, inclusive.
57. A compound according to claim 56 wherein C$_n$H$_{2n}$ is trimethylene.
58. A compound according to claim 57 wherein R$_5$ and R$_6$ are hydrogen or methyl, being the same or different.
59. A compound according to claim 58 wherein R$_5$ and R$_6$ are hydrogen.
60. A compound according to claim 59 wherein R$_2$ is pentyl.
61. A compound according to claim 60 wherein Q is $$\underset{R_3}{\diagup}\overset{}{\diagdown}_{OH}$$

wherein R$_3$ is hydrogen or methyl.
62. A compound according to claim 60 wherein Q is $$\underset{R_3}{\diagup}\overset{}{\diagdown}_{OH}$$

wherein R$_3$ is hydrogen or methyl.
63. A compound according to claim 62 wherein R$_1$ is hydrogen or alkyl of one to 4 carbon atoms, inclusive, including the pharmacologically acceptable salts thereof when R$_1$ is hydrogen.
64. A compound according to claim 63 wherein R$_1$ is hydrogen or alkyl of one to 4 carbon atoms, inclusive.
65. A compound according to claim 64 wherein R$_1$ is hydrogen, methyl, or ethyl.
66. 3-Oxa-13,14-dihydro-PGE$_1$, a compound according to claim 65.
67. 3-Oxa-13,14-dihydro-PGE$_1$, methyl ester, a compound according to claim 65.
68. 15-Methyl-3-oxa-13,14-dihydro-PGE$_1$, a compound according to claim 65.

69. 15-Methyl-3-oxa-13,14-dihydro-PGE$_1$, methyl ester, a compound according to claim 65.

70. An optically active compound of the formula:

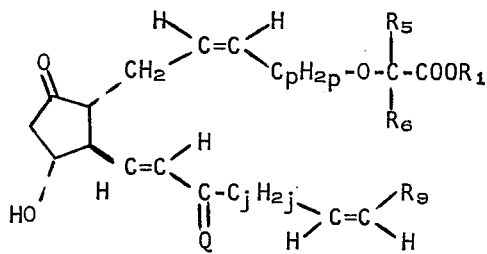

or a racemic compound of that formula and the mirror image thereof, wherein $C_jH_{2j}$ is alkylene of one to 4 carbon atoms, inclusive; wherein $C_pH_{2p}$ is alkylene of one to 8 carbon atoms, inclusive, with one, 2, or 3 carbon atoms between

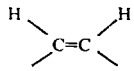

and —O—; wherein Q is

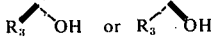

wherein $R_3$ is hydrogen or alkyl of one to 4 carbon atoms, inclusive, wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro or alkyl of one to 4 carbon atoms, inclusive, or ethyl substituted in the beta position with 3 chloro; wherein $R_4$ is alkyl of one to 4 carbon atoms, inclusive, substituted with zero, one, 2, or 3 fluoro; and wherein $R_5$ and $R_6$ are hydrogen or alkyl of one to 4 carbon atoms, inclusive; including the lower alkanoates thereof, and the pharmacologically acceptable salts thereof when $R_1$ is hydrogen.

* * * * *

UNITED STATES PATENT OFFICE
CERTIFICATE OF CORRECTION

Patent No. 3,944,593   Dated March 16, 1976

Inventor(s) Norman A. Nelson

It is certified that error appears in the above-identified patent and that said Letters Patent are hereby corrected as shown below:

Column 17, line 32, "PGR" should read -- PGB --. Column 39, line 23, "C C" should read -- C≡C --; line 27, "C C" should read -- C≡C --. Column 44, line 47, "-CHH$_2$" should read -- -CH$_2$ --. Column 45, line 67, "BR-" should read -- Br- --. Column 47, line 39, "C$_{m2m}$" should read -- C$_m$H$_{2m}$ --. Column 61, line 17, "palladiumon-" should read -- palladium-on- --. Column 114, line 36, "-PGE$_2$, -Oxa-PGE compound" should read -- -PGE$_2$, a compound --.

Column 114, line 2, "C$_n$H$_{2n}$" should read -- C$_p$H$_{2p}$ --; line 5, "C$_n$H$_{2n}$" should read -- C$_p$H$_{2p}$ --; line 37, "31" should read -- 18 --; line 39, "31" should read -- 18 --; line 41, "31" should read -- 18 --; line 43, "31" should read -- 18 --. Column 115, line 18, "C$_n$H$_{2n}$" should read -- C$_p$H$_{2p}$ --; line 21, "C$_n$H$_{2n}$" should read -- C$_p$H$_{2p}$ --; line 50, "48" should read -- 36 --; line 52, "48" should read -- 36 --; line 54, "48" should read -- 36 --; line 56, "48" should read -- 36 --.

Signed and Sealed this

Fourteenth Day of December 1976

[SEAL]

Attest:

RUTH C. MASON
Attesting Officer

C. MARSHALL DANN
Commissioner of Patents and Trademarks